(12) United States Patent
Jones et al.

(10) Patent No.: US 8,354,413 B2
(45) Date of Patent: Jan. 15, 2013

(54) QUINOLIN-4-ONE AND 4-OXODIHYDROCINNOLINE DERIVATIVES AS INHIBITORS OF POLY(ADP-RIBOSE) POLYMERASE (PARP)

(75) Inventors: Philip Jones, Rome (IT); Olaf Kinzel, Rome (IT); Uwe Koch, Rome (IT); Jesus Maria Ontoria Ontoria, Rome (IT); Giovanna Pescatore, Rome (IT); Rita Scarpelli, Rome (IT); Caterina Torrisi, Rome (IT)

(73) Assignee: Istituto di Ricerche di Biologia Molecolare P. Angeletti, S.R.L., Rome (IT)

( * ) Notice: Subject to any disclaimer, the term of this patent is extended or adjusted under 35 U.S.C. 154(b) by 366 days.

(21) Appl. No.: 12/673,555

(22) PCT Filed: Aug. 21, 2008

(86) PCT No.: PCT/GB2008/050731
§ 371 (c)(1),
(2), (4) Date: Feb. 15, 2010

(87) PCT Pub. No.: WO2009/027730
PCT Pub. Date: Mar. 5, 2009

(65) Prior Publication Data
US 2011/0207720 A1    Aug. 25, 2011

(30) Foreign Application Priority Data

Aug. 24, 2007   (GB) .................................. 0716532.7

(51) Int. Cl.
*A61K 31/497*   (2006.01)
*A61K 31/47*    (2006.01)
*A61K 31/535*   (2006.01)
*A01N 43/42*    (2006.01)
*C07D 215/30*   (2006.01)
*C07D 215/00*   (2006.01)
*C07D 215/12*   (2006.01)
*C07D 215/14*   (2006.01)

(52) U.S. Cl. ................. 514/253.07; 514/312; 514/230.5; 546/7; 546/153; 546/168

(58) Field of Classification Search ............. 514/253.07, 514/312, 230.05; 546/7, 153, 168
See application file for complete search history.

(56) References Cited

U.S. PATENT DOCUMENTS 5,985,894 A * 11/1999 Clemence et al. ............ 514/312

FOREIGN PATENT DOCUMENTS

| EP | 0343574 | 7/1994 |
|---|---|---|
| EP | 0498721 | 12/1999 |
| WO | WO 97/05114 | 2/1997 |
| WO | WO 02/12239 | 2/2002 |
| WO | WO 02/36576 | 5/2002 |
| WO | WO 02/090334 | 11/2002 |
| WO | WO 03/051879 | 6/2003 |
| WO | WO 03/093261 | 11/2003 |
| WO | WO 2004/080976 | 9/2004 |
| WO | WO 2005/023246 | 3/2005 |
| WO | WO 2006/021801 | 3/2006 |
| WO | WO 2007/059108 | 5/2007 |

OTHER PUBLICATIONS

Bryant et al., "Specific killing of BRCA2-deficient tumours with inhibitors of poly(ADP-ribose) polymerase", Nature, 434:913-917 (2005).
Del Buttero et al., "A convenient synthesis of 1-Alkyl-4-oxo-1,4-dihydrocinnolines", Synthesis,12:1059-1061 (1986).
Graziani et al., "Clinical perspectives of PARP inhibitors", Pharmacological Research 52(1):109-118 (2005).
Griera et al., "Synthesis and pharmacological evaluation of new cysLT1 receptor antagonists", Eur J Med Chem, 32(7-8):547-570, (1997).
Jagtap et al., "Poly(ADP-Ribose) Polymerase and the therapeutic effects of its inhibitors", Nature Reviews Drug Discovery, 4(5):421-440 (2005).
Peukert et al., "New inhibitors of poly(ADP-ribose) polymerase (PARP)", Expert. Opin. Ther. Patents, 14(11):1531-1551 (2004).
Southan et al., "Poly(ADP-Ribose) Polymerase Inhibitors", Current Medicinal Chemistry 10:321-340 (2003).
Woon, E.C.C. et al., "Poly(ADP-Ribose) Polymerase Inhibition—Where Now?", Current Medicinal Chemistry 12:2373-2392 (2005).

* cited by examiner

*Primary Examiner* — Samira Jean-Louis
(74) *Attorney, Agent, or Firm* — Yong Zhao; David A. Muthard; Matthew A. Leff

(57) ABSTRACT

The present invention relates to compounds of formula (I): and pharmaceutically acceptable salts or tautomers thereof which are inhibitors of poly(ADP-ribose)polymerase (PARP) and thus useful for the treatment of cancer, inflammatory diseases, reperfusion injuries, ischaemic conditions, stroke, renal failure, cardiovascular diseases, vascular diseases other than cardiovascular diseases, diabetes mellitus, neurodegenerative diseases, retroviral infections, retinal damage, skin senescence and UV-induced skin damage, and as chemo- or radiosensitizers for cancer treatment.

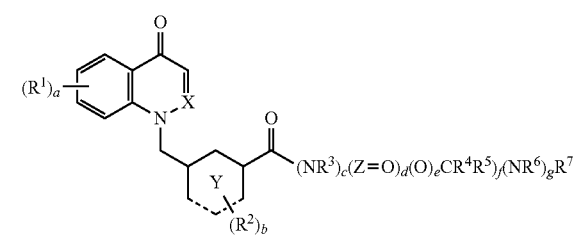

9 Claims, No Drawings

QUINOLIN-4-ONE AND 4-OXODIHYDROCINNOLINE DERIVATIVES AS INHIBITORS OF POLY(ADP-RIBOSE) POLYMERASE (PARP)

PRIORITY CLAIM

This application is a §371 National Stage Application of PCT/GB2008/050731, filed on Aug. 21, 2008, which claims priority from GB Provisional Application Serial Number 0716532.7, filed on Aug. 24, 2007.

The present invention relates to quinolin-4-one and 4-oxodihydrocinnoline derivatives which are inhibitors of the enzyme poly(ADP-ribose)polymerase (PARP), previously known as poly(ADP-ribose)synthase and poly(ADP-ribosyl) transferase. Compounds of the present invention are useful as mono-therapies in tumors with specific defects in DNA-repair pathways, particularly BRCA-1 and BRCA-2 deficient tumors. They are also useful in combination therapy, for example as enhancers of certain DNA-damaging agents such as anticancer agents and radiotherapy. Furthermore compounds of the present invention are useful for reducing cell necrosis (in stroke and myocardial infarction), down regulating inflammation and tissue injury, treating retroviral infections and protecting against the toxicity of chemotherapy.

Poly(ADP-ribose) polymerase (PARP) constitute a super family of eighteen proteins containing PARP catalytic domains (*Bioessays* (2004) 26:1148). These proteins include PARP-1, PARP-2, PARP-3, tankyrase-1, tankyrase-2, vault-PARP and TiPARP. PARP-1, the founding member, consists of three main domains: an amino (N)-terminal DNA-binding domain (DBD) containing two zinc fingers, the automodification domain, and a carboxy (C)-terminal catalytic domain.

PARP are nuclear and cytoplasmic enzymes that cleave $NAD^-$ to nicotinamide and ADP-ribose to form long and branched ADP-ribose polymers on target proteins, including topoisomerases, histones and PARP itself (*Biochem. Biophys. Res. Commun.* (1998) 245:1-10).

Poly(ADP-ribosyl)ation has been implicated in several biological processes, including DNA repair, gene transcription, cell cycle progression, cell death, chromatin functions and genomic stability.

The vast majority of PARP inhibitors to date interact with the nicotinamide binding domain of the enzyme and behave as competitive inhibitors with respect to $NAD^+$ (*Expert Opin. Ther. Patents* (2004) 14:1531-1551). Structural analogues of nicotinamide, such as benzamide and derivatives were among the first compounds to be investigated as PARP inhibitors. However, these molecules have a weak inhibitory activity and possess other effects unrelated to PARP inhibition. Thus, there is a need to provide potent inhibitors of the PARP enzyme.

Compounds of this invention are useful in the inhibition of poly(ADP-ribose)polymerase (PARP). They are particularly useful as inhibitors of PARP-1 and/or PARP-2. Moreover, the compounds of the present invention are distinct from most known PARP inhibitors, in that they do not contain a lactam/primary amide NH for hydrogen-bond interaction at the nicotinamide binding site.

The present invention provides compounds of formula I:

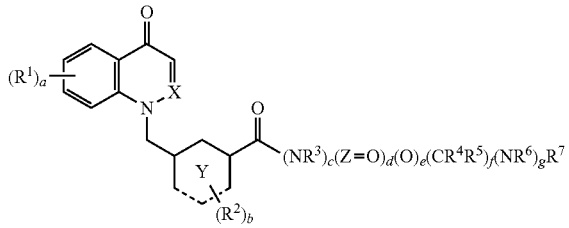

(I)

wherein:
a is 0, 1, 2, 3 or 4;
b is 0, 1, 2, 3 or 4;
c is 0 or 1;
d is 0 or 1;
e is 0 or 1;
f is 0, 1, 2, 3, 4 or 5;
g is 0 or 1;
X is N or CH;
Y is phenyl, a 5 membered unsaturated heterocycle containing 1, 2, 3 or 4 heteroatoms independently selected from O, N and S, but not more than one of which is O or S, or a 6 membered unsaturated heterocycle containing 1, 2, 3 or 4 nitrogen atoms;
Z is C or SO;
each $R^1$ is independently hydroxy, halogen, cyano, nitro, $C_{1-6}$alkyl, halo$C_{1-6}$alkyl, $C_{1-6}$ alkoxy or halo$C_{1-6}$ alkoxy;
each $R^2$ is independently hydroxy, halogen, cyano, nitro, $C_{1-6}$alkyl, halo$C_{1-6}$alkyl, $C_{1-6}$ alkoxy or halo$C_{1-6}$alkoxy;
$R^3$ is hydrogen or $C_{1-6}$alkyl;
each of $R^4$ and $R^5$ is independently hydrogen or $C_{1-6}$alkyl;
$R^6$ is hydrogen or $C_{1-6}$alkyl;
$R^7$ is hydrogen, hydroxy, cyano, oxo, halogen, $C_{1-6}$alkyl, $C_{2-10}$alkenyl, halo$C_{1-6}$alkyl, hydroxy$C_{1-6}$alkyl, $C_{1-6}$alkylcarbonyl, $C_{1-6}$alkoxy, halo$C_{1-6}$alkoxy, $C_{1-6}$alkoxycarbonyl, carboxy, nitro or a ring which is: $C_{6-10}$aryl; $C_{6-10}$aryloxy; $C_{6-10}$arylcarbonyl; $C_{3-10}$cycloalkyl; azetidinyl; a 5 or 6 membered saturated or partially saturated heterocyclic ring containing one, two or three atoms independently selected from N, O and S; a 5 membered heteroaromatic ring containing 1, 2, 3 or 4 heteroatoms independently selected from N, O and S, not more than one heteroatom of which is O or S; a 6 membered heteroaromatic ring containing 1, 2 or 3 nitrogen atoms; or a 7-13 membered unsaturated, partially saturated or saturated heterocyclic ring containing 1, 2, 3 or 4 heteroatoms independently selected from N, O and S; any of which rings being optionally substituted by one or more groups independently selected from A-$(CR^8R^9)_qR^{10}$;
each A is independently a direct bond, O, $(CH_2)_s(C=O)_r$, $(C=O)NR^{11}$, $NR^{11}(C=O)$, $(C=O)O$, $O(C=O)$, $(C=S)NR^{11}$, $NR^{11}$ or $S(O)_r$;
each q is independently 0, 1, 2, 3, or 4;
r is 0, 1 or 2;
s is 0, 1, 2 or 3;
t is 1 or 2;
each of $R^8$ and $R^9$ is independently hydrogen, hydroxy, halogen, $C_{1-6}$alkyl or halo$C_{1-6}$alkyl;
each $R^{10}$ is independently hydroxy, oxo, cyano, halogen, nitro, $C_{1-6}$alkyl, $C_{2-10}$alkenyl, halo$C_{1-6}$alkyl, amino, $C_{1-6}$alkylamino, di($C_{1-6}$alkyl)amino, ($C_{1-6}$alkylcarbonyl)amino or a ring which is: $C_{3-10}$cycloalkyl; $C_{6-10}$aryl; azetidinyl; a 5 or 6 membered saturated or partially saturated heterocyclic ring containing one, two or three atoms independently selected from N, O and S; a 5 membered heteroaromatic ring containing 1, 2, 3 or 4 heteroatoms independently selected from N, O and S, not more than one heteroatom of which is O or S; a 6 membered heteroaromatic ring containing 1, 2 or 3 nitrogen atoms; or a 7-13 membered unsaturated, partially saturated, or saturated heterocyclic ring containing 1, 2, 3 or 4 heteroatoms independently selected from N, O and S; any of which rings being optionally substituted by one or more groups independently selected from $R^{12}$;

$R^{11}$ is hydrogen or $R^{10}$;

each $R^{12}$ is independently hydroxy, oxo, cyano, halogen, nitro, $C_{1-6}$alkyl, $C_{1-6}$alkoxy, $C_{2-10}$alkenyl, halo$C_{1-6}$alkyl, halo$C_{1-6}$alkoxy, $C_{1-6}$alkylcarbonyl, —O(C=O)$C_{1-6}$alkyl, —(C=O)O$C_{1-6}$alkyl, amino, $C_{1-6}$alkylamino, di($C_{1-6}$alkyl) amino, ($C_{1-6}$alkylsulfonyl)amino, $C_{6-10}$aryl, $C_{6-10}$aryl$C_{1-6}$alkyl, a 5 membered heteroaromatic ring containing 1, 2, 3 or 4 heteroatoms independently selected from N, O and S, not more than one heteroatom of which is O or S or a 6 membered heteroaromatic ring containing 1, 2 or 3 nitrogen atoms; any of which rings being optionally substituted by one or more groups independently selected from halogen, $C_{1-6}$alkyl and halo$C_{1-6}$alkyl;

or a pharmaceutically acceptable salt, stereoisomer or tautomer thereof.

For the avoidance of doubt, the $R^1$ group can be substituted at any substitutable position of the fused benzene ring. Furthermore, the dotted line on the Y ring depicts one or two bonds to result in a 5 or a 6 membered Y ring. Moreover, it will be apparent that when $R^{10}$ is oxo, then A is absent and q is 0.

In an embodiment a is 0 or 1.
In another embodiment a is 1.
In an embodiment R' is hydroxy, halogen or $C_{1-6}$alkoxy.
Specific $R^1$ groups include fluorine, hydroxy and methoxy.
In an embodiment $R^1$ is halogen, for example fluorine.
In an embodiment b is 1.
In an embodiment c is 0.
In an embodiment d is 0.
In an embodiment e is 0.
In an embodiment f is 0.
In an embodiment g is 0.
In an embodiment each of c, d, e, f and g is 0.
In an embodiment Y is phenyl and each of c, d, e, f and g is 0.
In an embodiment X is CH. In another embodiment X is N.
In an embodiment Y is phenyl or a 6 membered unsaturated heterocycle containing 1, 2, 3 or 4 nitrogen atoms.
A particular Y group is phenyl.
In an embodiment $R^2$ is halogen.
A particular $R^2$ group is fluorine.
In an embodiment each of $R^4$ and $R^5$ is hydrogen.
In an embodiment $R^7$ is azetidinyl, a 5 or 6 membered saturated or partially saturated heterocyclic ring containing one, two or three atoms independently selected from N, O and S or a 7-13 membered partially saturated or saturated heterocyclic ring containing 1, 2, 3 or 4 heteroatoms independently selected from N, O and S; optionally substituted by one or more groups independently selected from A-$(CR^8R^9)_qR^{10}$.

In an embodiment $R^7$ is diazaspirodecyl, piperazinyl, diazepanyl, tetrahydrotriazolopyrazinyl, diazaspirononyl, diazabicyclooctyl, tetrahydropyridinyl, tetrahydrotriazolopyridinyl, decahydropyridopyrazinyl or octahydropyrazinooxazinyl; optionally substituted by one or more groups independently selected from A-$(CR^8R^9)_qR^{10}$.

In an embodiment $R^7$ is diazaspirodecyl, piperazinyl, diazepanyl, tetrahydrotriazolopyrazinyl, diazaspirononyl or diazabicyclooctyl; optionally substituted by one or more groups independently selected from A-$(CR^8R^9)_qR^{10}$.

In an embodiment, when $R^7$ is a ring it is optionally substituted by one, two or three groups independently selected from A-$(CR^8R^9)_qR^{10}$.

In another embodiment the $R^7$ ring is unsubstituted, monosubstituted or disubstituted.

In another embodiment the $R^7$ ring is unsubstituted or monosubstituted.

Particular $R^7$ groups include diazaspiro[4.5]decyl, [(fluorobenzyl)prolyl]piperazinyl, diazepanyl, propionylpiperazinyl, (trifluoromethyl)tetrahydro[1,2,4]triazolo[4,3-a]pyrazinyl, piperazinyl, diazaspiro[3.5]nonyl, diazabicyclo[2.2.2]octyl, (methylprolyl)piperazinyl, (trifluoro-N,N-dimethylalanyl)piperazinyl, [(methylazetidinyl)carbonyl]piperazinyl and ethyltetrahydro[1,2,4]triazolo[4,3-a]pyrazinyl. Further particular $R^7$ groups include ethyloxopiperazinyl, oxophenylpiperazinyl, cyclopentyloxopiperazinyl, (fluorophenyl)tetrahydropyridinyl, (trifluoroethyl)tetrahydro[1,2,3]triazolo[4,5-c]pyridinyl, cyclohexyloxopiperazinyl, (butoxycarbonyl)piperazinyl, piperazinyl, pyrimidinylpiperazinyl, butyrylpiperazinyl, (trifluoroacetyl)piperazinyl, (pentafluoroethyl)tetrahydro[1,2,4]triazolo[4,3-a]pyrazinyl, (chlorophenyl)oxopiperazinyl, (chlorofluorophenyl)oxopiperazinyl, (difluorophenyl)oxopiperazinyl, [(dimethylamino)methyl]tetrahydro[1,2,4]triazolo[4,3-a]pyrazinyl, cyclobutyltetrahydro[1,2,4]triazolo[4,3-a]pyrazinyl, butyltetrahydro[1,2,4]triazolo[4,3-a]pyrazinyl, (trifluoroethyl)tetrahydro[1,2,4]triazolo[4,3-a]pyrazinyl, oxodecahydropyrido[1,2-a]pyrazinyl and oxooctahydropyrazino[2,1-c][1,4]oxazinyl.

Specific $R^7$ groups include 1,8-diazaspiro[4.5]dec-8-yl, 4-[2-(4-fluorobenzyl)prolyl]piperazin-1-yl, 1,4-diazepan-1-yl, 4-propionylpiperazin-1-yl, 3-(trifluoromethyl)-5,6-dihydro[1,2,4]triazolo[4,3-a]pyrazin-7(8H)-yl, piperazin-1-yl, 2,6-diazaspiro[3.5]non-2-yl, 2,5-diazabicyclo[2.2.2]oct-2-yl, 4-(2-methylprolyl)piperazin-1-yl, 4-(3,3,3-trifluoro-N,N-dimethylalanyl)piperazin-1-yl, 4-[((2R)-2-methylazetidin-2-yl)carbonyl]piperazin-1-yl and 3-ethyl-5,6-dihydro[1,2,4]triazolo[4,3-a]pyrazin-7(8H)-yl. Further specific $R^7$ groups include 4-ethyl-oxopiperazin-1-yl, 3-oxo-4-phenylpiperazin-1-yl, 4-cyclopentyl-3-oxopiperazin-1-yl, 4-(4-fluorophenyl)-3,6-dihydropyridin-1(2H)-yl, 1-(2,2,2-trifluoroethyl)-1,4,6,7-tetrahydro-5H-[1,2,3]triazolo[4,5-c]pyridin-5-yl, 4-cyclohexyl-3-oxopiperazin-1-yl, 4-(tert-butoxycarbonyl)piperazin-1-yl, piperazin-1-yl, 4-pyrimidin-1-ylpiperazin-1-yl, 4-isobutyrylpiperazin-1-yl, 4-(trifluoroacetyl)piperazin-1-yl, 4-{[(2S)-2-(4-fluorobenzyl)pyrrolidinium-2-yl]carbonyl}piperazin-1-yl, 3-(pentafluoroethyl)-5,6-dihydro[1,2,4]triazolo[4,3-a]pyrazin-7(8H)-yl, 4-(2-chlorophenyl)-3-oxopiperazin-1-yl, 4-(3-chlorophenyl)-3-oxopiperazin-1-yl, 4-(2-chloro-4-fluorophenyl)-3-oxopiperazin-1-yl, 4-(3,4-difluorophenyl)-3-oxopiperazin-1-yl, 3-[(dimethylamino)methyl]-5,6-dihydro[1,2,4]triazolo[4,3-a]pyrazin-7(8H)-yl, 3-cyclobutyl-5,6-dihydro[1,2,4]triazolo[4,3-a]pyrazin-7(8H)-yl, 3-tert-butyl-5,6-dihydro[1,2,4]triazolo[4,3-a]pyrazin-7(8H)-yl, 3-(2,2,2-trifluoroethyl)-5,6-dihydro[1,2,4]]triazolo[4,3-a]pyrazin-7(8H)-yl, 4-oxooctahydro-2H-pyrido[1,2-a]pyrazin-2-yl and 6-oxohexahydropyrazino[2,1-c][1,4]oxazin-8(1H)-yl.

In an embodiment A is a direct bond, O, CO or NH.
In an embodiment A is a direct bond, CO or COO.
In an embodiment A is a direct bond or CO.
A particular A group is CO.
In an embodiment q is 0 or 1.

In an embodiment each of $R^8$ and $R^9$ is independently hydrogen, halogen or haloC$_{1-6}$alkyl.

In an embodiment one of $R^8$ and $R^9$ is hydrogen and the other is halogen or haloC$_{1-6}$alkyl.

In an embodiment one of $R^8$ and $R^9$ is hydrogen and the other haloC$_{1-6}$alkyl, for example trifluoromethyl.

In an embodiment each of $R^8$ and $R^9$ is independently hydrogen, methyl, fluorine or trifluoromethyl.

In an embodiment each of $R^8$ and $R^9$ is independently hydrogen, fluorine or trifluoromethyl.

In an embodiment $R^{10}$ is oxo, halogen, C$_{1-6}$ alkyl, haloC$_{1-6}$alkyl, amino, C$_{1-6}$ alkylamino, di(C$_{1-6}$alkyl)amino, C$_{3-7}$cycloalkyl, C$_{6-10}$aryl, azetidinyl, a 5 or 6 membered saturated or partially saturated heterocyclic ring containing one, two or three atoms independently selected from N, O and S or a 6 membered heteroaromatic ring containing 1, 2 or 3 nitrogen atoms; any of which rings being optionally substituted by one or more groups independently selected from $R^{12}$.

In an embodiment $R^{10}$ is halogen, C$_{1-6}$ alkyl, haloC$_{1-6}$alkyl, amino, C$_{1-6}$ alkylamino, di(C$_{1-6}$alkyl)amino, azetidinyl or a 5 or 6 membered saturated or partially saturated heterocyclic ring containing one, two or three atoms independently selected from N, O and S; any of which rings being optionally substituted by one or more groups independently selected from $R^{12}$.

In an embodiment $R^{10}$ is oxo, C$_{1-6}$alkyl, haloC$_{1-6}$alkyl, di(C$_{1-6}$alkyl)amino, azetidinyl, pyrrolidinyl, phenyl, cyclopentyl, cyclohexyl, pyrimidinyl or cyclobutyl; any of which rings being optionally substituted by one or more groups independently selected from $R^{12}$.

In an embodiment $R^{10}$ is C$_{1-6}$alkyl, haloC$_{1-6}$alkyl, di(C$_{1-6}$alkyl)amino, azetidinyl or pyrrolidinyl; any of which rings being optionally substituted by one or more groups independently selected from $R^{12}$.

In an embodiment, when $R^{10}$ is a ring it is optionally substituted by one, two or three groups independently selected from $R^{12}$. In another embodiment the $R^{10}$ ring is unsubstituted, monosubstituted or disubstituted. In another embodiment the $R^{10}$ ring is monosubstituted.

In an embodiment $R^{12}$ is C$_{1-6}$alkyl, C$_{6-10}$aryl or C$_{6-10}$arylC$_{1-6}$alkyl, any of which rings being optionally substituted by one or more groups independently selected from halogen, C$_{1-6}$alkyl and haloC$_{1-6}$alkyl. A further $R^{12}$ group is fluorine.

In an embodiment, when $R^{12}$ is a ring it is optionally substituted by one, two or three independently selected groups. In another embodiment the $R^{12}$ ring is monosubstituted.

A particular substituent on the $R^{12}$ ring is halogen, for example fluorine.

Particular $R^{12}$ groups are fluorobenzyl and methyl. Further particular $R^{12}$ groups are fluorine and chlorine.

Specific $R^{12}$ groups are 4-fluorobenzyl and methyl.

Particular $R^{10}$ groups are (fluorobenzyl)pyrrolidinyl, ethyl, trifluoromethyl, methylpyrrolidinyl, dimethylamino and methylazetidinyl. Further particular $R^{10}$ groups are oxo, phenyl, cyclopentyl, fluorophenyl, cyclohexyl, butyl, pyrimidinyl, propyl, chlorophenyl, chlorofluorophenyl, difluorophenyl and cyclobutyl.

Specific $R^{10}$ groups are 2-(4-fluorobenzyl)pyrrolidin-2-yl, ethyl, trifluoromethyl, 2-methylpyrrolidin-2-yl, dimethylamino and 2-methylazetidin-2-yl. Further specific $R^{10}$ groups are oxo, phenyl, cyclopentyl, 4-fluorophenyl, cyclohexyl, tertbutyl, pyrimidin-1-yl, isopropyl, 2-chlorophenyl, 3-chlorophenyl, 2-chloro-4-fluorophenyl, 3,4-difluorophenyl and cyclobutyl.

In an embodiment $R^{10}$ is not oxo.

In an embodiment:
Y is phenyl;
b is 1;
each of c, d, e, f and g is 0; and
$R^7$ is azetidinyl, a 5 or 6 membered saturated or partially saturated heterocyclic ring containing one, two or three atoms independently selected from N, O and S or a 7-13 membered partially saturated or saturated heterocyclic ring containing 1, 2, 3 or 4 heteroatoms independently selected from N, O and S; optionally substituted by one or more groups independently selected from A-(CR$^8$R$^9$)$_q$R$^{10}$.

In an embodiment:
Y is phenyl;
A is a direct bond, CO or COO; and
$R^{10}$ is oxo, halogen, C$_{1-6}$alkyl, haloC$_{1-6}$alkyl, amino, C$_{1-6}$alkylamino, di(C$_{1-6}$alkyl)amino, C$_{3-7}$cycloalkyl, C$_{6-10}$aryl, azetidinyl, a 5 or 6 membered saturated or partially saturated heterocyclic ring containing one, two or three atoms independently selected from N, O and S or a 6 membered heteroaromatic ring containing 1, 2 or 3 nitrogen atoms; any of which rings being optionally substituted by one or more groups independently selected from $R^{12}$.

The present invention also provides compounds of formula II:

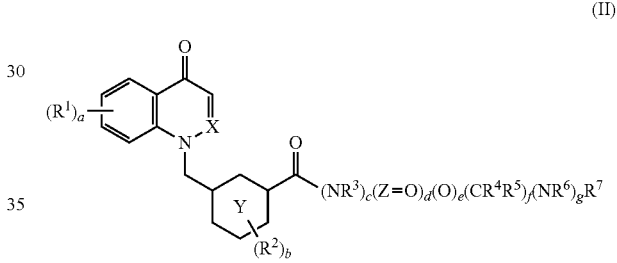

(II)

wherein:
a, b, c, d, e, f, g, X, Z, R$^1$, R$^2$, R$^3$, R$^4$, R$^5$, R$^6$ and R$^7$ are as defined above;
Y is phenyl or a 6 membered unsaturated heterocycle containing 1, 2, 3 or 4 nitrogen atoms;
or a pharmaceutically acceptable salt, stereoisomer or tautomer thereof.

The present invention also provides compounds of formula III:

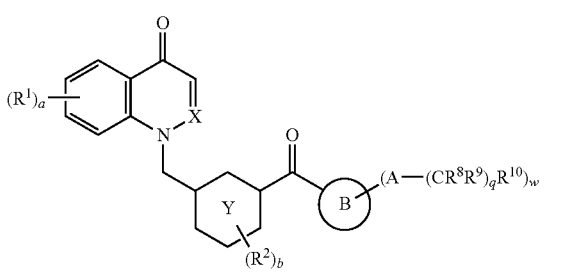

(III)

wherein:
a, b, q, A, R$^1$, R$^2$, R$^8$, R$^9$ and R$^{10}$ are as defined above;
Y is phenyl or a 6 membered unsaturated heterocycle containing 1, 2, 3 or 4 nitrogen atoms;
w is 0, 1, 2, 3 or 4;

B is azetidinyl, a 5 or 6 membered saturated or partially saturated heterocyclic ring containing one, two or three atoms independently selected from N, O and S or a 7-13 membered partially saturated or saturated heterocyclic ring containing 1, 2, 3 or 4 heteroatoms independently selected from N, O and S;

or a pharmaceutically acceptable salt, stereoisomer or tautomer thereof.

The preferred identities with reference to formulae II and III are as defined previously for formula I *mutatis mutandis*.

In an embodiment B is diazaspirodecyl, piperazinyl, diazepanyl, tetrahydrotriazolopyrazinyl, diazaspirononyl or diazabicyclooctyl. Further B groups are tetrahydropyridinyl, tetrahydrotriazolopyridinyl, decahydropyridopyrazinyl and octahydroyrazinooxazinyl.

Particular B groups include diazaspiro[4.5]decyl, piperazinyl, diazepanyl, tetrahydro[1,2,4]triazolo[4,3-a]pyrazinyl, diazaspiro[3.5]nonyl and diazabicyclo[2.2.2]octyl. Further particular B groups include tetrahydropyridinyl, tetrahydro[1,2,3]triazolo[4,5-c]pyridinyl, decahydropyrido[1,2-a]pyrazinyl and octahydropyrazino[2,1-c][1,4]oxazinyl.

Specific B groups include 1,8-diazaspiro[4.5]dec-8-yl, piperazin-1-yl, 1,4-diazepan-1-yl, 5,6-dihydro[1,2,4]triazolo[4,3-a]pyrazin-7(8H)-yl, 2,6-diazaspiro[3.5]non-2-yl and 2,5-diazabicyclo[2.2.2]oct-2-yl. Further specific B groups include 3,6-dihydropyridin-1(2H)-yl, 1,4,6,7-tetrahydro-5H-[1,2,3]triazolo[4,5-c]pyridin-5-yl, octahydro-2H-pyrido[1,2-a]pyrazin-2-yl and hexahydropyrazino[2,1-c][1,4]oxazin-8(1H)-yl.

In an embodiment w is 0, 1 or 2.

The present invention also includes within its scope N-oxides of the compounds of formula I above. In general, such N-oxides may be formed on any available nitrogen atom. The N-oxides may be formed by conventional means, such as reacting the compound of formula I with oxone in the presence of wet alumina.

The present invention includes within its scope prodrugs of the compounds of formula I above. In general, such prodrugs will be functional derivatives of the compounds of formula I which are readily convertible in vivo into the required compound of formula I. Conventional procedures for the selection and preparation of suitable prodrug derivatives are described, for example, in "Design of Prodrugs", ed. H. Bundgaard, Elsevier, 1985.

A prodrug may be a pharmacologically inactive derivative of a biologically active substance (the "parent drug" or "parent molecule") that requires transformation within the body in order to release the active drug, and that has improved delivery properties over the parent drug molecule. The transformation in vivo may be, for example, as the result of some metabolic process, such as chemical or enzymatic hydrolysis of a carboxylic, phosphoric or sulphate ester, or reduction or oxidation of a susceptible functionality.

The present invention includes within its scope solvates of the compounds of formula I and salts thereof, for example, hydrates.

The compounds of the present invention may have asymmetric centers, chiral axes, and chiral planes (as described in: E. L. Eliel and S. H. Wilen, *Stereochemistry of Carbon Compounds*, John Wiley & Sons, New York, 1994, pages 1119-1190), and occur as racemates, racemic mixtures, and as individual diastereomers, with all possible isomers and mixtures thereof, including optical isomers, all such stereoisomers being included in the present invention.

The compounds disclosed herein may exist as tautomers and both tautomeric forms are intended to be encompassed by the scope of the invention, even though only one tautomeric structure may be depicted. For example, compounds of formula I may tautomerise into compounds of the following structure:

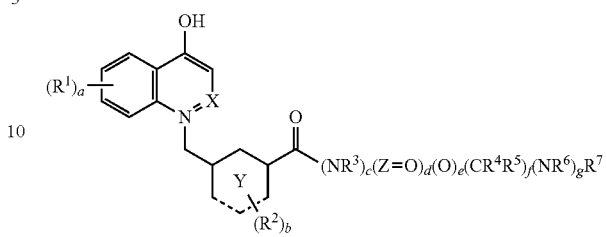

The compounds may exist in different isomeric forms, all of which are encompassed by the present invention.

The compounds may exist in a number of different polymorphic forms.

When any variable (e.g. $R^1$ and $R^2$, etc.) occurs more than one time in any constituent, its definition on each occurrence is independent at every other occurrence. Also, combinations of substituents and variables are permissible only if such combinations result in stable compounds. Lines drawn into the ring systems from substituents represent that the indicated bond may be attached to any of the substitutable ring atoms.

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results. The phrase "optionally substituted" should be taken to be equivalent to the phrase "unsubstituted or substituted with one or more substituents" and in such cases the preferred embodiment will have from zero to three substituents. More particularly, there are zero to two substituents. A substituent on a saturated, partially saturated or unsaturated heterocycle can be attached at any substitutable position.

As used herein, "alkyl" is intended to include both branched, straight-chain and cyclic saturated aliphatic hydrocarbon groups having the specified number of carbon atoms. For example, "$C_{1-6}$alkyl" is defined to include groups having 1, 2, 3, 4, 5 or 6 carbons in a linear, branched or cyclic arrangement. For example, "$C_{1-6}$alkyl" specifically includes methyl, ethyl, n-propyl, i-propyl, n-butyl, t-butyl, i-butyl, pentyl, hexyl, cyclopropyl, cyclobutyl, cyclopentyl and cyclohexyl and so on. Preferred alkyl groups are methyl and ethyl. The term "cycloalkyl" means a monocyclic, bicyclic or polycyclic saturated aliphatic hydrocarbon group having the specified number of carbon atoms. For example, "$C_{3-7}$cycloalkyl" includes cyclopropyl, methyl-cyclopropyl, 2,2-dimethyl-cyclobutyl, 2-ethyl-cyclopentyl, cyclohexyl, and so on. In an embodiment of the invention the term "cycloalkyl" includes the groups described immediately above and further includes monocyclic unsaturated aliphatic hydrocarbon groups. For example, "cycloalkyl" as defined in this embodiment includes cyclopropyl, methyl-cyclopropyl, 2,2-dimethyl-cyclobutyl, 2-ethyl-cyclopentyl, cyclohexyl, cyclopentenyl, cyclobutenyl, 7,7-dimethylbicyclo[2.2.1]heptyl and so on. Preferred cycloalkyl groups are cyclopropyl, cyclobutyl, cyclopentyl and cyclohexyl.

As used herein, the term "$C_{2-6}$alkenyl" refers to a non-aromatic hydrocarbon radical, straight or branched, containing from 2 to 6 carbon atoms and at least one carbon to carbon double bond. Preferably one carbon to carbon double bond is present, and up to four non-aromatic carbon-carbon double bonds may be present. Alkenyl groups include ethenyl, propenyl, butenyl and 2-methylbutenyl. Preferred alkenyl groups include ethenyl and propenyl.

As used herein, the term "$C_{2-6}$alkynyl" refers to a hydrocarbon radical straight or branched, containing from 2 to 6 carbon atoms and at least one carbon to carbon triple bond. Up to three carbon-carbon triple bonds may be present. Alkynyl groups include ethynyl, propynyl, butynyl, 3-methylbutynyl and so on. Preferred alkynyl groups include ethynyl and propynyl "Alkoxy" represents an alkyl group of indicated number of carbon atoms attached through an oxygen bridge. "Alkoxy" therefore encompasses the definitions of alkyl above. Examples of suitable alkoxy groups include methoxy, ethoxy, n-propoxy, i-propoxy, n-butoxy, s-butoxy, t-butoxy, cyclopropyloxy, cyclobutyloxy and cyclopentyloxy. The preferred alkoxy groups are methoxy and ethoxy. The term '$C_{6-10}$aryloxy' can be construed analogously, and an example of this group is phenoxy.

The terms "halo$C_{1-6}$alkyl" and "halo$C_{1-6}$alkoxy" mean a $C_{1-6}$alkyl or $C_{1-6}$alkoxy group in which one or more (in particular, 1 to 3) hydrogen atoms have been replaced by halogen atoms, especially fluorine or chlorine atoms. Preferred are fluoro$C_{1-6}$alkyl and fluoro$C_{1-6}$alkoxy groups, in particular fluoro$C_{1-3}$alkyl and fluoro$C_{1-3}$alkoxy groups, for example, $CF_3$, $CHF_2$, $CH_2F$, $CH_2CH_2F$, $CH_2CHF_2$, $CH_2CF_3$, $OCF_3$, $OCHF_2$, $OCH_2F$, $OCH_2CH_2F$, $OCH_2CHF_2$ or $OCH_2CF_3$, and most especially $CF_3$, $OCF_3$ and $OCHF_2$.

As used herein, the term "hydroxy$C_{1-6}$alkyl" means a $C_{1-6}$alkyl group in which one or more (in particular, 1 to 3) hydrogen atoms have been replaced by hydroxy groups. Preferred are $CH_2OH$, $CH_2CHOH$ and $CHOHCH_3$.

As used herein, the term "$C_{1-6}$alkylcarbonyl" or "$C_{1-6}$alkoxycarbonyl" denotes a $C_{1-6}$alkyl or $C_{1-6}$alkoxy radical, respectively, attached via a carbonyl (C=O) radical. Suitable examples of $C_{1-6}$alkylcarbonyl groups include methylcarbonyl, ethylcarbonyl, propylcarbonyl, isopropylcarbonyl and tert-butylcarbonyl. Examples of $C_{1-6}$alkoxycarbonyl include methoxycarbonyl, ethoxycarbonyl, propoxycarbonyl, isopropoxycarbonyl and tert-butoxycarbonyl. The term '$C_{6-10}$arylcarbonyl' can be construed analogously, and an example of this group is benzoyl.

As used herein, "$C_{6-10}$aryl" is intended to mean any stable monocyclic or bicyclic carbon ring of 6 to 10 atoms, wherein at least one ring is aromatic. Examples of such aryl elements include phenyl, naphthyl, tetrahydronaphthyl, indanyl and tetrahydrobenzo[7]annulene. The preferred aryl group is phenyl or naphthyl, especially phenyl.

7-13 membered heterocyclic rings include 7, 8, 9, 10, 11, 12 and 13 membered rings.

Examples of particular heterocycles of this invention are benzimidazolyl, benzofurandionyl, benzofuranyl, benzofurazanyl, benzopyrazolyl, benzotriazolyl, benzothienyl, benzoxazolyl, benzoxazolonyl, benzothiazolyl, benzothiadiazolyl, benzodioxolyl, benzoxadiazolyl, benzoisoxazolyl, benzoisothiazolyl, chromenyl, chromanyl, isochromanyl, carbazolyl, carbolinyl, cinnolinyl, epoxidyl, furyl, furazanyl, imidazolyl, indolinyl, indolyl, indolizinyl, indolinyl, isoindolinyl, indazolyl, isobenzofuranyl, isoindolyl, isoquinolyl, isothiazolyl, isoxazolyl, naphthpyridinyl, oxadiazolyl, oxazolyl, oxazolinyl, isoxazolinyl, oxetanyl, purinyl, pyranyl, pyrazinyl, pyrazolyl, pyridazinyl, pyridinyl, pyridopyridinyl, pyridazinyl, pyridinyl, pyrimidinyl, triazinyl, tetrazinyl, pyrrolyl, quinazolinyl, quinolinyl, quinoxalinyl, quinolizinyl, tetrahydropyranyl, tetrahydrothiopyranyl, tetrahydroisoquinolinyl, tetrazolyl, tetrazolopyridyl, thiadiazolyl, thiazolyl, thienyl, triazolyl, azetidinyl, 1,4-dioxanyl, hexahydroazepinyl, piperazinyl, piperidyl, pyridin-2-onyl, pyrrolidinyl, imidazolinyl, imidazolidinyl, pyrazolinyl, pyrrolinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydroisoquinolinyl, dihydrotetrazolyl, dihydrothiadiazolyl, dihydrothiazolyl, dihydrothienyl, dihydrotriazolyl, dihydroazetidinyl, dihydroisochromenyl, dihydrochromenyl, dihydroimidazolonyl, dihydrotriazolonyl, dihydrobenzodioxinyl, dihydrothiazolopyrimidinyl, dihydroimidazopyrazinyl, methylenedioxybenzoyl, tetrahydrofuranyl, tetrahydrothienyl, tetrahydroquinolinyl, thiazolidinonyl, imidazolonyl, isoindolinonyl, octahydroquinolizinyl, octahydroisoindolyl, imidazopyridinyl, azabicycloheptanyl, chromenonyl, triazolopyrimidinyl, dihydrobenzoxazinyl, thiazolotriazolyl, azoniabicycloheptanyl, azoniabicyclooctanyl, phthalazinyl, naphthyridinyl, pteridinyl, dihydroquinazolinyl, dihydrophthalazinyl, benzisoxazolyl, tetrahydronaphthyridinyl, dibenzo[b,d]furanyl, dihydrobenzothiazolyl, imidazothiazolyl, tetrahydroindazolyl, tetrahydrobenzothienyl, hexahydronaphthyridinyl, tetrahydroimidazopyridinyl, tetrahydroimidazopyrazinyl, pyrrolopyridinyl, diazepanyl and N-oxides thereof. Attachment of a heterocyclyl substituent can occur via a carbon atom or via a heteroatom.

Preferred 5 or 6 membered saturated or partially saturated heterocycles are pyrrolidinyl, piperidinyl, piperazinyl, morpholinyl, tetrahydrofuran and thiomorpholinyl.

A preferred 7 membered saturated heterocycle is diazepanyl.

Preferred 5 membered heteroaromatic rings are thienyl, thiazolyl, pyrazolyl, isoxazolyl, isothiazolyl, imidazolyl, thiadiazolyl, oxazolyl, oxadiazolyl, triazolyl, tetrazolyl, furyl and pyrrolyl.

Preferred 6 membered heteraromatic rings are pyridinyl, pyrimidinyl, pyridazinyl and pyrazinyl.

Preferred 7-10 membered partially saturated or unsaturated heterocyclic rings are tetrahydroquinolinyl, quinolinyl, indolyl, imidazopyridinyl, benzothiazolyl, quinoxalinyl, benzothiadiazolyl, benzoxazolyl, dihydrobenzodioxinyl, benzotriazolyl, benzodioxolyl, dihydroisoindolyl, dihydroindolyl, tetrahydroisoquinolinyl, isoquinolinyl, benzoisothiazolyl, dihydroimidazopyrazinyl, benzothienyl, benzoxadiazolyl, thiazolotriazolyl, dihydrothiazolopyrimidinyl, dihydrobenzoxazinyl, dihydrobenzofuranyl, benzimidazolyl, benzofuranyl, dihydrobenzoxazolyl, dihydroquinazolinyl, dihydrophthalazinyl, indazolyl, benzisoxazolyl, tetrahydronaphthyridinyl, triazolopyrimidinyl, dibenzo[b,d]furanyl, naphthyridinyl, dihydroquinolinyl, dihydroisochromenyl, dihydrochromenyl, dihydrobenzothiazolyl, imidazothiazolyl, tetrahydroindazolyl, tetrahydrobenzothienyl, hexahydronaphthyridinyl, tetrahydroimidazopyridinyl, tetrahydroimidazopyrazinyl, pyrrolopyridinyl, quinazolinyl and indolizinyl.

As used herein, the term "halogen" refers to fluorine, chlorine, bromine and iodine, of which fluorine and chlorine are preferred.

Particular compounds within the scope of the present invention are:

1-[3-(8-aza-1-azoniaspiro[4.5]dec-8-ylcarbonyl)-4-fluorobenzyl]-4-oxo-1,4-dihydroquinolinium bis(trifluoroacetate);
1-[4-fluoro-3-({4-[2-(4-fluorobenzyl)prolyl]piperazin-1-yl}carbonyl)benzyl]quinolin-4(1H)-one;
1-[3-(8-aza-1-azoniaspiro[4.5]dec-8-ylcarbonyl)-4-fluorobenzyl]-4-oxo-1,4-dihydrocinnolin-1-ium bis(trifluoroacetate);
1-[3-(1,4-diazepan-1-ylcarbonyl)-4-fluorobenzyl]quinolin-4(1H)-one;
1-{4-fluoro-3-[(4-propionylpiperazin-1-yl)carbonyl]benzyl}quinolin-4(1H)-one;
1-(4-fluoro-3-{[3-(trifluoromethyl)-5,6-dihydro[1,2,4]triazolo[4,3-a]pyrazin-7(8H)-yl]carbonyl}benzyl)quinolin-4(1H)-one;
1-[3-(1,8-diazaspiro[4.5]dec-8-ylcarbonyl)-4-fluorobenzyl]quinolin-4(1H)-one;
1-[4-fluoro-3-(piperazin-1-ylcarbonyl)benzyl]quinolin-4(1H)-one;
1-[3-(2,6-diazaspiro[3.5]non-2-ylcarbonyl)-4-fluorobenzyl]quinolin-4(1H)-one;
1-[3-(2,5-diazabicyclo[2.2.2]oct-2-ylcarbonyl)-4-fluorobenzyl]quinolin-4(1H)-one;
1-(4-fluoro-3-{[4-(2-methylprolyl)piperazin-1-yl]carbonyl}benzyl)quinolin-4(1H)-one;
1-(4-fluoro-3-{[4-(3,3,3-trifluoro-N,N-dimethylalanyl)piperazin-1-yl]carbonyl}benzyl)quinolin-4(1H)-one;
(2R)-2-[(4-{2-fluoro-5-[(4-oxoquinolin-1(4H)-yl)methyl]benzoyl}piperazin-1-yl)carbonyl]-2-methylazetidinium trifluoroacetate;
1-{4-fluoro-3-[(4-propionylpiperazin-1-yl)carbonyl]benzyl}-4-oxo-1,4-dihydrocinnolin-1-ium trifluoroacetate;
1-{3-[(3-ethyl-5,6-dihydro[1,2,4]triazolo[4,3-a]pyrazin-2-ium-7(8H)-yl)carbonyl]-4-fluorobenzyl}-4-oxo-1,4-dihydrocinnolin-1-ium bis(trifluoroacetate);
1-(4-fluoro-3-{[3-(trifluoromethyl)-5,6-dihydro[1,2,4]triazolo[4,3-a]pyrazin-7(8H)-yl]carbonyl}benzyl)-4-oxo-1,4-dihydrocinnolin-1-ium trifluoroacetate;
and other pharmaceutically acceptable salts, free bases and tautomers thereof.

Further particular compounds within the scope of the present invention are:
8-fluoro-1-(4-fluoro-3-{[3-(trifluoromethyl)-5,6-dihydro[1,2,4]triazolo[4,3-a]pyrazin-7(8H)-yl]carbonyl}benzyl)-4-oxo-1,4-dihydrocinnolin-1-ium trifluoroacetate;
1-{3-[(4-ethyl-3-oxopiperazin-1-yl)carbonyl]-4-fluorobenzyl}-8-hydroxycinnolin-4(1H)-one;
1-{4-fluoro-3-[(3-oxo-4-phenylpiperazin-1-yl)carbonyl]benzyl}-4-oxo-1,4-dihydroquinolinium trifluoroacetate;
1-{3-[(4-cyclopentyl-3-oxopiperazin-1-yl)carbonyl]-4-fluorobenzyl}-4-oxo-1,4-dihydroquinolinium trifluoroacetate;
1-(4-fluoro-3-{[4-(4-fluorophenyl)-3,6-dihydropyridin-1(2H)-yl]carbonyl}benzyl)-4-oxo-1,4-dihydroquinolinium trifluoroacetate;
1-(4-fluoro-3-{[1-(2,2,2-trifluoroethyl)-1,4,6,7-tetrahydro-5H-[1,2,3]triazolo[4,5-c]pyridin-5-yl]carbonyl}benzyl)-4-oxo-1,4-dihydrocinnolin-1-ium trifluoroacetate;
1-{3-[(4-cyclohexyl-3-oxopiperazin-1-yl)carbonyl]-4-fluorobenzyl}-4-oxo-1,4-dihydrocinnolin-1-ium trifluoroacetate;
1-{3-[(4-cyclopentyl-3-oxopiperazin-1-yl)carbonyl]-4-fluorobenzyl}-4-oxo-1,4-dihydrocinnolin-1-ium trifluoroacetate;
1-(3-{[4-(tert-butoxycarbonyl)piperazin-1-yl]carbonyl}-4-fluorobenzyl)-4-oxo-1,4-dihydrocinnolin-1-ium trifluoroacetate;
1-[4-fluoro-3-(piperazin-1-ylcarbonyl)benzyl]cinnolin-4(1H)-one;
2-(4-{2-fluoro-5-[(4-oxocinnolin-1(4H)-yl)methyl]benzoyl}piperazin-1-yl)pyrimidin-1-ium trifluoroacetate;
1-{4-fluoro-3-[(3-oxo-4-phenylpiperazin-1-yl)carbonyl]benzyl}-4-oxo-1,4-dihydrocinnolin-1-ium trifluoroacetate;
1-{4-fluoro-3-[(4-isobutyrylpiperazin-1-yl)carbonyl]benzyl}-4-oxo-1,4-dihydrocinnolin-1-ium trifluoroacetate;
1-(4-fluoro-3-{[4-(trifluoroacetyl)piperazin-1-yl]carbonyl}benzyl)-4-oxo-1,4-dihydrocinnolin-1-ium trifluoroacetate;
1-{4-fluoro-3-[(4-{[(2S)-2-(4-fluorobenzyl)pyrrolidinium-2-yl]carbonyl}piperazin-1-yl)carbonyl]benzyl}-4-oxo-1,4-dihydrocinnolin-1-ium bis(trifluoroacetate);
1-{4-fluoro-3-[(4-{[(2R)-2-methylazetidin-2-yl]carbonyl}piperazin-1-yl)carbonyl]benzyl}cinnolin-4(1H)-one;
1-[3-(2,5-diazabicyclo[2.2.2]oct-2-ylcarbonyl)-4-fluorobenzyl]cinnolin-4(1H)-one;
1-[3-(1,4-diazepan-1-ylcarbonyl)-4-fluorobenzyl]cinnolin-4(1H)-one;
1-(4-fluoro-3-{[3-(pentafluoroethyl)-5,6-dihydro[1,2,4]triazolo[4,3-a]pyrazin-7(8H)-yl]carbonyl}benzyl)-4-oxo-1,4-dihydrocinnolin-1-ium trifluoroacetate;
1-(3-{[4-(2-chlorophenyl)-3-oxopiperazin-1-yl]carbonyl}-4-fluorobenzyl)-4-oxo-1,4-dihydrocinnolin-1-ium trifluoroacetate;
1-(3-{[4-(3-chlorophenyl)-3-oxopiperazin-1-yl]carbonyl}-4-fluorobenzyl)-4-oxo-1,4-dihydrocinnolin-1-ium trifluoroacetate;
1-(3-{[4-(2-chloro-4-fluorophenyl)-3-oxopiperazin-1-yl]carbonyl}-4-fluorobenzyl)-4-oxo-1,4-dihydrocinnolin-1-ium trifluoroacetate;
1-(3-{[4-(3,4-difluorophenyl)-3-oxopiperazin-1-yl]carbonyl}-4-fluorobenzyl)-4-oxo-1,4-dihydrocinnolin-1-ium trifluoroacetate;
1-(3-{[3-[(dimethylamino)methyl]-5,6-dihydro[1,2,4]triazolo[4,3-a]pyrazin-7(8H)-yl]carbonyl}-4-fluorobenzyl)cinnolin-4(1H)-one;
1-{3-[(3-cyclobutyl-5,6-dihydro[1,2,4]triazolo[4,3-a]pyrazin-7(8H)-yl)carbonyl]-4-fluorobenzyl}-4-oxo-1,4-dihydrocinnolin-1-ium trifluoroacetate;
1-{3-[(3-tert-butyl-5,6-dihydro[1,2,4]triazolo[4,3-a]pyrazin-7(8H)-yl)carbonyl]-4-fluorobenzyl}-4-oxo-1,4-dihydrocinnolin-1-ium trifluoroacetate;
1-(4-fluoro-3-{[3-(2,2,2-trifluoroethyl)-5,6-dihydro[1,2,4]triazolo[4,3-a]pyrazin-7(8H)-yl]carbonyl}benzyl)-4-oxo-1,4-dihydrocinnolin-1-ium trifluoroacetate;
1-(4-fluoro-3-{[4-(4-fluorophenyl)-3,6-dihydropyridin-1(2H)-yl]carbonyl}benzyl)cinnolin-4(1H)-one;
5-fluoro-1-(4-fluoro-3-{[3-(trifluoromethyl)-5,6-dihydro[1,2,4]triazolo[4,3-a]pyrazin-7(8H)-yl]carbonyl}benzyl)-4-oxo-1,4-dihydrocinnolin-1-ium trifluoroacetate;
1-{3-[(4-cyclohexyl-3-oxopiperazin-1-yl)carbonyl]-4-fluorobenzyl}-5-fluoro-4-oxo-1,4-dihydrocinnolin-1-ium trifluoroacetate;
1-{3-[(4-cyclopentyl-3-oxopiperazin-1-yl)carbonyl]-4-fluorobenzyl}-5-fluoro-4-oxo-1,4-dihydrocinnolin-1-ium trifluoroacetate;
1-[3-(2,5-diazabicyclo[2.2.2]oct-2-ylcarbonyl)-4-fluorobenzyl]-5-fluorocinnolin-4(1H)-one 6-fluoro-1-(4-fluoro-3-{[3-(trifluoromethyl)-5,6-dihydro[1,2,4]triazolo[4,3-a]pyrazin-7(8H)-yl]carbonyl}benzyl)-4-oxo-1,4-dihydrocinnolin-1-ium trifluoroacetate;

1-{3-[(4-cyclohexyl-3-oxopiperazin-1-yl)carbonyl]-4-fluorobenzyl}-6-fluoro-4-oxo-1,4-dihydrocinnolin-1-ium trifluoroacetate;
1-{3-[(4-cyclopentyl-3-oxopiperazin-1-yl)carbonyl]-4-fluorobenzyl}-6-fluoro-4-oxo-1,4-dihydrocinnolin-1-ium trifluoroacetate;
1-[3-(2,5-diazabicyclo[2.2.2]oct-2-ylcarbonyl)-4-fluorobenzyl]-6-fluorocinnolin-4(1H)-one;
7-fluoro-1-(4-fluoro-3-{[3-(trifluoromethyl)-5,6-dihydro[1,2,4]triazolo[4,3-a]pyrazin-7(8H)-yl]carbonyl}benzyl)-4-oxo-1,4-dihydrocinnolin-1-ium trifluoroacetate;
1-{3-[(4-cyclohexyl-3-oxopiperazin-1-yl)carbonyl]-4-fluorobenzyl}-7-fluoro-4-oxo-1,4-dihydrocinnolin-1-ium trifluoroacetate;
1-{3-[(4-cyclopentyl-3-oxopiperazin-1-yl)carbonyl]-4-fluorobenzyl}-7-fluoro-4-oxo-1,4-dihydrocinnolin-1-ium trifluoroacetate;
1-[3-(2,5-diazabicyclo[2.2.2]oct-2-ylcarbonyl)-4-fluorobenzyl]-7-fluorocinnolin-4(1H)-one;
1-{3-[(4-cyclohexyl-3-oxopiperazin-1-yl)carbonyl]-4-fluorobenzyl}-8-fluoro-4-oxo-1,4-dihydrocinnolin-1-ium trifluoroacetate;
1-{3-[(4-cyclopentyl-3-oxopiperazin-1-yl)carbonyl]-4-fluorobenzyl}-8-fluoro-4-oxo-1,4-dihydrocinnolin-1-ium trifluoroacetate;
1-[3-(2,5-diazabicyclo[2.2.2]oct-2-ylcarbonyl)-4-fluorobenzyl]-8-fluorocinnolin-4(1H)-one;
1-(4-fluoro-3-{[3-(trifluoromethyl)-5,6-dihydro[1,2,4]triazolo[4,3-a]pyrazin-7(8H)-yl]carbonyl}benzyl)-7-methoxy-4-oxo-1,4-dihydrocinnolin-1-ium trifluoroacetate;
1-{3-[(4-cyclohexyl-3-oxopiperazin-1-yl)carbonyl]-4-fluorobenzyl}-7-methoxy-4-oxo-1,4-dihydrocinnolin-1-ium trifluoroacetate;
1-{3-[(4-cyclopentyl-3-oxopiperazin-1-yl)carbonyl]-4-fluorobenzyl}-7-methoxy-4-oxo-1,4-dihydrocinnolin-1-ium trifluoroacetate;
1-[3-(2,5-diazabicyclo[2.2.2]oct-2-ylcarbonyl)-4-fluorobenzyl]-7-methoxycinnolin-4(1H)-one;
1-(4-fluoro-3-{[3-(trifluoromethyl)-5,6-dihydro[1,2,4]triazolo[4,3-a]pyrazin-7(8H)-yl]carbonyl}benzyl)-8-hydroxy-4-oxo-1,4-dihydrocinnolin-1-ium trifluoroacetate;
1-{3-[(4-cyclopentyl-3-oxopiperazin-1-yl)carbonyl]-4-fluorobenzyl}-8-hydroxy-4-oxo-1,4-dihydrocinnolin-1-ium trifluoroacetate;
1-(3-{[4-(2-chloro-4-fluorophenyl)-3-oxopiperazin-1-yl]carbonyl}-4-fluorobenzyl)-8-hydroxy-4-oxo-1,4-dihydrocinnolin-1-ium trifluoroacetate;
1-{4-fluoro-3-[(4-propionylpiperazin-1-yl)carbonyl]benzyl}-8-hydroxy-4-oxo-1,4-dihydrocinnolin-1-ium trifluoroacetate;
1-{4-fluoro-3-[(4-oxooctahydro-2H-pyrido[1,2-a]pyrazin-2-yl)carbonyl]benzyl}-8-hydroxy-4-oxo-1,4-dihydrocinnolin-1-ium trifluoroacetate;
1-{4-fluoro-3-[(6-oxohexahydropyrazino[2,1-c][1,4]oxazin-8(1H)-yl)carbonyl]benzyl}-8-hydroxy-4-oxo-1,4-dihydrocinnolin-1-ium trifluoroacetate;
and other pharmaceutically acceptable salts, free bases and tautomers thereof.

Included in the instant invention is the free base of compounds of Formula I, as well as the pharmaceutically acceptable salts and stereoisomers thereof. The compounds of the present invention can be protonated at the N atom(s) of an amine and/or N containing heterocycle moiety to form a salt. The term "free base" refers to the amine compounds in non-salt form. The encompassed pharmaceutically acceptable salts not only include the salts exemplified for the specific compounds described herein, but also all the typical pharmaceutically acceptable salts of the free form of compounds of Formula I. The free form of the specific salt compounds described may be isolated using techniques known in the art. For example, the free form may be regenerated by treating the salt with a suitable dilute aqueous base solution such as dilute aqueous NaOH, potassium carbonate, ammonia and sodium bicarbonate. The free forms may differ from their respective salt forms somewhat in certain physical properties, such as solubility in polar solvents, but the acid and base salts are otherwise pharmaceutically equivalent to their respective free forms for purposes of the invention.

The pharmaceutically acceptable salts of the instant compounds can be synthesized from the compounds of this invention which contain a basic or acidic moiety by conventional chemical methods. Generally, the salts of the basic compounds are prepared either by ion exchange chromatography or by reacting the free base with stoichiometric amounts or with an excess of the desired salt-forming inorganic or organic acid in a suitable solvent or various combinations of solvents. Similarly, the salts of the acidic compounds are formed by reactions with the appropriate inorganic or organic base.

Thus, pharmaceutically acceptable salts of the compounds of this invention include the conventional non-toxic salts of the compounds of this invention as formed by reacting a basic instant compound with an inorganic, organic acid or polymeric acid. For example, conventional non-toxic salts include those derived from inorganic acids such as hydrochloric, hydrobromic, hydroiodic, sulfuric, sulfurous, sulfamic, phosphoric, phosphorous, nitric and the like, as well as salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxy-benzoic, fumaric, toluenesulfonic, methanesulfonic, ethane disulfonic, oxalic, isethionic, palmitic, gluconic, ascorbic, phenylacetic, aspartic, cinnamic, pyruvic, ethanesulfonic, ethane, disulfonic, valeric, trifluoroacetic and the like. Examples of suitable polymeric salts include those derived from the polymeric acids such as tannic acid, carboxymethyl cellulose. Preferably, a pharmaceutically acceptable salt of this invention contains 1 equivalent of a compound of formula (I) and 1, 2 or 3 equivalent of an inorganic or organic acid. More particularly, pharmaceutically acceptable salts of this invention are the trifluoroacetate or the chloride salts, especially the trifluoroacetate salts.

When the compound of the present invention is acidic, suitable "pharmaceutically acceptable salts" refers to salts prepared form pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc and the like. Particularly preferred are the ammonium, calcium, magnesium, potassium and sodium salts. Salts derived from pharmaceutically acceptable organic non-toxic bases include salts of primary, secondary and tertiary amines, substituted amines including naturally occurring substituted amines, cyclic amines and basic ion exchange resins, such as arginine, lysine, betaine caffeine, choline, $N,N^1$-dibenzylethylenediamine, ethylamine, diethylamine, 2-diethylaminoethanol, 2-dimethylaminoethanol, ethanolamine, diethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine tripropylamine, tromethamine, dicyclohexylamine, butylamine, benzylamine, phenylbenzylamine, tromethamine and the like.

The preparation of the pharmaceutically acceptable salts described above and other typical pharmaceutically acceptable salts is more fully described by Berg et al (1977) *J. Pharm. Sci., 'Pharmaceutical Salts'*, 66:1-19.

It will also be noted that the compounds of the present invention are potentially internal salts or zwitterions, since under physiological conditions a deprotonated acidic moiety in the compound, such as a carboxyl group, may be anionic, and this electronic charge might then be balanced off internally against the cationic charge of a protonated or alkylated basic moiety, such as a quaternary nitrogen atom.

The compounds of the invention can be used in a method of treatment of the human or animal body by therapy.

The invention provides compounds for use in the treatment or prevention of conditions which can be ameliorated by the inhibition of poly(ADP-ribose)polymerase (PARP) (see, for example, *Nature Review Drug Discovery* (2005) 4:421-440).

Thus, the present invention provides a compound of formula I for use in the manufacture of a medicament for the treatment or prevention of conditions which can be ameliorated by the inhibition of poly(ADP-ribose)polymerase (PARP).

The present invention also provides a method for the treatment or prevention of conditions which can be ameliorated by the inhibition of poly(ADP-ribose)polymerase (PARP), which method comprises administration to a patient in need thereof of an effective amount of a compound of formula I or a composition comprising a compound of formula I.

The PARP inhibitors of the present invention are useful for the treatment of the diseases specified in WO 2005/082368.

The compounds of the invention are useful for the treatment of inflammatory diseases, including conditions resulting from organ transplant rejection, such as; chronic inflammatory diseases of the joints, including arthritis, rheumatoid arthritis, osteoarthritis and bone diseases associated with increased bone resorption; inflammatory bowel diseases such as ileitis, ulcerative colitis, Barrett's syndrome, and Crohn's disease; inflammatory lung diseases such as asthma, adult respiratory distress syndrome, and chronic obstructive airway disease; inflammatory diseases of the eye including corneal dystrophy, trachoma, onchocerciasis, uveitis, sympatheticophthalmitis and endophthalmitis; chronic inflammatory diseases of the gum, including gingivitis and periodontitis; tuberculosis; leprosy; inflammatory diseases of the kidney including uremic complications, glomerulonephritis and nephrosis; inflammatory diseases of the skin including sclerodermatitis, psoriasis and eczema; inflammatory diseases of the central nervous system, including chronic demyelinating diseases of the nervous system, multiple sclerosis, AIDS-related neurodegeneration and Alzheimer's disease, infectious meningitis, encephalomyelitis, Parkinson's disease, Huntington's disease, amyotrophic lateral sclerosis and viral or autoimmune encephalitis; diabetic complications, including, but not limited to, immune-complex vasculitis, systemic lupus erythematosus (SLE); inflammatory diseases of the heart such as cardiomyopathy, ischemic heart disease, hypercholesterolemia, and atherosclerosis; as well as various other diseases that can have significant inflammatory components, including preeclampsia, chronic liver failure, brain and spinal cord trauma and multiple organ dysfunction syndrome (MODS) (multiple organ failure (MOF)). The inflammatory disease can also be a systemic inflammation of the body, exemplified by gram-positive or gram negative shock, hemorrhagic or anaphylactic shock, or shock induced by cancer chemotherapy in response to pro-inflammatory cytokines, e.g., shock associated with pro-inflammatory cytokines. Such shock can be induced, e.g. by a chemotherapeutic agent that is administered as a treatment for cancer.

Thus, the present invention provides a compound of formula I for use in the manufacture of a medicament for treating or preventing inflammatory diseases.

The present invention also provides a method for the treatment or prevention of inflammatory diseases, which method comprises administration to a patient in need thereof of an effective amount of a compound of formula I or a composition comprising a compound of formula I.

The compounds of the instant invention may also be useful in the treatment or prevention of reperfusion injuries, resulting from naturally occurring episodes and during a surgical procedure, such as intestinal reperfusion injury; myocardial reperfusion injury; reperfusion injury resulting from cardiopulmonary bypass surgery, aortic aneurysm repair surgery, carotid endarterectomy surgery, or hemorrhagic shock; and reoxygenation injury resulting from transplantation of organs such as heart, lung, liver, kidney, pancreas, intestine, and cornea.

Thus, the present invention provides a compound of formula I for use in the manufacture of a medicament for the treatment or prevention of reperfusion injuries.

The present invention also provides a method for the treatment or prevention of reperfusion injuries, which method comprises administration to a patient in need thereof of an effective amount of a compound of formula I or a composition comprising a compound of formula I.

The compounds of the instant invention may also be useful in the treatment or prevention of ischemic conditions, including those resulting from organ transplantation, such as stable angina, unstable angina, myocardial ischemia, hepatic ischemia, mesenteric artery ischemia, intestinal ischemia, critical limb ischemia, chronic critical limb ischemia, cerebral ischemia, acute cardiac ischemia, ischemia kidney disease, ischemic liver disease, ischemic retinal disorder, septic shock, and an ischemic disease of the central nervous system, such as stroke or cerebral ischemia.

Thus, the present invention provides a compound of formula I for use in the manufacture of a medicament for the treatment or prevention of ischemic conditions.

The present invention also provides a method for the treatment or prevention of ischemic conditions, which method comprises administration to a patient in need thereof of an effective amount of a compound of formula I or a composition comprising a compound of formula I.

The present invention provides a compound of formula I for use in the manufacture of a medicament for the treatment or prevention of stroke.

The present invention also provides a method for the treatment or prevention of stroke, which method comprises administration to a patient in need thereof of an effective amount of a compound of formula I or a composition comprising a compound of formula I.

The compounds of the instant invention may also be useful for the treatment or prevention of chronic or acute renal failure.

Thus, the present invention provides a compound of formula I for use in the manufacture of a medicament for the treatment or prevention of renal failure.

The present invention also provides a method for the treatment or prevention of renal failure, which method comprises administration to a patient in need thereof of an effective amount of a compound of formula I or a composition comprising a compound of formula I.

The compounds of the instant invention may also be useful for the treatment or prevention of vascular diseases other than cardiovascular diseases, such as peripheral arterial occlusion, thromboangitis obliterans, Reynaud's disease and phenomenon, acrocyanosis, erythromelalgia, venous thrombosis, varicose veins, arteriovenous fistula, lymphedema and lipedema.

Thus, the present invention provides a compound of formula I for use in the manufacture of a medicament for the treatment or prevention of vascular diseases other than cardiovascular diseases.

The present invention also provides a method for the treatment or prevention of vascular diseases other than cardiovascular diseases, which method comprises administration to a patient in need thereof of an effective amount of a compound of formula I or a composition comprising a compound of formula I.

The compounds of the instant invention may also be useful for the treatment or prevention of cardiovascular diseases such as chronic heart failure, atherosclerosis, congestive heart failure, circulatory shock, cardiomyopathy, cardiac transplant, myocardialinfarction, and a cardiac arrhythmia, such as atrial fibrillation, supraventricular tachycardia, atrial flutter, and paroxysmal atrial tachycardia.

Thus, the present invention provides a compound of formula I for use in the manufacture of a medicament for the treatment or prevention of cardiovascular diseases.

The present invention also provides a method for the treatment or prevention of cardiovascular diseases, which method comprises administration to a patient in need thereof of an effective amount of a compound of formula I or a composition comprising a compound of formula I.

The compounds of this invention may also be useful for the treatment and prevention of diabetes mellitus, including Type I diabetes (Insulin Dependent Diabetes Mellitus), Type II diabetes (Non-Insulin Dependent Diabetes Mellitus), gestational diabetes, autoimmune diabetes, insulinopathies, diabetes due to pancreatic disease, diabetes associated with other endocrine diseases (such as Cushing's Syndrome, acromegaly, pheochromocytoma, glucagonoma, primary aldosteronism or somatostatinoma), Type A insulin resistance syndrome, Type B insulin resistance syndrome, lipatrophic diabetes, and diabetes induced by (3-cell toxins. The compounds of this invention may also be useful for the treatment or prevention of diabetic complications, such as diabetic cataract, glaucoma, retinopathy, nephropathy, (such asmicroaluminuria and progressive diabetic nephropathy), polyneuropathy, gangrene of the feet, atherosclerotic coronary arterial disease, peripheral arterial disease, nonketotic hyperglycemic-hyperosmolar coma, mononeuropathies, autonomic neuropathy, foot ulcers, joint problems, and a skin or mucous membrane complication (such as an infection, a shin spot, a candidal infection or necrobiosis lipoidica diabeticorumobesity), hyperlipidemia, hypertension, syndrome of insulin resistance, coronary artery disease, retinopathy, diabetic neuropathy, polyneuropathy, mononeuropathies, autonomic neuropathy, a foot ulcer, a joint problem, a fungal infection, a bacterial infection, and cardiomyopathy.

Thus, the present invention provides a compound of formula I for use in the manufacture of a medicament for the treatment or prevention of diabetes.

The present invention also provides a method for the treatment or prevention of diabetes, which method comprises administration to a patient in need thereof of an effective amount of a compound of formula I or a composition comprising a compound of formula I.

The compounds of this invention may also be useful for the treatment or prevention of cancer including solid tumors such as fibrosarcoma, myxo sarcoma, liposarcoma, chondrosarcoma, osteogenic sarcoma, chordoma, angiosarcoma, endothelio sarcoma, lymphangiosarcoma, lymphangioendothelio sarcoma, synovioma, mesothelioma, Ewing's tumor, leiomyosarcoma, rhabdomyo sarcoma, colon cancer, colorectal cancer, kidney cancer, pancreatic cancer, bone cancer, breast cancer, ovarian cancer, prostate cancer, esophageal cancer, stomach cancer, oral cancer, nasal cancer, throat cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, uterine cancer, testicular cancer, small cell lung carcinoma, bladder carcinoma, lung cancer, epithelial carcinoma, skin cancer, melanoma, neuroblastoma and retinoblastoma; blood-borne cancers such as acute lymphoblastic leukemia ("ALL"), acute lymphoblastic B-cell leukemia, acute lymphoblastic T-cell leukemia, acute myeloblastic leukemia ("AML"), acute promyelocytic leukemia ("APL"), acute monoblastic leukemia, acute erythroleukemic leukemia, acute megakaryoblastic leukemia, acute myelomonocytic leukemia, acute nonlymphocytic leukemia, acute undifferentiated leukemia, chronic myelocytic leukemia ("CML"), chronic lymphocytic leukemia ("CLL"), hairy cell leukemia and multiple myeloma; acute and chronic leukemias such as lymphoblastic, myelogenous, lymphocytic, myelocytic leukemias; Lymphomas such as Hodgkin's disease, non-Hodgkin's Lymphoma, Multiple myeloma, Waldenstrom's macroglobulinemia, Heavy chain disease and Polycythemia vera; CNS and brain cancers such as glioma, pilocytic astrocytoma, astrocytoma, anaplastic astrocytoma, glioblastoma multiforme, medulloblastoma, craniopharyngioma, ependymoma, pinealoma, hemangioblastoma, acoustic neuroma, oligodendroglioma, meningioma, vestibular schwannoma, adenoma, metastatic brain tumor, meningioma, spinal tumor and medulloblastoma.

Thus, the present invention provides a compound of formula I for use in the manufacture of a medicament for the treatment or prevention of cancer.

The present invention also provides a method for the treatment or prevention of cancer, which method comprises administration to a patient in need thereof of an effective amount of a compound of formula I or a composition comprising a compound of formula I.

The compounds of the present invention may also be used for the treatment of cancer which is deficient in Homologous Recombination (HR) dependent DNA DSB repair activity (see WO 2006/021801).

The HR dependent DNA DSB repair pathway repairs double-strand breaks (DSBs) in DNA via homologous mechanisms to reform a continuous DNA helix (*Nat. Genet.* (2001) 27(3):247-254). The components of the HR dependent DNA DSB repair pathway include, but are not limited to, ATM (NM-000051), RAD51 (NM-002875), RAD51 L1 (NM-002877), RAD51C (NM-002876), RAD51L3 (NM-002878), DMC1 (NM-007068), XRCC2 (NM7005431), XRCC3 (NM-005432), RAD52 (NM-002879), RAD54L (NM-003579), RAD54B (NM-012415), BRCA-1 (NM-007295), BRCA-2 (NM-000059), RAD50 (NM-005732), MREI 1A (NM-005590), NBS1 (NM-002485), ADPRT (PARP-1), ADPRTL2 (PARP-2), CTPS, RPA, RPA1, RPA2, RPA3, XPD, ERCC1, XPF, MMS19, RAD51p, RAD51D, DMC1, XRCCR, RAD50, MRE11, NB51, WRN, BLMKU70, RU80, ATRCHK1, CHK2, FANCA, FANCB, FANCC, FANCD1, FANCD2, FANCE, FANCF, FANCG, RAD1 and RAD9. Other proteins involved in the HR dependent DNA DSB repair pathway include regulatory factors such as EMSY (*Cell* (2003) 115:523-535).

A cancer which is deficient in HR dependent DNA DSB repair may comprise or consist of one or more cancer cells which have a reduced or abrogated ability to repair DNA DSBs through that pathway, relative to normal cells i.e. the activity of the HR dependent DNA DSB repair pathway may be reduced or abolished in the one or more cancer cells.

The activity of one or more components of the HR dependent DNA DSB repair pathway may be abolished in the one or more cancer cells of an individual having a cancer which is deficient in HR dependent DNA DSB repair. Components of the HR dependent DNA DSB repair pathway are well characterized in the art (see for example, *Science* (2001) 291: 1284-1289) and include the components listed above.

The present invention provides a compound of formula I for use in the manufacture of a medicament for the treatment or prevention of a cancer which is deficient in HR dependent DNA DSB repair activity.

The present invention also provides a method for the treatment or prevention of a cancer which is deficient in HR dependent DNA DSB repair activity, which method comprises administration to a patient in need thereof of an effective amount of a compound of formula I or a composition comprising a compound of formula I In an embodiment the cancer cells are deficient in the HR dependent DNA DSB repair activity of one or more phenotypes selected from ATM (NM-000051), RAD51 (NM-002875), RAD51 L1 (NM-002877), RAD51C (NM-002876), RAD51L3 (NM-002878), DMC1 (NM-007068), XRCC2 (NM7005431), XRCC3 (NM-005432), RAD52 (NM-002879), RAD54L (NM-003579), RAD54B (NM-012415), BRCA-1 (NM-007295), BRCA-2 (NM-000059), RAD5O (NM-005732), MREI 1A (NM-005590), NBS1 (NM-002485), ADPRT (PARP-1), ADPRTL2 (PARP-2), CTPS, RPA, RPA1, RPA2, RPA3, XPD, ERCC1, XPF, MMS19, RAD51p, RAD51D, DMC1, XRCCR, RAD50, MRE11, NB51, WRN, BLMKU70, RU80, ATRCHK1, CHK2, FANCA, FANCB, FANCC, FANCD1, FANCD2, FANCE, FANCF, FANCG, RAD1 and RAD9.

In another embodiment, the cancer cells have a BRCA1 and/or a BRCA2 deficient phenotype. Cancer cells with this phenotype may be deficient in BRCA1 and/or BRCA2, i.e. expression and/or activity of BRCA1 and/or BRCA2 may be reduced or abolished in the cancer cells, for example by means of mutation or polymorphism in the encoding nucleic acid, or by means of amplification, mutation or polymorphism in a gene encoding a regulatory factor, for example the EMSY gene which encodes a BRCA2 regulatory factor (*Cell* (2003) 115:523-535).

BRCA-1 and BRCA-2 are known tumor suppressors whose wild-type alleles are frequently lost in tumors of heterozygous carriers (*Oncogene*, (2002) 21(58):8981-93; *Trends Mol Med.*, (2002) 8(12):571-6). The association of BRCA-1 and/or BRCA-2 mutations with breast cancer has been well-characterized (*Exp Clin Cancer Res.*, (2002) 21 (3 Suppl):9-12). Amplification of the EMSY gene, which encodes a BRCA-2 binding factor, is also known to be associated with breast and ovarian cancer. Carriers of mutations in BRCA-1 and/or BRCA-2 are also at elevated risk of cancer of the ovary, prostate and pancreas. The detection of variation in BRCA-1 and BRCA-2 is well-known in the art and is described, for example in EP 699 754, EP 705 903, *Genet. Test* (1992) 1:75-83; *Cancer Treat Res* (2002) 107:29-59; *Neoplasm* (2003) 50(4):246-50; *Ceska Gynekol* (2003) 68(1): 11-16). Determination of amplification of the BRCA-2 binding factor EMSY is described in *Cell* 115:523-535. PARP inhibitors have been demonstrated as being useful for the specific killing of BRCA-1 and BRCA-2 deficient tumors (*Nature* (2005) 434:913-916 and 917-920).

Thus, the present invention provides a compound of formula I for use in the manufacture of a medicament for the treatment or prevention of BRCA-1 or BRCA-2 deficient tumors.

The present invention also provides a method for the treatment or prevention of BRCA-1 or BRCA-2 deficient tumors, which method comprises administration to a patient in need thereof of an effective amount of a compound of formula I or a composition comprising a compound of formula I.

In an embodiment, the PARP inhibitors of the present can be used in prophylactic therapy for elimination of BRCA2-deficient cells (see, *Cancer Res*. (2005) 65:10145).

The compounds of this invention may be useful for the treatment or prevention of neurodegenerative diseases, including, polyglutamine-expansion-related neurodegeneration, Huntington's disease, Kennedy's disease, spinocerebellar ataxia, dentatorubral-pallidoluysian atrophy (DRPLA), protein-aggregation-related neurodegeneration, Machado-Joseph's disease, Alzheimer's disease, Parkinson's disease, amyotrophic lateral sclerosis, spongiform encephalopathy, a prion-related disease and multiple sclerosis (MS).

Thus, the present invention provides a compound of formula I for use in the manufacture of a medicament for treating or preventing neurodegenerative diseases.

The present invention also provides a method for treating or preventing neurodegenerative diseases, which method comprises administration to a patient in need thereof of an effective amount of a compound of formula I or a composition comprising a compound of formula I.

The compounds of the present invention may also be useful for the treatment or prevention of retroviral infection (U.S. Pat. No. 5,652,260), retinal damage (*Curr. Eye Res.* (2004), 29:403), skin senescence and UV-induced skin damage (U.S. Pat. No. 5,589,483 and *Biochem. Pharmacol* (2002) 63:921).

The compounds of the invention are useful for the treatment or prevention of premature aging and postponing the onset of age-related cellular dysfunction (*Pharmacological Research* (2005) 52:93-99).

The compounds of this invention may be administered to mammals, preferably humans, either alone or in combination with pharmaceutically acceptable carriers, excipients, diluents, adjuvants, fillers, buffers, stabilisers, preservatives, lubricants, in a pharmaceutical composition, according to standard pharmaceutical practice.

The compounds of this invention may be administered to a subject by any convenient route of administration, whether systemically/peripherally or at the site of desired action, including but not limited to, oral (e.g. by ingestion); topical (including e.g. transdermal, intranasal, ocular, buccal, and sublingual); pulmonary (e.g. by inhalation or insufflation therapy using, e.g. an aerosol, e.g. through mouth or nose); rectal; vaginal; parenteral, (e.g. by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal); and by implant of a depot (e.g. subcutaneously or intramuscularly).

The subject may be a eukaryote, an animal, a vertebrate animal, a mammal, a rodent (e.g. a guinea pig, a hamster, a rat, a mouse), murine (e.g. a mouse), canine (e.g. a dog), feline (e.g. a cat), equine (e.g. a horse), a primate, simian (e.g. a monkey or ape), a monkey (e.g. marmoset, baboon), an ape (e.g. gorilla, chimpanzee, orangutang, gibbon), or a human.

The invention also provides pharmaceutical compositions comprising one or more compounds of this invention and a pharmaceutically acceptable carrier. The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, microcrystalline cellulose, sodium crosscarmellose, corn starch, or alginic acid; binding agents, for example starch, gelatin, polyvinyl-pyrrolidone or acacia, and lubricating agents, for example, magnesium stearate, stearic acid or talc. The tablets may be uncoated or they may be coated by known techniques to mask the unpleasant taste of the drug or delay disintegration and absorption in the gastrointestinal tract and thereby provide a sustained action over a longer period. For example, a water soluble taste masking material such as hydroxypropyl-methylcellulose or hydroxypropylcellulose, or a time delay material such as ethyl cellulose, cellulose acetate butyrate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropylmethyl-cellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as butylated hydroxyanisol or alpha-tocopherol.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present. These compositions may be preserved by the addition of an anti-oxidant such as ascorbic acid.

The pharmaceutical compositions of the invention may also be in the form of an oil-in-water emulsions. The oily phase may be a vegetable oil, for example olive oil or arachis oil, or a mineral oil, for example liquid paraffin or mixtures of these. Suitable emulsifying agents may be naturally occurring phosphatides, for example soy bean lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening, flavoring agents, preservatives and antioxidants.

Syrups and elixirs may be formulated with sweetening agents, for example glycerol, propylene glycol, sorbitol or sucrose. Such formulations may also contain a demulcent, a preservative, flavoring and coloring agents and antioxidant.

The pharmaceutical compositions may be in the form of a sterile injectable aqueous solutions. Among the acceptable vehicles and solvents that may be employed are water, Ringer's solution and isotonic sodium chloride solution.

The sterile injectable preparation may also be a sterile injectable oil-in-water microemulsion where the active ingredient is dissolved in the oily phase. For example, the active ingredient may be first dissolved in a mixture of soybean oil and lecithin The oil solution then introduced into a water and glycerol mixture and processed to form a microemulation.

The injectable solutions or microemulsions may be introduced into a patient's blood stream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS™ model 5400 intravenous pump.

The pharmaceutical compositions may be in the form of a sterile injectable aqueous or oleagenous suspension for intramuscular and subcutaneous administration. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, for example as a solution in 1,3-butanediol. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of Formula I may also be administered in the form of suppositories for rectal administration of the drug.

These compositions can be prepared by mixing the drug with a suitable non-irritating excipient which is solid at ordinary temperatures but liquid at the rectal temperature and will therefore melt in the rectum to release the drug. Such materials include cocoa butter, glycerinated gelatin, hydrogenated vegetable oils, mixtures of polyethylene glycols of various molecular weights and fatty acid esters of polyethylene glycol.

For topical use, creams, ointments, jellies, solutions or suspensions, etc., containing the compound of Formula I are employed. (For purposes of this application, topical application shall include mouth washes and gargles.)

The compounds for the present invention can be administered in intranasal form via topical use of suitable intranasal vehicles and delivery devices, or via transdermal routes, using those forms of transdermal skin patches well known to those of ordinary skill in the art. To be administered in the form of a transdermal delivery system, the dosage administration will, of course, be continuous rather than intermittent throughout the dosage regimen. Compounds of the present invention may also be delivered as a suppository employing bases such as cocoa butter, glycerinated gelatin, hydrogenated vegetable oils, mixtures of polyethylene glycols of various molecular weights and fatty acid esters of polyethylene glycol.

When a compound according to this invention is administered into a subject, the selected dosage level will depend on a variety of factors including, but not limited to, the activity of the particular compound, the severity of the individuals symptoms, the route of administration, the time of administration, the rate of excretion of the compound, the duration of the treatment, other drugs, compounds, and/or materials used in combination, and the age, sex, weight, condition, general health, and prior medical history of the patient. The amount of compound and route of administration will ultimately be at the discretion of the physician, although generally the dosage will be to achieve local concentrations at the site of action which achieve the desired effect without causing substantial harmful or deleterious side-effects.

Administration in vivo can be effected in one dose, continuously or intermittently (e.g. in divided doses at appropriate intervals) throughout the course of treatment. Methods of determining the most effective means and dosage of administration are well known to those of skill in the art and will vary with the formulation used for therapy, the purpose of the therapy, the target cell being treated, and the subject being treated. Single or multiple administrations can be carried out with the dose level and pattern being selected by the treating physician.

In general, a suitable dose of the active compound is in the range of about 100 µg to about 250 mg per kilogram body weight of the subject per day. Where the active compound is a salt, an ester, prodrug, or the like, the amount administered is calculated on the basis of the parent compound and so the actual weight to be used is increased proportionately.

The instant compounds are also useful in combination with anti-cancer agents or chemotherapeutic agents.

The compounds of this invention may be useful as chemo- and radiosensitizers for cancer treatment. They are useful for the treatment of mammals who have previously undergone or are presently undergoing treatment for cancer. Such previous treatments include prior chemotherapy, radiation therapy, surgery or immunotherapy, such as cancer vaccines.

Thus, the present invention provides a combination of a compound of formula I and an anti-cancer agent for simultaneous, separate or sequential administration.

The present invention also provides a compound of formula I for use in the manufacture of a medicament for use as an adjunct in cancer therapy or for potentiating tumor cells for treatment with ionizing radiation or chemotherapeutic agents.

The present invention also provides a method of chemotherapy or radiotherapy, which method comprises administration to a patient in need thereof of an effective amount of a compound of formula I or a composition comprising a compound of formula I in combination with ionizing radiation or chemotherapeutic agents.

In combination therapy, the compounds of this invention can be administered prior to (e.g., 5 minutes, 15 minutes, 30 minutes, 45 minutes, 1 hour, 2 hours, 4 hours, 6 hours, 12 hours, 24 hours, 48, hours, 72 hours, 96 hours, 1 week, 2 weeks, 3 weeks, 4 weeks, 5 weeks, 6 weeks, 8 weeks, or 12 weeks before), concurrently with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of the other anticancer agent to a subject in need thereof. In various embodiments the instant compounds and another anticancer agent are administered 1 minute apart, 10 minutes apart, 30 minutes apart, less than 1 hour apart, 1 hour to 2 hours apart, 2 hours to 3 hours apart, 3 hours to 4 hours apart, 4 hours to 5 hours apart, 5 hours to 6 hours apart, 6 hours to 7 hours apart, 7 hours to 8 hours apart, 8 hours to 9 hours apart, 9 hours to 10 hours apart, 10 hours to 11 hours apart, 11 hours to 12 hours apart, no more than 24 hours apart, or no more than 48 hours apart.

The compounds of this invention and the other anticancer agent can act additively or synergistically. A synergistic combination of the present compounds and another anticancer agent might allow the use of lower dosages of one or both of these agents and/or less frequent dosages of one or both of the instant compounds and other anticancer agents and/or to administer the agents less frequently can reduce any toxicity associated with the administration of the agents to a subject without reducing the efficacy of the agents in the treatment of cancer. In addition, a synergistic effect might result in the improved efficacy of these agents in the treatment of cancer and/or the reduction of any adverse or unwanted side effects associated with the use of either agent alone.

Examples of cancer agents or chemotherapeutic agents for use in combination with the compounds of the present invention can be found in *Cancer Principles and Practice of Oncology* by V. T. Devita and S. Hellman (editors), 6$^{th}$ edition (Feb. 15, 2001), Lippincott Williams & Wilkins Publishers. A person of ordinary skill in the art would be able to discern which combinations of agents would be useful based on the particular characteristics of the drugs and the cancer involved. Such anti-cancer agents include, but are not limited to, the following: HDAC inhibitors, estrogen receptor modulators, androgen receptor modulators, retinoid receptor modulators, cytotoxic/cytostatic agents, antiproliferative agents, prenyl-protein transferase inhibitors, HMG-CoA reductase inhibitors, HIV protease inhibitors, reverse transcriptase inhibitors and other angiogenesis inhibitors, inhibitors of cell proliferation and survival signaling, apoptosis inducing agents and agents that interfere with cell cycle checkpoints. The instant compounds are particularly useful when co-administered with radiation therapy.

Examples of "HDAC inhibitors" include suberoylanilide hydroxamic acid (SAHA), LAQ824, LBH589, PXD101, MS275, FK228, valproic acid, butyric acid and CI-994.

"Estrogen receptor modulators" refers to compounds that interfere with or inhibit the binding of estrogen to the receptor, regardless of mechanism. Examples of estrogen receptor modulators include, but are not limited to, tamoxifen, raloxifene, idoxifene, LY353381, LY117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]-phenyl-2,2-dimethylpropanoate, 4,4'-dihydroxybenzophenone-2,4-dinitrophenyl-hydrazone, and SH646.

"Androgen receptor modulators" refers to compounds which interfere or inhibit the binding of androgens to the receptor, regardless of mechanism. Examples of androgen receptor modulators include finasteride and other 5α-reductase inhibitors, nilutamide, flutamide, bicalutamide, liarozole, and abiraterone acetate.

"Retinoid receptor modulators" refers to compounds which interfere or inhibit the binding of retinoids to the receptor, regardless of mechanism. Examples of such retinoid receptor modulators include bexarotene, tretinoin, 13-cis-retinoic acid, 9-cis-retinoic acid, α-difluoromethylornithine, ILX23-7553, trans-N-(4'-hydroxyphenyl) retinamide, and N-4-carboxyphenyl retinamide.

"Cytotoxic/cytostatic agents" refer to compounds which cause cell death or inhibit cell proliferation primarily by interfering directly with the cell's functioning or inhibit or interfere with cell mytosis, including alkylating agents, tumor necrosis factors, intercalators, hypoxia activatable compounds, microtubule inhibitors/microtubule-stabilizing agents, inhibitors of mitotic kinesins, inhibitors of kinases involved in mitotic progression, antimetabolites, biological response modifiers; hormonal/anti-hormonal therapeutic agents, haematopoietic growth factors, monoclonal antibody targeted therapeutic agents, topoisomerase inhibitors, proteasome inhibitors and ubiquitin ligase inhibitors.

Examples of cytotoxic agents include, but are not limited to, cyclophosphamide, chlorambucil carmustine (BCNU), lomustine (CCNU), busulfan, treosulfan, sertenef, cachectin, ifosfamide, tasonermin, lonidamine, carboplatin, altretamine, prednimustine, dibromodulcitol, ranimustine, fotemustine, nedaplatin, aroplatin, oxaliplatin, temozolomide, methyl methanesulfonate, procarbazine, dacarbazine, heptaplatin, estramustine, improsulfan tosilate, trofosfamide, nimustine, dibrospidium chloride, pumitepa, lobaplatin, satraplatin, profiromycin, cisplatin, irofulven, dexifosfamide, cis-aminedichloro(2-methyl-pyridine)platinum, benzylguanine, glufosfamide, GPX100, (trans, trans, trans)-bis-mu-(hexane-1,6-diamine)-mu-[diamine-platinum(II)]bis[diamine(chloro)platinum (II)]tetrachloride, diarizidinylspermine, arsenic trioxide, 1-(11-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, doxorubicin, epirubicin, pirarubicin, antineoplaston, 3'-deamino-3'-morpholino-13-deoxo-10-hydroxycarminomycin, annamycin, galarubicin, elinafide, MEN10755 and 4-demethoxy-3-deamino-3-aziridinyl-4-methylsulphonyl-daunorubicin (see WO 00/50032).

In an embodiment the compounds of this invention can be used in combination with alkylating agents.

Examples of alkylating agents include but are not limited to, nitrogen mustards: cyclophosphamide, ifosfamide, trofosfamide and chlorambucil; nitrosoureas: carmustine (BCNU) and lomustine (CCNU); alkylsulphonates: busulfan and treosulfan; triazenes: dacarbazine, procarbazine and temozolomide; platinum containing complexes: cisplatin, carboplatin, aroplatin and oxaliplatin.

In an embodiment, the alkylating agent is dacarbazine. Dacarbazine can be administered to a subject at dosages ranging from about 150 mg/m2 (of a subject's body surface area) to about 250 mg/m2. In another embodiment, dacarbazine is administered intravenously to a subject once per day for five consecutive days at a dose ranging from about 150 mg/m2 to about 250 mg/m2.

In an embodiment, the alkylating agent is procarbazine. Procarbazine can be administered to a subject at dosages ranging from about 50 mg/m2 (of a subject's body surface area) to about 100 mg/m2. In another embodiment, procarbazine is administered intravenously to a subject once per day for five consecutive days at a dose ranging from about 50 mg/m2 to about 100 mg/m2.

In an embodiment, the alkylating agent is temozoloamide. Temozolomide can be administered to a subject at dosages ranging from about about 150 mg/m2 (of a subject's body surface area) to about 200 mg/m2. In another embodiment, temozolomide is administered orally to an animal once per day for five consecutive days at a dose ranging from about 150 mg/m2 to about 200 mg/m2.

Examples of anti-mitotic agents include: allocolchicine, halichondrin B, colchicine, colchicine derivative, dolstatin 10, maytansine, rhizoxin, thiocolchicine and trityl cysteine.

An example of a hypoxia activatable compound is tirapazamine.

Examples of proteasome inhibitors include but are not limited to lactacystin, bortezomib, epoxomicin and peptide aldehydes such as MG 132, MG 115 and PSI.

Examples of microtubule inhibitors/microtubule-stabilising agents include paclitaxel, vindesine sulfate, vincristine, vinblastine, vinorelbine, 3',4'-didehydro-4'-deoxy-8'-norvincaleukoblastine, docetaxol, rhizoxin, dolastatin, mivobulin isethionate, auristatin, cemadotin, RPR109881, BMS184476, vinflunine, cryptophycin, 2,3,4,5,6-pentafluoro-N-(3-fluoro-4-methoxyphenyl) benzene sulfonamide, anhydrovinblastine, N,N-dimethyl-1-valyl-1-valyl-N-methyl-1-valyl-1-prolyl-1-proline-t-butylamide, TDX258, the epothilones (see for example U.S. Pat. Nos. 6,284,781 and 6,288,237) and BMS188797.

Some examples of topoisomerase inhibitors are topotecan, hycaptamine, irinotecan, rubitecan, exatecan, gimetecan, diflomotecan, silyl-camptothecins, 9-aminocamptothecin, camptothecin, crisnatol, mitomycin C, 6-ethoxypropionyl-3',4'-O-exo-benzylidene-chartreusin, 9-methoxy-N,N-dimethyl-5-nitropyrazolo[3,4,5-kl]acridine-2-(6H) propanamine, 1-amino-9-ethyl-5-fluoro-2,3-dihydro-9-hydroxy-4-methyl-1H,12H-benzo[de]pyrano[3',4':b,7]-indolizino[1,2b]quinoline-10,13(9H,15H)dione, lurtotecan, 7-[2-(N-isopropylamino)ethyl]-(20S)camptothecin, BNP1350, BNPI1100, BN80915, BN80942, etoposide phosphate, teniposide, sobuzoxane, 2'-dimethylamino-2'-deoxy-etoposide, GL331, N-[2-(dimethylamino)ethyl]-9-hydroxy-5,6-dimethyl-6H-pyrido[4,3-b]carbazole-1-carboxamide, asulacrine, (5a, 5aB, 8aa,9b)-9-[2-[N-[2-(dimethylamino)ethyl]-N-methylamino]ethyl]-5-[4-hydroxy-3,5-dimethoxyphenyl]-5,5a,6,8,8a,9-hexohydrofuro(3',4':6,7) naphtho(2,3-d)-1,3-dioxol-6-one, 2,3-(methylenedioxy)-5-methyl-7-hydroxy-8-methoxybenzo[c]-phenanthridinium, 6,9-bis[(2-aminoethyl)amino]benzo[g]isoguinoline-5,10-dione, 5-(3-aminopropylamino)-7,10-dihydroxy-2-(2-hydroxyethylaminomethyl)-6H-pyrazolo[4,5,1-de]acridin-6-one, N-[1-[2(diethylamino)ethylamino]-7-methoxy-9-oxo-9H-thioxanthen-4-ylmethyl]formamide, N-(2-(dimethylamino)ethyl)acridine-4-carboxamide, 6-[[2-(dimethylamino)ethyl]amino]-3-hydroxy-7H-indeno[2,1-c]

quinolin-7-one, and dimesna; non-camptothecin topoisomerase-1 inhibitors such as indolocarbazoles; and dual topoisomerase-1 and II inhibitors such as benzophenazines, XR 20 115761MLN 576 and benzopyridoindoles.

In an embodiment, the topoisomerase inhibitor is irinotecan. Irinotecan can be administered to a subject at dosages ranging from about about 50 mg/m2 (of a subject's body surface area) to about 150 mg/m2. In another embodiment, irinotecan is administered intravenously to a subject once per day for five consecutive days at a dose ranging from about 50 mg/m2 to about 150 mg/m2 on days 1-5, then again intravenously once per day for five consecutive days on days 28-32 at a dose ranging from about 50 mg/m2 to about 150 mg/m2, then again intravenously once per day for five consecutive days on days 55-59 at a dose ranging from about 50 mg/m2 to about 150 mg/m2.

Examples of inhibitors of mitotic kinesins, and in particular the human mitotic kinesin KSP, are described in PCT Publications WO 01/30768, WO 01/98278, WO 02/056880, WO 03/050,064, WO 03/050,122, WO 03/049,527, WO 03/049,679, WO 03/049,678, WO 03/039460, WO 03/079973, WO 03/099211, WO 2004/039774, WO 03/105855, WO 03/106417, WO 2004/087050, WO 2004/058700, WO 2004/058148 and WO 2004/037171 and US applications US 2004/132830 and US 2004/132719. In an embodiment inhibitors of mitotic kinesins include, but are not limited to inhibitors of KSP, inhibitors of MKLP1, inhibitors of CENP-E, inhibitors of MCAK, inhibitors of Kif14, inhibitors of Mphosph1 and inhibitors of Rab6-KIFL.

"Inhibitors of kinases involved in mitotic progression" include, but are not limited to, inhibitors of aurora kinase, inhibitors of Polo-like kinases (PLK) (in particular inhibitors of PLK-1), inhibitors of bub-1 and inhibitors of bub-R1.

"Antiproliferative agents" includes antisense RNA and DNA oligonucleotides such as G3139, ODN698, RVASK-RAS, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N-[5-(2,3-dihydrobenzofuryl)sulfonyl]-N'-(3,4-dichlorophenyl)urea, N6-[4-deoxy-4-[N2-[2(E),4(E)-tetradecadienoyl]glycylamino]-1-glycero-B-1-manno-heptopyranosyl]adenine, aplidine, ecteinascidin, troxacitabine, 4-[2-amino-4-oxo-4,6,7,8-tetrahydro-3H-pyrimidino[5,4-b][1,4]thiazin-6-yl-(S)-ethyl]-2,5-thienoyl-1-glutamic acid, aminopterin, 5-flurouracil, alanosine, 11-acetyl-8-(carbamoyloxymethyl)-4-formyl-6-methoxy-14-oxa-1,11-diazatetracyclo(7.4.1.0.0)-tetradeca-2,4,6-trien-9-yl acetic acid ester, swainsonine, lometrexol, dexrazoxane, methioninase, 2'-cyano-2'-deoxy-N4-palmitoyl-1-B-D-arabino furanosyl cytosine and 3-aminopyridine-2-carboxaldehyde thiosemicarbazone.

Examples of monoclonal antibody targeted therapeutic agents include those therapeutic agents which have cytotoxic agents or radioisotopes attached to a cancer cell specific or target cell specific monoclonal antibody. Examples include Bexxar.

"HMG-CoA reductase inhibitors" refers to inhibitors of 3-hydroxy-3-methylglutaryl-CoA reductase. Examples of HMG-CoA reductase inhibitors that may be used include but are not limited to lovastatin (MEVACOR®); see U.S. Pat. Nos. 4,231,938, 4,294,926 and 4,319,039), simvastatin (ZOCOR®; see U.S. Pat. Nos. 4,444,784, 4,820,850 and 4,916, 239), pravastatin (PRAVACHOL®; see U.S. Pat. Nos. 4,346, 227, 4,537,859, 4,410,629, 5,030,447 and 5,180,589), fluvastatin (LESCOL®; see U.S. Pat. Nos. 5,354,772, 4,911, 165, 4,929,437, 5,189,164, 5,118,853, 5,290,946 and 5,356, 896) and atorvastatin (LIPITOR®; see U.S. Pat. Nos. 5,273, 995, 4,681,893, 5,489,691 and 5,342,952). The structural formulas of these and additional HMG-CoA reductase inhibitors that may be used in the instant methods are described at page 87 of M. Yalpani, "Cholesterol Lowering Drugs", Chemistry & Industry, pp. 85-89 (5 Feb. 1996) and U.S. Pat. Nos. 4,782,084 and 4,885,314. The term HMG-CoA reductase inhibitor as used herein includes all pharmaceutically acceptable lactone and open-acid forms (i.e., where the lactone ring is opened to form the free acid) as well as salt and ester forms of compounds which have HMG-CoA reductase inhibitory activity, and therefore the use of such salts, esters, open-acid and lactone forms is included within the scope of this invention.

"Prenyl-protein transferase inhibitor" refers to a compound which inhibits any one or any combination of the prenyl-protein transferase enzymes, including farnesyl-protein transferase (FPTase), geranylgeranyl-protein transferase type I (GGPTase-I), and geranylgeranyl-protein transferase type-II (GGPTase-II, also called Rab GGPTase).

Examples of prenyl-protein transferase inhibitors can be found in the following publications and patents: WO 96/30343, WO 97/18813, WO 97/21701, WO 97/23478, WO 97/38665, WO 98/28980, WO 98/29119, WO 95/32987, U.S. Pat. No. 5,420,245, U.S. Pat. No. 5,523,430, U.S. Pat. No. 5,532,359, U.S. Pat. No. 5,510,510, U.S. Pat. No. 5,589,485, U.S. Pat. No. 5,602,098, European Patent Publ. 0 618 221, European Patent Publ. 0 675 112, European Patent Publ. 0 604 181, European Patent Publ. 0 696 593, WO 94/19357, WO 95/08542, WO 95/11917, WO 95/12612, WO 95/12572, WO 95/10514, U.S. Pat. No. 5,661,152, WO 95/10515, WO 95/10516, WO 95/24612, WO 95/34535, WO 95/25086, WO 96/05529, WO 96/06138, WO 96/06193, WO 96/16443, WO 96/21701, WO 96/21456, WO 96/22278, WO 96/24611, WO 96/24612, WO 96/05168, WO 96/05169, WO 96/00736, U.S. Pat. No. 5,571,792, WO 96/17861, WO 96/33159, WO 96/34850, WO 96/34851, WO 96/30017, WO 96/30018, WO 96/30362, WO 96/30363, WO 96/31111, WO 96/31477, WO 96/31478, WO 96/31501, WO 97/00252, WO 97/03047, WO 97/03050, WO 97/04785, WO 97/02920, WO 97/17070, WO 97/23478, WO 97/26246, WO 97/30053, WO 97/44350, WO 98/02436, and U.S. Pat. No. 5,532,359. For an example of the role of a prenyl-protein transferase inhibitor on angiogenesis see European J. of Cancer (1999), 35(9):1394-1401.

"Angiogenesis inhibitors" refers to compounds that inhibit the formation of new blood vessels, regardless of mechanism. Examples of angiogenesis inhibitors include, but are not limited to, tyrosine kinase inhibitors, such as inhibitors of the tyrosine kinase receptors Flt-1 (VEGFR1) and Flk-1/KDR (VEGFR2), inhibitors of epidermal-derived, fibroblast-derived, or platelet derived growth factors, MMP (matrix metalloprotease) inhibitors, integrin blockers, interferon-a, interleukin-12, pentosan polysulfate, cyclooxygenase inhibitors, including nonsteroidal anti-inflammatories (NSAIDs) like aspirin and ibuprofen as well as selective cyclooxy-genase-2 inhibitors like celecoxib and rofecoxib (PNAS (1992) 89:7384; JNCI (1982) 69:475; Arch. Opthalmol. (1990) 108: 573; Anat. Rec. (1994) 238:68; FEBS Letters (1995) 372:83; Clin, Orthop. (1995) 313:76; J. Mol. Endocrinol. (1996) 16:107; Jpn. J. Pharmacol. (1997) 75:105; Cancer Res. (1997) 57:1625 (1997); Cell (1998) 93:705; Intl. J. Mol. Med. (1998) 2:715; J. Biol. Chem. (1999) 274:9116)), steroidal anti-inflammatories (such as corticosteroids, mineralocorticoids, dexamethasone, prednisone, prednisolone, methylpred, betamethasone), carboxyamidotriazole, combretastatin A-4, squalamine, 6-O-chloroacetyl-carbonyl)-fumagillol, thalidomide, angiostatin, troponin-1, angiotensin II antagonists (see *J. Lab. Clin. Med.* (1985) 105:141-145), and antibodies to VEGF (see *Nature Biotechnology* (1999) 17:963-968; Kim et al (1993) *Nature* 362:841-844; WO 00/44777; and WO 00/61186).

Other therapeutic agents that modulate or inhibit angiogenesis and may also be used in combination with the compounds of the instant invention include agents that modulate or inhibit the coagulation and fibrinolysis systems (see review in *Clin. Chem. La. Med.* (2000) 38:679-692). Examples of such agents that modulate or inhibit the coagulation and fibrinolysis pathways include, but are not limited to, heparin (see *Thromb. Haemost.* (1998) 80:10-23), low molecular weight heparins and carboxypeptidase U inhibitors (also known as inhibitors of active thrombin activatable fibrinolysis inhibitor [TAFIa]) (see *Thrombosis Res.* (2001) 101:329-354). TAFIa inhibitors have been described in PCT Publication WO 03/013,526 and U.S. Ser. No. 60/349,925 (filed Jan. 18, 2002).

"Agents that interfere with cell cycle checkpoints" refer to compounds that inhibit protein kinases that transduce cell cycle checkpoint signals, thereby sensitizing the cancer cell to DNA damaging agents. Such agents include inhibitors of ATR, ATM, the Chk1 and Chk2 kinases and cdk and cdc kinase inhibitors and are specifically exemplified by 7-hydroxystaurosporin, staurosporin, flavopiridol, CYC202 (Cyclacel) and BMS-387032.

"Inhibitors of cell proliferation and survival signaling pathway" refer to pharmaceutical agents that inhibit cell surface receptors and signal transduction cascades downstream of those surface receptors. Such agents include inhibitors of inhibitors of EGFR (for example gefitinib and erlotinib), inhibitors of ERB-2 (for example trastuzumab), inhibitors of IGFR (for example those disclosed in WO 03/059951), inhibitors of cytokine receptors, inhibitors of MET, inhibitors of PI3K (for example LY294002), serine/threonine kinases (including but not limited to inhibitors of Akt such as described in (WO 03/086404, WO 03/086403, WO 03/086394, WO 03/086279, WO 02/083675, WO 02/083139, WO 02/083140 and WO 02/083138), inhibitors of Raf kinase (for example BAY-43-9006), inhibitors of MEK (for example CI-1040 and PD-098059) and inhibitors of mTOR (for example Wyeth CCI-779 and Ariad AP23573). Such agents include small molecule inhibitor compounds and antibody antagonists.

"Apoptosis inducing agents" include activators of TNF receptor family members (including the TRAIL receptors).

A compound of the instant invention may also be useful for treating cancer in combination with any one or more of the following therapeutic agents: abarelix (Plenaxis Depot®); aldesleukin (Prokine®); Aldesleukin (Proleukin®); Alemtuzumabb (Campath®); alitretinoin (Panretin®); allopurinol (Zyloprim®); altretamine (Hexalen®); amifostine (Ethyol®); anastrozole (Arimidex®); arsenic trioxide (Trisenox®); asparaginase (Elspar®); azacitidine (Vidaza®); bevacuzimab (Avastin®); bexarotene capsules (Targretin®); bexarotene gel (Targretin®); bleomycin (Blenoxane®); bortezomib (Velcade®); busulfan intravenous (Busulfex®); busulfan oral (Myleran®); calusterone (Methosarb®); capecitabine (Xeloda); carboplatin (Paraplatin®); carmustine (BCNU®, BiCNU®); carmustine (Gliadel®); carmustine with Polifeprosan 20 Implant (Gliadel Wafer®); celecoxib (Celebrex®); cetuximab (Erbitux); chlorambucil (Leukeran®); cisplatin (Platinol®); cladribine (Leustatin®, 2-CdA®); do farabine (Clolar®); cyclophosphamide (Cytoxan®, Neosar®); cyclophosphamide (Cytoxan Injection®); cyclophosphamide (Cytoxan Tablet®); cytarabine (Cytosar-U®); cytarabine liposomal (DepoCyt®); dacarbazine (DTIC-Dome®); dactinomycin, actinomycin D (Cosmegen®); Darbepoetin alfa (Aranesp®); daunorubicin liposomal (DanuoXome); daunorubicin, daunomycin (Daunorubicin®); daunorubicin, daunomycin (Cerubidine®); Denileukin diftitox (Ontak®); dexrazoxane (Zinecard®); docetaxel (Taxotere®); doxorubicin (Adriamycin PFS®); doxorubicin (Adriamycin®, Rubex®); doxorubicin (Adriamycin PFS Injection®); doxorubicin liposomal (Doxil®); dromostanolone propionate (Dromostanolone®); dromostanolone propionate (Masterone Injection®); Elliott's B Solution (Elliott's B Solution®); epirubicin (Ellence®); Epoetin alfa (Epogen®); erlotinib (Tarceva®); estramustine (Emcyt®); etoposide phosphate (Etopophos®); etoposide, VP-16 (Vepesid®); exemestane (Aromasin®); Filgrastim (Neupogen®); floxuridine (intraarterial) (FUDR®); fludarabine (Fludara®); fluorouracil, 5-FU (Adrucil®); fulvestrant (Faslodex®); gefitinib (Iressa®); gemcitabine (Gemzar®); gemtuzumab ozogamicin (Mylotarg®); goserelin acetate (Zoladex Implant®); goserelin acetate (Zoladex®); histrelin acetate (Histrelin Implant®); hydroxyurea (Hydrea®); Ibritumomab Tiuxetan (Zevalin®); idarubicin (Idamycin®); ifosfamide (IFEX®); imatinib mesylate (Gleevec®); interferon alfa 2a (Roferon A®); Interferon alfa-2b (Intron A®); irinotecan (Camptosar®); lenalidomide (Revlimid®); letrozole (Femara®); leucovorin (Wellcovorin®, Leucovorin®); Leuprolide Acetate (Eligard); levamisole (Ergamisol®); lomustine, CCNU (CeeBU); meclorethamine, nitrogen mustard (Mustargen®); megestrol acetate (Megace®); melphalan, L-PAM (Alkeran®); mercaptopurine, 6-MP (Purinethol®); mesna (Mesnex®); mesna (Mesnex Tabs®); methotrexate (Methotrexate®); methoxsalen (Uvadex®); mitomycin C (Mutamycin®); mitotane (Lysodren®); mitoxantrone (Novantrone®); nandrolone phenpropionate (Durabolin-50®); nelarabine (Arranon®); Nofetumomab (Verluma®); Oprelvekin (Neumega®); oxaliplatin (Eloxatin®); paclitaxel (Paxene®); paclitaxel (Taxol®); paclitaxel protein-bound particles (Abraxane®); palifermin (Kepivance®); pamidronate (Aredia®); pegademase (Adagen (Pegademase Bovine)®); pegaspargase (Oncaspar®); Pegfilgrastim (Neulasta®); pemetrexed disodium (Alimta®); pentostatin (Nipent®); pipobroman (Vercyte®); plicamycin, mithramycin (Mithracin®); porfimer sodium (Photofrin®); procarbazine (Matulane®); quinacrine (Atabrine®); Rasburicase (Elitek®); Rituximab (Rituxan®); sargramostim (Leukine®); Sargramostim (Prokine®); sorafenib (Nexavar®); streptozocin (Zanosar®); sunitinib maleate (Sutent®); talc (Sclerosol®); tamoxifen (Nolvadex®); temozolomide (Temodar®); teniposide, VM-26 (Vumon®); testolactone (Teslac®); thioguanine, 6-TG (Thioguanine®); thiotepa (Thioplex®); topotecan (Hycamtin®); toremifene (Fareston®); Tositumomab (Bexxar®); Tositumomab/I-131 tositumomab (Bexxar®); Trastuzumab (Herceptin®); tretinoin, ATRA (Vesanoid); Uracil Mustard (Uracil Mustard Capsules®); valrubicin (Valstar®); vinblastine (Velban®); vincristine (Oncovin®); vinorelbine (Navelbine®); vorinostat (Zolinza®); zoledronate (Zometa®); nilotinib (Tasigna®) and dasatinib (Sprycel®).

The invention also encompasses combinations with NSAID's which are selective COX-2 inhibitors. For purposes of this specification NSAID's which are selective inhibitors of COX-2 are defined as those which possess a specificity for inhibiting COX-2 over COX-1 of at least 100 fold as measured by the ratio of $IC_{50}$ for COX-2 over $IC_{50}$ for COX-1 evaluated by cell or microsomal assays. Such compounds include, but are not limited to those disclosed in U.S. Pat. No. 5,474,995, U.S. Pat. No. 5,861,419, U.S. Pat. No. 6,001,843, U.S. Pat. No. 6,020,343, U.S. Pat. No. 5,409,944, U.S. Pat. No. 5,436,265, U.S. Pat. No. 5,536,752, U.S. Pat. No. 5,550, 142, U.S. Pat. No. 5,604,260, U.S. Pat. No. 5,698,584, U.S. Pat. No. 5,710,140, WO 94/15932, U.S. Pat. No. 5,344,991, U.S. Pat. No. 5,134,142, U.S. Pat. No. 5,380,738, U.S. Pat. No. 5,393,790, U.S. Pat. No. 5,466,823, U.S. Pat. No. 5,633, 272, and U.S. Pat. No. 5,932,598, all of which are hereby incorporated by reference.

Inhibitors of COX-2 that are particularly useful in the instant method of treatment are 5-chloro-3-(4-methylsulfonyl)phenyl-2-(2-methyl-5-pyridinyl)pyridine; or a pharmaceutically acceptable salt thereof.

Compounds that have been described as specific inhibitors of COX-2 and are therefore useful in the present invention include, but are not limited to: parecoxib, CELEBREX® and BEXTRA® or a pharmaceutically acceptable salt thereof.

Other examples of angiogenesis inhibitors include, but are not limited to, endostatin, ukrain, ranpirnase, IM862, 5-methoxy-4-[2-methyl-3-(3-methyl-2-butenyl)oxiranyl]-1-oxaspiro[2,5]oct-6-yl(chloroacetyl)carbamate, acetyldinanaline, 5-amino-1-[[3,5-dichloro-4-(4-chlorobenzoyl)phenyl]methyl]-1H-1,2,3-triazole-4-carboxamide, CM101, squalamine, combretastatin, RPI4610, NX31838, sulfated mannopentaose phosphate, 7,7-(carbonyl-bis[imino-N-methyl-4,2-pyrrolocarbonylimino[N-methyl-4,2-pyrrole]-carbonylimino]-bis-(1,3-naphthalene disulfonate), and 3-[(2,4-dimethylpyrrol-5-yl)methylene]-2-indolinone (SU5416).

As used above, "integrin blockers" refers to compounds which selectively antagonize, inhibit or counteract binding of a physiological ligand to the $\alpha_v\beta_3$ integrin, to compounds which selectively antagonize, inhibit or counteract binding of a physiological ligand to the $\alpha_v\beta_5$ integrin, to compounds which antagonize, inhibit or counteract binding of a physiological ligand to both the $\alpha_v\beta_3$ integrin and the $\alpha_v\beta_5$ integrin, and to compounds which antagonize, inhibit or counteract the activity of the particular integrin(s) expressed on capillary endothelial cells. The term also refers to antagonists of the $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins. The term also refers to antagonists of any combination of $\alpha_v\beta_3$, $\alpha_v\beta_5$, $\alpha_v\beta_6$, $\alpha_v\beta_8$, $\alpha_1\beta_1$, $\alpha_2\beta_1$, $\beta_5\alpha_1$, $\alpha_6\beta_1$ and $\alpha_6\beta_4$ integrins.

Some specific examples of tyrosine kinase inhibitors include N-(trifluoromethylphenyl)-5-methylisoxazol-4-carboxamide, 3-[(2,4-dimethylpyrrol-5-yl)methylidenyl)indolin-2-one, 17-(allylamino)-17-demethoxygeldanamycin, 4-(3-chloro-4-fluorophenylamino)-7-methoxy-6-[3-(4-morpholinyl)propoxyl]quinazoline, N-(3-ethynylphenyl)-6,7-bis (2-methoxyethoxy)-4-quinazolinamine, BIBX1382, 2,3,9, 10,11,12-hexahydro-10-(hydroxymethyl)-10-hydroxy-9-methyl-9,12-epoxy-1H-diindolo[1,2,3-fg:3',2',1'-kl]pyrrolo [3,4-i][1,6]benzodiazocin-1-one, SH268, genistein, STI571, CEP2563, 4-(3-chlorophenylamino)-5,6-dimethyl-7H-pyrrolo[2,3-d]pyrimidinemethane sulfonate, 4-(3-bromo-4-hydroxyphenyl)amino-6,7-dimethoxyquinazoline, 4-(4'-hydroxyphenyl)amino-6,7-dimethoxyquinazoline, SU6668, STI571A, N-4-chlorophenyl-4-(4-pyridylmethyl)-1-phthalazinamine, and EMD 121974.

In an embodiment, the compounds of the present invention are useful for the treatment or prevention of the appearance of necrosis induced by selective N3-adenine methylating agents such as $MeOSO_2(CH_2)$-lexitropsin (Me-Lex).

Combinations with compounds other than anti-cancer compounds are also encompassed in the instant methods. For example, combinations of the instantly claimed compounds with PPAR-$\gamma$ (i.e., PPAR-gamma) agonists and PPAR-$\delta$ (i.e., PPAR-delta) agonists are useful in the treatment of certain malingnancies. PPAR-$\gamma$ and PPAR-$\delta$ are the nuclear peroxisome proliferator-activated receptors $\gamma$ and $\delta$. The expression of PPAR-$\gamma$ on endothelial cells and its involvement in angiogenesis has been reported in the literature (see *J. Cardiovasc. Pharmacol.* (1998) 31:909-913; *J. Biol. Chem.* (1999) 274: 9116-9121; *Invest. Ophthalmol Vis. Sci.* (2000) 41:2309-2317). More recently, PPAR-$\gamma$ agonists have been shown to inhibit the angiogenic response to VEGF in vitro; both troglitazone and rosiglitazone maleate inhibit the development of retinal neovascularization in mice. (*Arch. Ophthamol.* (2001) 119:709-717). Examples of PPAR-$\gamma$ agonists and PPAR-$\gamma/\alpha$ agonists include, but are not limited to, thiazolidinediones (such as DRF2725, CS-011, troglitazone, rosiglitazone, and pioglitazone), fenofibrate, gemfibrozil, clofibrate, GW2570, SB219994, AR-H039242, JTT-501, MCC-555, GW2331, GW409544, NN2344, KRP297, NP0110, DRF4158, NN622, GI262570, PNU182716, DRF552926, 2-[(5,7-dipropyl-3-trifluoromethyl-1,2-benzisoxazol-6-yl)oxy]-2-methylpropionic acid (disclosed in U.S. Ser. No. 09/782,856), and 2(R)-7-(3-(2-chloro-4-(4-fluorophenoxy)phenoxy)propoxy)-2-ethylchromane-2-carboxylic acid (disclosed in U.S. Ser. No. 60/235,708 and 60/244,697).

Another embodiment of the instant invention is the use of the presently disclosed compounds in combination with antiviral agents (such as nucleoside analogs including ganciclovir for the treatment of cancer. See WO 98/04290.

Another embodiment of the instant invention is the use of the presently disclosed compounds in combination with gene therapy for the treatment of cancer. For an overview of genetic strategies to treating cancer see Hall et al (*Am J Hum Genet* (1997) 61:785-789) and Kufe et al (*Cancer Medicine,* 5th Ed, pp 876-889, B C Decker, Hamilton 2000). Gene therapy can be used to deliver any tumor suppressing gene. Examples of such genes include, but are not limited to, p53, which can be delivered via recombinant virus-mediated gene transfer (see U.S. Pat. No. 6,069,134, for example), a uPA/uPAR antagonist ("Adenovirus-Mediated Delivery of a uPA/uPAR Antagonist Suppresses Angiogenesis-Dependent Tumor Growth and Dissemination in Mice," *Gene Therapy*, August (1998) 5(8):1105-13), and interferon gamma (*J Immunol* (2000) 164:217-222).

The compounds of the instant invention may also be administered in combination with an inhibitor of inherent multidrug resistance (MDR), in particular MDR associated with high levels of expression of transporter proteins. Such MDR inhibitors include inhibitors of p-glycoprotein (P-gp), such as LY335979, XR9576, OC144-093, R101922, VX853, verapamil and PSC833 (valspodar).

A compound of the present invention may be employed in conjunction with anti-emetic agents to treat nausea or emesis, including acute, delayed, late-phase, and anticipatory emesis, which may result from the use of a compound of the present invention, alone or with radiation therapy. For the prevention or treatment of emesis, a compound of the present invention may be used in conjunction with other anti-emetic agents, especially neurokinin-1 receptor antagonists, 5HT3 receptor antagonists, such as ondansetron, granisetron, tropisetron, and zatisetron, GABA$_B$ receptor agonists, such as baclofen, a corticosteroid such as Decadron (dexamethasone), Kenalog, Aristocort, Nasalide, Preferid, Benecorten or others such as disclosed in U.S. Pat. Nos. 2,789,118, 2,990,401, 3,048,581, 3,126,375, 3,929,768, 3,996,359, 3,928,326 and 3,749,712, an antidopaminergic, such as the phenothiazines (for example prochlorperazine, fluphenazine, thioridazine and mesoridazine), metoclopramide or dronabinol. In an embodiment, an anti-emesis agent selected from a neurokinin-1 receptor antagonist, a 5HT3 receptor antagonist and a corticosteroid is administered as an adjuvant for the treatment or prevention of emesis that may result upon administration of the instant compounds.

Neurokinin-1 receptor antagonists of use in conjunction with the compounds of the present invention are fully described, for example, in U.S. Pat. Nos. 5,162,339, 5,232, 929, 5,242,930, 5,373,003, 5,387,595, 5,459,270, 5,494,926, 5,496,833, 5,637,699, 5,719,147; European Patent Publication Nos. EP 0 360 390, 0 394 989, 0 428 434, 0 429 366, 0 430 771, 0 436 334, 0 443 132, 0 482 539, 0 498 069, 0 499 313, 0 512 901, 0 512 902, 0 514 273, 0 514 274, 0 514 275, 0 514 276, 0 515 681, 0 517 589, 0 520 555, 0 522 808, 0 528 495, 0 532 456, 0 533 280, 0 536 817, 0 545 478, 0 558 156, 0 577 394, 0 585 913, 0 590 152, 0 599 538, 0 610 793, 0 634 402, 0 686 629, 0 693 489, 0 694 535, 0 699 655, 0 699 674, 0 707 006, 0 708 101, 0 709 375, 0 709 376, 0 714 891, 0 723 959, 0 733 632 and 0 776 893; PCT International Patent Publication Nos. WO 90/05525, 90/05729, 91/09844, 91/18899, 92/01688, 92/06079, 92/12151, 92/15585, 92/17449, 92/20661, 92/20676, 92/21677, 92/22569, 93/00330, 93/00331, 93/01159, 93/01165, 93/01169, 93/01170, 93/06099, 93/09116, 93/10073, 93/14084, 93/14113, 93/18023, 93/19064, 93/21155, 93/21181, 93/23380, 93/24465, 94/00440, 94/01402, 94/02461, 94/02595, 94/03429, 94/03445, 94/04494, 94/04496, 94/05625, 94/07843, 94/08997, 94/10165, 94/10167, 94/10168, 94/10170, 94/11368, 94/13639, 94/13663, 94/14767, 94/15903, 94/19320, 94/19323, 94/20500, 94/26735, 94/26740, 94/29309, 95/02595, 95/04040, 95/04042, 95/06645, 95/07886, 95/07908, 95/08549, 95/11880, 95/14017, 95/15311, 95/16679, 95/17382, 95/18124, 95/18129, 95/19344, 95/20575, 95/21819, 95/22525, 95/23798, 95/26338, 95/28418, 95/30674, 95/30687, 95/33744, 96/05181, 96/05193, 96/05203, 96/06094, 96/07649, 96/10562, 96/16939, 96/18643, 96/20197, 96/21661, 96/29304, 96/29317, 96/29326, 96/29328, 96/31214, 96/32385, 96/37489, 97/01553, 97/01554, 97/03066, 97/08144, 97/14671, 97/17362, 97/18206, 97/19084, 97/19942 and 97/21702; and in British Patent Publication Nos. 2 266 529, 2 268 931, 2 269 170, 2 269 590, 2 271 774, 2 292 144, 2 293 168, 2 293 169, and 2 302 689. The preparation of such compounds is fully described in the aforementioned patents and publications, which are incorporated herein by reference.

In an embodiment, the neurokinin-1 receptor antagonist for use in conjunction with the compounds of the present invention is selected from: 2-(R)-(1-(R)-(3,5-bis(trifluoromethyl)phenyl)ethoxy)-3-(S)-(4-fluorophenyl)-4-(3-(5-oxo-1H,4H-1,2,4-triazolo)methyl)morpholine, or a pharmaceutically acceptable salt thereof, which is described in U.S. Pat. No. 5,719,147.

A compound of the instant invention may also be administered with an agent useful in the treatment of anemia. Such an anemia treatment agent is, for example, a continuous eythropoiesis receptor activator (such as epoetin alfa).

A compound of the instant invention may also be administered with an agent useful in the treatment of neutropenia. Such a neutropenia treatment agent is, for example, a hematopoietic growth factor which regulates the production and function of neutrophils such as a human granulocyte colony stimulating factor, (G-CSF). Examples of a G-CSF include filgrastim.

A compound of the instant invention may also be administered with an immunologic-enhancing drug, such as levamisole, isoprinosine and Zadaxin.

A compound of the instant invention may also be useful for treating or preventing cancer, including bone cancer, in combination with bisphosphonates (understood to include bisphosphonates, diphosphonates, bisphosphonic acids and diphosphonic acids). Examples of bisphosphonates include but are not limited to: etidronate (Didronel), pamidronate (Aredia), alendronate (Fosamax), risedronate (Actonel), zoledronate (Zometa), ibandronate (Boniva), incadronate or cimadronate, clodronate, EB-1053, minodronate, neridronate, piridronate and tiludronate including any and all pharmaceutically acceptable salts, derivatives, hydrates and mixtures thereof.

Thus, the scope of the instant invention encompasses the use of the instantly claimed compounds in combination with ionizing radiation and/or in combination with a second compound selected from: HDAC inhibitors, an estrogen receptor modulator, an androgen receptor modulator, retinoid receptor modulator, a cytotoxic/cytostatic agent, an antiproliferative agent, a prenyl-protein transferase inhibitor, an HMG-CoA reductase inhibitor, an angiogenesis inhibitor, a PPAR-γ agonist, a PPAR-δ agonist, an anti-viral agent, an inhibitor of inherent multidrug resistance, an anti-emetic agent, an agent useful in the treatment of anemia, an agent useful in the treatment of neutropenia, an immunologic-enhancing drug, an inhibitor of cell proliferation and survival signaling, an agent that interfers with a cell cycle checkpoint, an apoptosis inducing agent and a bisphosphonate.

The term "administration" and variants thereof (e.g., "administering" a compound) in reference to a compound of the invention means introducing the compound or a prodrug of the compound into the system of the animal in need of treatment. When a compound of the invention or prodrug thereof is provided in combination with one or more other active agents (e.g., a cytotoxic agent, etc.), "administration" and its variants are each understood to include concurrent and sequential introduction of the compound or prodrug thereof and other agents.

As used herein, the term "composition" is intended to encompass a product comprising the specified ingredients in the specified amounts, as well as any product which results, directly or indirectly, from combination of the specified ingredients in the specified amounts.

The term "therapeutically effective amount" as used herein means that amount of active compound or pharmaceutical agent that elicits the biological or medicinal response in a tissue, system, animal or human that is being sought by a researcher, veterinarian, medical doctor or other clinician.

The term "treatment" refers to the treatment of a mammal afflicted with a pathological condition and refers to an effect that alleviates the condition by killing the cancerous cells, but also to an effect that results in the inhibition of the progress of the condition, and includes a reduction in the rate of progress, a halt in the rate of progress, amelioration of the condition, and cure of the condition. Treatment as a prophylactic measure (i.e. prophylaxis) is also included.

The term "pharmaceutically acceptable" as used herein pertains to compounds, materials, compositions, and/or dosage forms which are, within the scope of sound medical judgement, suitable for use in contact with the tissues of a subject (e.g. human) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation.

The term "adjunct" refers to the use of compounds in conjunction with known therapeutic means. Such means include cytotoxic regimes of drugs and/or ionising radiation as used in the treatment of different cancer types. In particular, the active compounds are known to potentiate the actions of a number of cancer chemotherapy treatments, which include the topoisomerase class of poisons (e.g. topotecan, irinotecan, rubitecan), most of the known alkylating agents (e.g. DTIC, temozolamide) and platinum based drugs (e.g. carboplatin, cisplatin) used in treating cancer.

In an embodiment, the angiogenesis inhibitor to be used as the second compound is selected from a tyrosine kinase inhibitor, an inhibitor of epidermal-derived growth factor, an inhibitor of fibroblast-derived growth factor, an inhibitor of platelet derived growth factor, an MMP (matrix metalloprotease) inhibitor, an integrin blocker, interferon-α, interleukin-12, pentosan polysulfate, a cyclooxygenase inhibitor, carboxyamidotriazole, combretastatin A-4, squalamine, 6-O-chloroacetyl-carbonyl)-fumagillol, thalidomide, angiostatin, troponin-1, or an antibody to VEGF. In an embodiment, the estrogen receptor modulator is tamoxifen or raloxifene.

Also included in the scope of the claims is a method of treating cancer that comprises administering a therapeutically effective amount of a compound of Formula I in combination with radiation therapy and/or in combination with a compound selected from: HDAC inhibitors, an estrogen receptor modulator, an androgen receptor modulator, retinoid receptor modulator, a cytotoxic/cytostatic agent, an antiproliferative agent, a prenyl-protein transferase inhibitor, an HMG-CoA reductase inhibitor, an angiogenesis inhibitor, a PPAR-γ agonist, a PPAR-δ agonist, an anti-viral agent, an inhibitor of inherent multidrug resistance, an anti-emetic agent, an agent useful in the treatment of anemia, an agent useful in the treatment of neutropenia, an immunologic-enhancing drug, an inhibitor of cell proliferation and survival signaling, an agent that interfers with a cell cycle checkpoint, an apoptosis inducing agent and a bisphosphonate.

And yet another embodiment of the invention is a method of treating cancer that comprises administering a therapeutically effective amount of a compound of Formula I in combination with paclitaxel or trastuzumab.

The invention further encompasses a method of treating or preventing cancer that comprises administering a therapeutically effective amount of a compound of Formula I in combination with a COX-2 inhibitor.

The instant invention also includes a pharmaceutical composition useful for treating or preventing cancer that comprises a therapeutically effective amount of a compound of Formula I and a compound selected from: HDAC inhibitors, an estrogen receptor modulator, an androgen receptor modulator, a retinoid receptor modulator, a cytotoxic/cytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, a PPAR-γ agonist, a PPAR-δ agonist, an anti-viral agent, an inhibitor of cell proliferation and survival signaling, an agent that interfers with a cell cycle checkpoint, an apoptosis inducing agent and a bisphosphonate.

These and other aspects of the invention will be apparent from the teachings contained herein.

Abbreviations Used in the Description of the Chemistry and in the Examples that Follow Are:

ACN (acetonitrile); Boc(tert-butoxycarbonyl); DCM (dichloromethane); DIPEA (diisopropylethylamine); DMF (dimethylformamide); EtOAc (ethyl acetate); H$_2$O (water); LiOH (lithium hydroxide); MeOH (methanol); RT (room temperature); TBTU (O-benzotriazol-1-yl-N,N,N',N'-tetramethyluronium tetrafluoroborate); TEA (triethylamine); TFA (trifluoroacetic acid); and THF (tetrahydrofuran).

Compounds of formula I can be prepared by condensation of a compound of formula IA with a compound of formula IB:

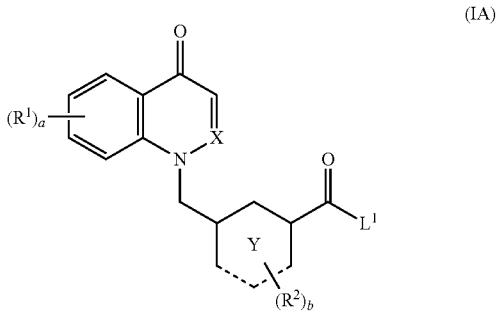

(IA)

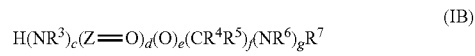

(IB)

wherein a, b, c, d, e, f, g, R$^1$, R$^2$, R$^3$, R$^4$, R$^5$, R$^6$, R$^7$, X, Y and Z are as defined above and L$^1$ is a leaving group such as hydroxy. The reaction is generally carried out in the presence of one or more coupling agents such as TBTU, HBTU and TEA, in a solvent such as DMF at about RT. The coupling agents HATU, HOBt and DIPEA may also be used at about 50° C.

Compounds of formula IA wherein L$^1$ is hydroxy can be prepared by hydrolysis of a compound of formula ID:

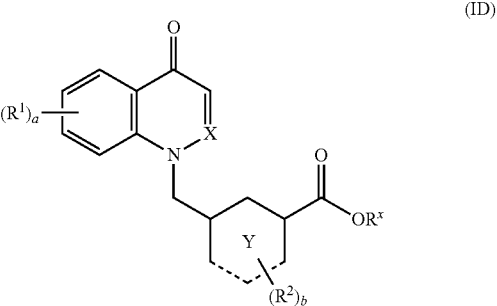

(ID)

wherein a, b, R$^1$, R$^2$, X and Y are as defined above and R$^x$ is C$_{1-6}$alkyl, for example methyl. Standard hydrolysis conditions can be used, such as the use of a strong base such as LiOH, in solvents such as THF and water at about RT.

Compounds of formula ID can be prepared by condensation of a compound of formula IE with a compound of formula IF:

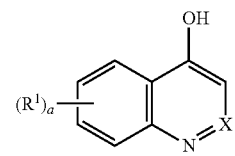

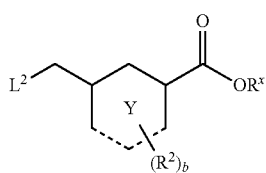

wherein a, b, $R^1$, $R^2$, X, Y and $R^x$ are as defined above and $L^2$ is a leaving group such as halogen, for example bromine. The reaction is generally carried out in the presence of a base such as $K_2CO_3$, in a solvent such as DMF at about 100° C.

Alternatively, compounds of formula ID can be prepared by condensation of a compound of formula IF with a compound of formula IG:

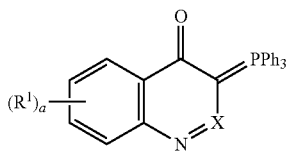

wherein a, $R^1$ and X are as defined above, generally in a solvent such as ACN at reflux. Subsequent hydrolysis is then carried out, using standard hydrolying conditions such as a strong base such as NaOH, in a solvent such as water at about RT.

Compounds of formula IG wherein X is N can be prepared by cyclization of a compound of formula 1H:

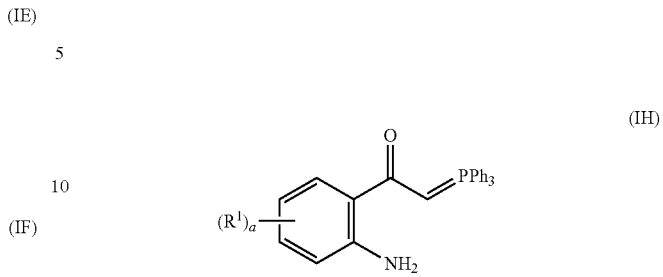

wherein a and $R^1$ are as defined above, firstly in the presence of a nitrosation reagent such as $NOBF_4$, in a solvent such as DCM at about 0° C., followed by the addition of a base such as NaOH at about RT. The nitrosation reagent isoamyl nitrite may also be used, generally in solvents such as HCl and MeOH at about 0° C.

Where the synthesis of intermediates and starting materials is not described, these compounds are commercially available or can be made from commercially available compounds by standard methods or by extension of the chemistry described in the synthesis, schemes and Examples herein.

Compounds of formula I may be converted to other compounds of formula I by known methods or by methods described in the Examples.

During any of the synthetic sequences described herein it may be necessary and/or desirable to protect sensitive or reactive groups on any of the molecules concerned. This may be achieved by means of conventional protecting groups, such as those described in *Protecting Groups in Organic Synthesis*, 3rd Edition, Greene, T. W. and Wuts, P. G. M.; Wiley Interscience, 1999 and Kocienski, P. J. *Protecting Groups*, Thieme, 1994. The protecting groups may be removed at a convenient subsequent stage using methods known from the art. For example, when the Boc group is present, it may be removed by the addition of solvents such as TFA/DCM at about RT.

The compounds of this invention were prepared according to the following schemes. All variables within the formulae are as defined above.

Scheme 1

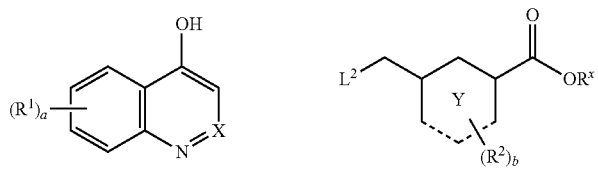

base, solvent
e.g. $K_2CO_3$
in DMF at 100° C.

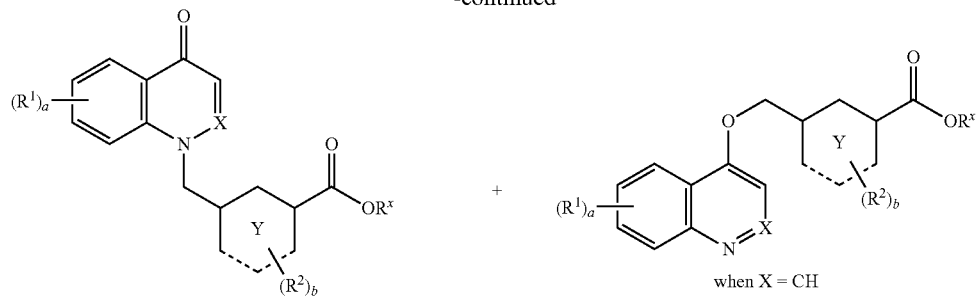

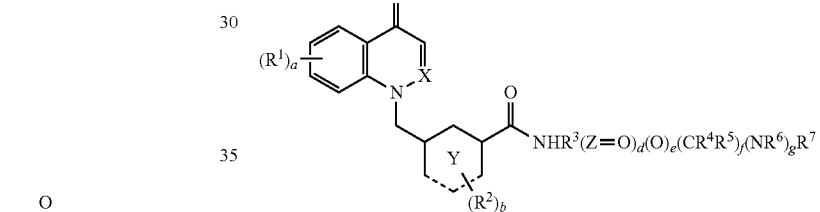

when X = N

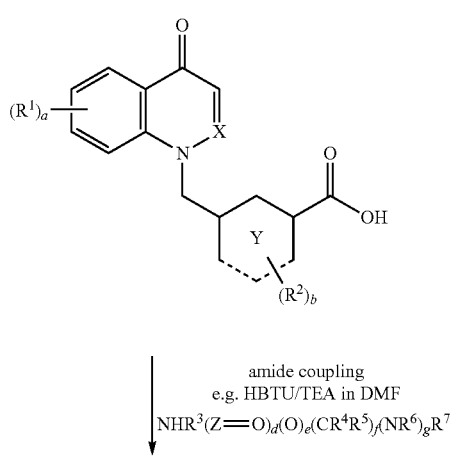

Scheme 2

The compounds of the present invention can be prepared according to the general Schemes 1 and 2:

4-Hydroxyquinolines or 4-hydroxycinnolines can be alkylated with alkylhalides to give a mixture of O- and N-alkylated products. Alkylation of 4-hydroxycinnolines gives a mixture of 1-alkyl-4-cinnolones and 2-alkylcinnolin-2-ium-4-olates. In both cases the two products can be separated by standard procedures like for example chromatography.

Analogs bearing an ester group on the pending benzyl ring can be hydrolyzed by standard procedures (scheme 2). The resulting carboxylic acid can be transformed into an amide by standard amide coupling reactions.

Scheme 3

Cinnolin-4(1H)-ones substituted in the aromatic ring can be prepared from substituted antranilic acids using the methodology described in *Synthesis* 1987, 288. After esterification of the carboxylic acid under standard procedure (e.g. HCl in MeOH at reflux) reaction with "in situ" formed methylenetriphenylphosphorane led to the formation of the triphenylphosphoniummethylides. These derivatives were cyclized to the cinnolinone ring by spontaneous intramolecular coupling in the presence of a base such as NaOH of the corresponding diazonium ions prepared by reaction with a nitrosation reagent such as $NOBF_4$ in DCM at 0° C. Selective alkylation of the cinnolinone ring in position 1 was performed in the presence of a suitable alkylating reagent in a solvent such as acetonitrile at reflux. Basic hydrolisis of the phosphorane and ester group was performed with a base such as NaOH in a solvent such as MeOH/water at RT as described in *Synthesis* 1986, 1059. The resulting carboxylic acid was transformed into an amide by standard amide coupling reactions using a coupling reagent such as TBTU, a base such as TEA in a solvent such as DMF at about RT.

Cinnolin-4(1H)-ones substituted in the aromatic ring with a hydroxy or methoxy group was prepared from the corresponding fluoro analogs (synthesized according to the procedure described in Scheme 3) by reaction with a suitable nucleophile (e.g. LiOH) under microwave irradiation in a solvent such as water. The resulting carboxylic acid was transformed into an amide by standard amide coupling reactions using a coupling reagent such as TBTU, a base such as TEA in a solvent such as DMF at about RT.

Scheme 4

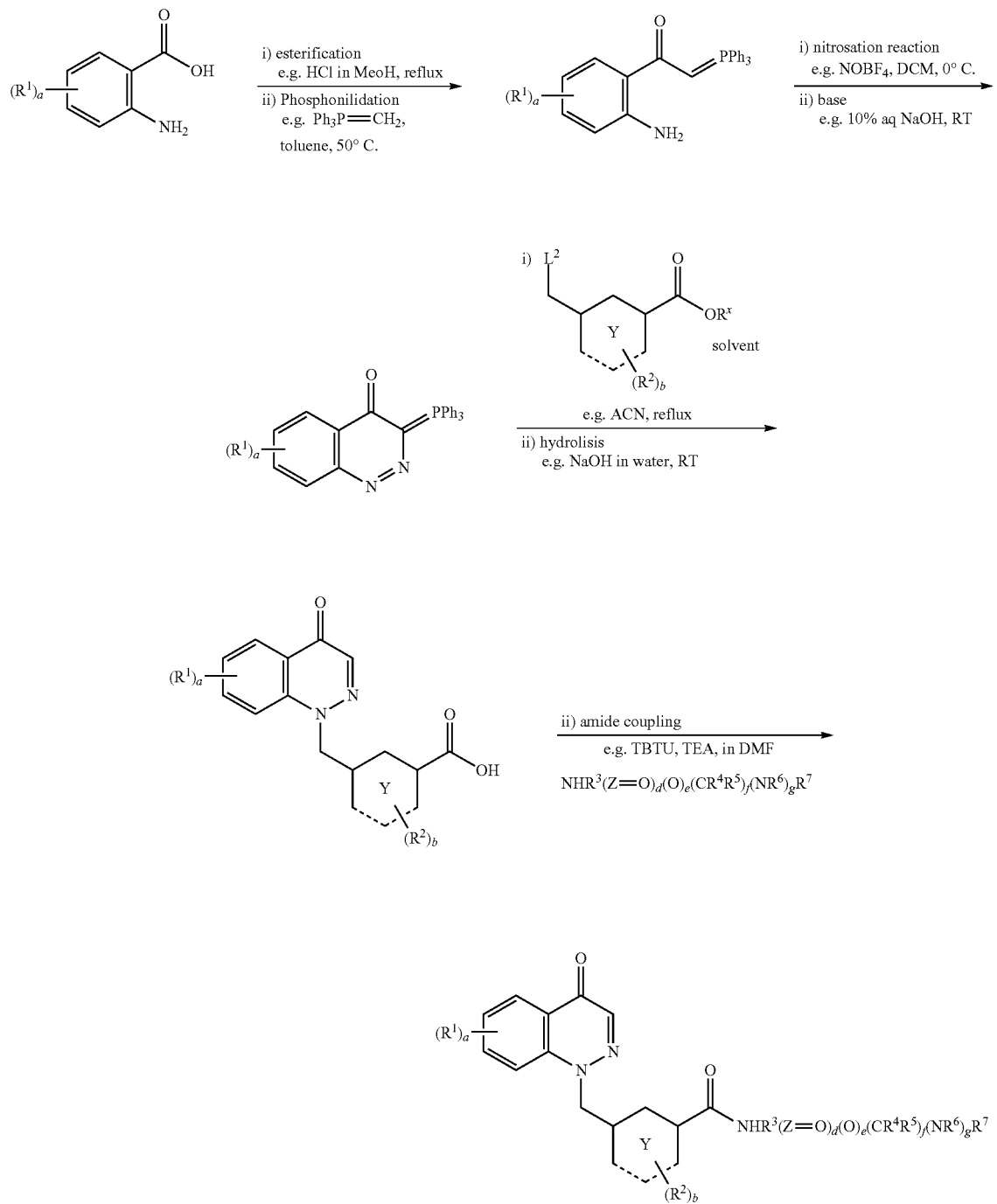

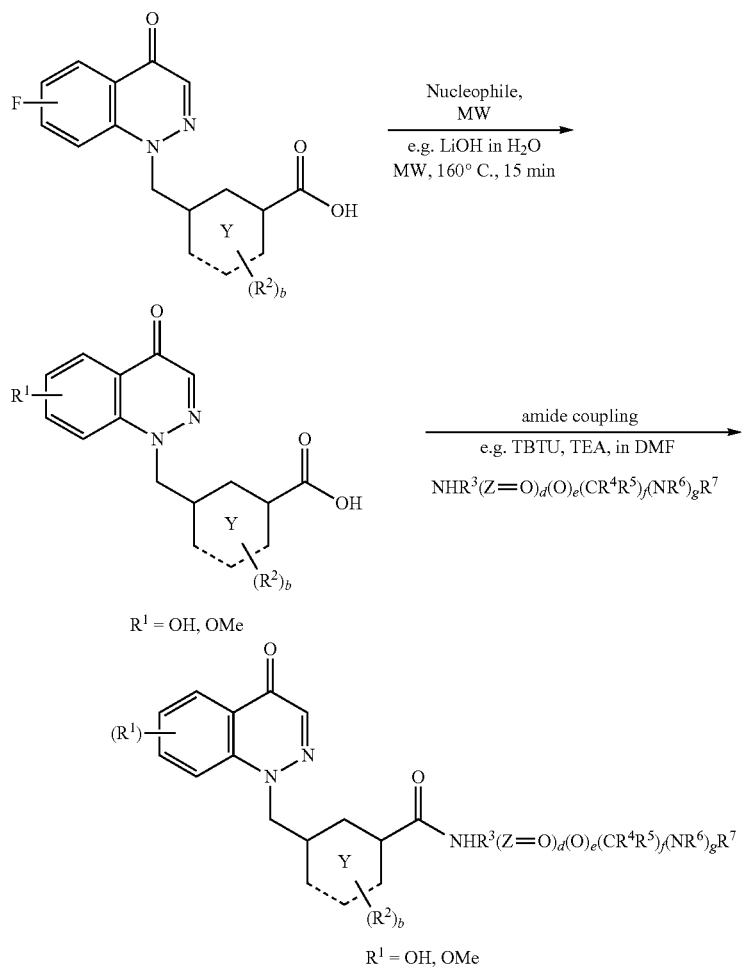

The exemplified compounds described herein were tested by the assays described below and were found to have an IC$_{50}$ value of less than 5 μM.

PARP-1 SPA Assay

Working Reagents

Assay buffer: 100 mM Tris pH 8, 4 mM MgCl$_2$, 4 mM Spermine, 200 mM KCl, 0.04% Nonidet P-40.

Enzyme Mix: Assay buffer (12.5 ul), 100 mM DTT (0.5 ul), PARP-1 (5 nM, Trevigen 4668-500-01), H$_2$O (to 35 ul).

Nicotinamide-adenine dinucleotide (NAD)/DNA Mix: [$^3$H-NAD] (250 uCi/ml, 0.4 ul, Perkin-Elmer NET-443H), NAD (1.5 mM, 0.05 ul, SIGMA N-1511), Biotinylated-NAD (250 uM, 0.03 ul, Trevigen 4670-500-01), Activated calf thymus (1 mg/ml, 0.05 ul, Amersham Biosciences 27-4575), H$_2$O (to 10 ul).

Developing Mix: Streptavidin SPA beads (5 mg/ml, Amersham Biosciences RPNQ 0007) dissolved in 500 mM EDTA.

Experimental Design

The reaction is performed in 96-well microplate with a final volume of 50 uL/well. Add 5 ul 5% DMSO/compound solution, add enzyme mix (35 ul), start the reaction by adding NAD/DNA mix (10 uL) and incubate for 2 hrs at RT. Stop the reaction by adding developing mix (25 ul) and incubate 15 min at RT. Measure using a Packard TOP COUNT instrument.

EXAMPLE 1

1-[3-(8-aza-1-azoniaspiro[4.5]dec-8-ylcarbonyl)-4-fluorobenzyl]-4-oxo-1,4-dihydroquinolinium bis(trifluoroacetate) (A3)

Step 1: Methyl 2-fluoro-5-[(4-oxoquinolin-1(4H)-yl)methyl]benzoate (A1)

A mixture of quinolin-4-ol, methyl 5-(bromomethyl)-2-fluorobenzoate (prepared as described in US 2007/0021427 A1, 1 eq) and potassium carbonate (1.2 eq) in dry DMF (0.1 M solution) was stirred at 100° C. for 1 h. After solvent evaporation, the residue was dissolved in DCM and washed twice with H$_2$O and once with brine. The organic phase was dried over Na$_2$SO$_4$ and concentrated to dryness under reduced pressure. The resulting crude was purified by flash-chromatography (EtOAc/PE 9:1) to give the title compound. The O-alkylated isomer is eluted before the title compound.

$^1$H NMR (400 MHz, DMSO-d$_6$) δ: 8.22 (1H, d, J=7.83 Hz), 8.20-8.13 (1H, m), 7.85-7.75 (1H, m), 7.67-7.54 (2H, m), 7.53-7.45 (1H, m), 7.41-7.28 (2H, m), 6.16 (1H, d, J=7.83 Hz), 5.57 (2H, s), 3.82 (3H, s). MS (ES) C$_{18}$H$_{14}$FNO$_3$ requires: 311, Found: 312 (M+H)$^+$.

Step 2: 1-(3-carboxy-4-fluorobenzyl)-4-oxo-1,4-dihydroquinolinium chloride (A2)

To a solution of A1 in THF (0.15 M) was added under stirring at 0° C. an aqueous solution of lithium hydroxide (0.7 M, 2 eq). The mixture was stirred at RT for 5 h. THF was removed under reduced pressure and the remaining aqueous solution was acidified to pH 1 with HCl 6N. The formed precipitate was filtered off and washed with water to afford the title compound as a white powder.

$^1$H NMR (300 MHz, DMSO-d$_6$) δ: 13.30 (1H, br.s), 8.28-8.12 (2H, m), 7.80-7.69 (1H, m), 7.68-7.54 (2H, m), 7.53-7.42 (1H, m), 7.41-7.22 (2H, m), 6.16 (1H, d, J=7.86 Hz), 5.56 (2H, s). MS (ES) C$_{17}$H$_{12}$FNO$_3$ requires: 297, Found: 298 (M+H)$^+$.

Step 3: 1-[3-(8-aza-1-azoniaspiro[4.5]dec-8-ylcarbonyl)-4-fluorobenzyl]-4-oxo-1,4-dihydroquinolinium bis(trifluoroacetate) (A3)

A solution of A2, HBTU (1 eq) and TEA (2 eq) in dry DMF (0.3 M) was stirred at RT for 5 minutes and then TEA (1 eq) and tent-butyl 1,8-diazaspiro[4.5]decane-1-carboxylate were added. The mixture was stirred at RT for 16 h. The product was purified by preparative RP-HPLC, using H$_2$O/ACN (0.1% TFA) as eluents. The pooled product fractions were lyophilized and the oily residue (A3) was treated with a DCM/TFA mixture (9:1) at 45° C. for 1 h. After removal of the solvents under reduced pressure the oily residue was lyophilized from H$_2$O/ACN to afford the title compound as a colourless oil.

$^1$H NMR (300 MHz, DMSO-d$_6$) δ: 8.70 (2H, br. s), 8.25 (1H, d, J=7.83 Hz), 8.22-8.14 (1H, m), 7.70-7.58 (2H, m), 7.44-7.35 (2H, m), 7.34-7.23 (2H, m), 6.20 (1H, d, J=7.86 Hz), 5.56 (2H, s), 3.38-3.19 (4H, m), 3.18-3.03 (1H, m), 2.07 (1H, m), 2.03-1.74 (6H, m), 1.69-1.57 (2H, m). MS (ES) C$_{25}$H$_{26}$FN$_3$O$_2$ requires: 419, Found: 420 (M+H)$^+$.

EXAMPLE 2

1-[4-fluoro-3-({4-[2-(4-fluorobenzyl)prolyl]piperazin-1-yl}carbonyl)benzyl]quinolin-4(1H)-one (B3)

Step 1: tert-butyl 4-{2-fluoro-5-[(4-oxoquinolin-1(4H)-yl)methyl]benzoyl}piperazine-1-carboxylate (B1)

To a stirred solution of Example 1, A2 in DMF (0.3 M) was added TEA (2.4 eq.) and TBTU (1.3 eq.). The mixture was stirred for 20 min and tent-butyl piperazine-1-carboxylate was added (1.5 eq.). After 1 h the mixture was diluted with EtOAc and washed with water, s.s. NaHCO$_3$ and brine. The organic phase was dried over Na$_2$SO$_4$, filtered and concentrated to dryness to afford the title compound as an orange foam.

$^1$H NMR (300 MHz, DMSO-d$_6$) δ: 8.22-8.12 (m, 2H), 7.68-7.53 (m, 2H), 7.41-7.22 (m, 4H), 6.15 (d, J=7.9 Hz, 1H), 5.53 (s, 2H), 3.58 (s, 2H), 3.37 (s, 2H), 3.19 (s, 2H), 3.10 (s, 2H), 1.40 (s, 9H). MS (ES) C$_{26}$H$_{28}$FN$_3$O$_4$ requires: 465, Found: 466 (M+H)$^+$.

Step 2: 1-[4-fluoro-3-(piperazin-1-ylcarbonyl)benzyl]quinolin-4(1H)-one (B2)

B1 from step 1 was stirred in a 1:1 mixture of DCM and TFA (0.1M) for 30 min. The solvents were removed under reduced pressure and the residue was dissolved in MeOH. The solution was applied on a SCX cation exchange resin, the resin was washed with H$_2$O and MeOH and the product was eluted with ammonia in MeOH (2N). The solvents were removed under reduced pressure to a afford the title compound as a beige solid.

$^1$H NMR (300 MHz, DMSO-d$_6$) δ: 8.22-8.11 (m, 2H), 7.67-7.54 (m, 2H), 7.36-7.18 (m, 4H), 6.14 (d, J=7.7 Hz, 1H), 5.53 (s, 2H), 3.52 (s, 2H), 3.30 (s, 2H), 2.75-2.64 (m, 2H), 2.60-2.52 (m, 2H). MS (ES) C$_{21}$H$_{20}$FN$_3$O$_2$ requires: 365, Found: 366 (M+H)$^+$.

Step 3: 11-[4-fluoro-3-({4-[2-(4-fluorobenzyl)prolyl]piperazin-1-yl}carbonyl)benzyl]quinolin-4(1H)-one (B3)

To a solution of 1-(tert-butoxycarbonyl)-2-(4-fluorobenzyl)proline (1.5 eq. resp. B2) in DMF (0.45 M) was added HATU (1.5 eq. resp. B2), HOBT (1.5 eq. resp. B2), and DIPEA (1.5 eq. resp. B2). The mixture was stirred at RT for 15 min and B2 was added (1 eq.). Stirring was continued for 16 h at 50° C. The product was purified by preparative RP-HPLC, using H$_2$O/ACN (0.1% TFA) as eluents. The pooled product fractions were concentrated under reduced pressure and the oily residue was dissolved in a 1:1 mixture of DCM and TFA. After 30 min the solvents were removed under reduced pressure. The resulting oil was dissolved in MeOH and the solution was applied on a SCX cation exchange resin. The resin was washed with H$_2$O and MeOH and the product was eluted with ammonia in MeOH (2N). The solvents were removed under reduced pressure and the residue was lyophilized from a 1:1 mixture of water/ACN to afford the title compound as an off-white powder.

$^1$H NMR (300 MHz, DMSO-d$_6$) δ: 8.23-8.12 (m, 2H), 7.67-7.52 (m, 2H), 7.40-7.24 (m, 4H), 7.22-7.18 (m, 2H), 7.10-7.01 (m, 2H), 6.15 (d, J=7.8 Hz, 1H), 5.54 (s, 2H), 4.05-3.50 (m, 6H), 3.16 (s, 2H), 3.03-2.80 (m, 3H), 2.72-2.61 (m, 1H), 2.20-1.95 (m, 1H), 1.90-1.72 (m, 1H), 1.67-1.50 (m, 2H). MS (ES) C$_{33}$H$_{32}$F$_2$N$_4$O$_3$ requires: 570, Found: 571 (M+H)$^+$.

EXAMPLE 3

1-[3-(8-aza-1-azoniaspiro[4.5]dec-8-ylcarbonyl)-4-fluorobenzyl]-4-oxo-1,4-dihydrocinnolin-1-ium bis(trifluoroacetate) (C3)

Step 1: methyl 2-fluoro-5-[(4-oxocinnolin-1(4H)-yl)methyl]benzoate (C1)

To a solution of cinnolin-4(1H)-one in DMF (0.1 M) was added K$_2$CO$_3$ (1.2 eq) and methyl 5-(bromomethyl)-2-fluorobenzoate (prepared as described in US 2007/0021427 A1, 1 eq). The mixture was stirred and heated to 100° C. for 1 h. After cooling to RT the solvent was removed under reduced pressure and the residue was partitioned between DCM and H$_2$O. The organic phase was washed with brine, dried (Na$_2$SO$_4$) and filtered and the solvent was removed under reduced pressure. The product was isolated by flash chromatography on silicagel, using a gradient of DCM/MeOH (from 0% to 10% MeOH in 10 CV). The 2-[4-fluoro-3-(methoxycarbonyl)benzyl]cinnolin-2-ium-4-olate was eluted after the title compound.

MS (ES) C$_{18}$H$_{13}$FN$_2$O$_3$ requires: 312, Found: 313 (M+H)$^-$.

Step 2: 1-(3-carboxy-4-fluorobenzyl)-4-oxo-1,4-dihydrocinnolin-1-ium chloride (C2)

To a stirred solution of C1 in THF (0.1 M) at RT was added a solution of LiOH in H$_2$O (2 eq, 0.7 M). After 2 h the THF was removed under reduced pressure and the remaining solution was acidified with HCl 6N. The formed precipitate was filtered off, washed with H$_2$O and left under high vacuum to afford the title compound as a beige powder.

$^1$H NMR (400 MHz, DMSO-d$_6$) δ: 13.33 (s, br, 1H), 8.18-8.10 (m, 1H), 7.87 (s, 1H), 7.86-7.74 (M, 3H), 7.56-7.44 (m, 2H), 7.30-7.24 (m, 1H), 5.76 (s, 2H).

MS (ES) C$_{16}$H$_{11}$FN$_2$O$_3$ requires: 298, Found: 299 (M+H)$^-$.

Step 3: 1-[3-(8-aza-1-azoniaspiro[4.5]dec-8-ylcarbonyl)-4-fluorobenzyl]-4-oxo-1,4-dihydrocinnolin-1-ium bis(trifluoroacetate) (C3)

To a stirred solution of C2 and TEA (1.2 eq) in DMF (0.3 M) was added TBTU (1.3 eq). The mixture was and stirred for 1h and tent-butyl 1,8-diazaspiro[4.5]decane-1-carboxylate together with TEA (4 eq) was added. The mixture was stirred for 2 h and the product was purified by preparative RP-HPLC, using H$_2$O/ACN (0.1% TFA) as eluents. The pooled fraction were concentrated under reduced pressure and the remaining oil was (C3) stirred for 30 min in a mixture of TFA/DCM (1:1). The solvents were removed under reduced pressure and the residue was lyophilized from H$_2$O/ACN. The title compound was obtained as a slightly orange foam.

$^1$H NMR (400 MHz, DMSO-d$_6$) δ: 8.65 (2H, br. s), 8.17-8.10 (1H, m), 7.86 (s, 1H), 7.84-7.75 (m, 2H), 7.52-7.41 (m, 2H), 7.36-7.25 (m, 2H), 5.74 (s, 2H), 4.10-3.99 (m, 1H), 3.31-3.07 (m, 5H), 2.00-1.72 (m, 6H), 1.69-1.60 (m, 2H). MS (ES) C$_{24}$H$_{25}$FN$_4$O$_2$ requires: 420, Found: 421 (M+H)$^+$.

The following Examples were prepared according to the procedures of the Examples above.

| Example | Name | MWt | [M + H]+ | Procedure of Example |
|---|---|---|---|---|
| 4 | 1-[3-(1,4-diazepan-1-ylcarbonyl)-4-fluorobenzyl]quinolin-4(1H)-one | 379 | 380 | 1 |
| 5 | 1-{4-fluoro-3-[(4-propionylpiperazin-1-yl)carbonyl]benzyl}quinolin-4(1H)-one | 421 | 422 | 1* |
| 6 | 1-(4-fluoro-3-{[3-(trifluoromethyl)-5,6-dihydro[1,2,4]triazolo[4,3-a]pyrazin-7(8H)-yl]carbonyl}benzyl)quinolin-4(1H)-one | 471 | 472 | 1* |
| 7 | 1-[3-(1,8-diazaspiro[4.5]dec-8-ylcarbonyl)-4-fluorobenzyl]quinolin-4(1H)-one | 419 | 420 | 1 |
| 8 | 1-[4-fluoro-3-(piperazin-1-ylcarbonyl)benzyl]quinolin-4(1H)-one | 365 | 366 | 1 |
| 9 | 1-[3-(2,6-diazaspiro[3.5]non-2-ylcarbonyl)-4-fluorobenzyl]quinolin-4(1H)-one | 405 | 406 | 1 |
| 10 | 1-[3-(2,5-diazabicyclo[2.2.2]oct-2-ylcarbonyl)-4-fluorobenzyl]quinolin-4(1H)-one | 391 | 392 | 1 |
| 11 | 1-(4-fluoro-3-{[4-(2-methylprolyl)piperazin-1-yl]carbonyl}benzyl)quinolin-4(1H)-one | 476 | 477 | 2 |
| 12 | 1-(4-fluoro-3-{[4-(3,3,3-trifluoro-N,N-dimethylalanyl)piperazin-1-yl]carbonyl}benzyl)quinolin-4(1H)-one | 518 | 519 | 2* |
| 13 | (2R)-2-[(4-{2-fluoro-5-[(4-oxoquinolin-1(4H)-yl)methyl]benzoyl}piperazin-1-yl)carbonyl]-2-methylazetidinium trifluoroacetate | 462 | 463 | 2 |
| 14 | 1-{4-fluoro-3-[(4-propionylpiperazin-1-yl)carbonyl]benzyl}-4-oxo-1,4-dihydrocinnolin-1-ium trifluoroacetate | 422 | 423 | 3* |
| 15 | 1-{3-[(3-ethyl-5,6-dihydro[1,2,4]triazolo[4,3-a]pyrazin-2-ium-7(8H)-yl)carbonyl]-4-fluorobenzyl}-4-oxo-1,4-dihydrocinnolin-1-ium bis(trifluoroacetate) | 432 | 433 | 3* |
| 16 | 1-(4-fluoro-3-{[3-(trifluoromethyl)-5,6-dihydro[1,2,4]triazolo[4,3-a]pyrazin-7(8H)-yl]carbonyl}benzyl)-4-oxo-1,4-dihydrocinnolin-1-ium trifluoroacetate | 472 | 473 | 3* |

*= without the final Boc deprotection

EXAMPLE 17

8-fluoro-1-(4-fluoro-3-{[3-(trfluoromethyl)-5,6-dihydro[1,2,4]triazolo[4,3-a]pyrazin-7(8H)-yl]carbonyl}benzyl)-4-oxo-1,4-dihydrocinnolin-1-ium trifluoroacetate (D6)

Step 1: methyl 2-amino-3-fluorobenzoate (D1)

2-amino-3-fluoro benzoic acid was dissolved in HCl (3 M solution in MeOH). The reaction mixture was heated to reflux for 2 h. Then, solvent was evaporated and the residue was partitioned between DCM and sat. sol. NaHCO$_3$. The aqueous phase was separated and extracted several times withn DCM. The combined organic layers were dried (Na$_2$SO$_4$) and solvent was evaporated under reduced pressure to afford the title compound as a yellow oil.

$^1$H NMR (300 MHz, CDCl$_3$) δ: 7.72-7.58 (m, 1H), 7.18-7.02 (m, 1H), 6.65-6.48 (m, 1H), 3.88 (s, 3H). MS (ES) C$_8$H$_8$FNO$_2$ requires: 169, Found: 170 (M+H)$^+$.

Step 2: 1-(2-amino-3-fluorophenyl)-2-(triphenylphosphoranylidene)ethanone (D2)

A suspension of methyl triphenylphosphonium bromide (2.4 eq) and sodium amide (3.2 eq) in toluene (0.1 M) was stirred at RT for 3 h. After cooling down to 0° C., a solution of D1 in toluene (0.1 M) was added to the suspension and the reaction mixture was heated to 50° C. for 3 h. 30 min. Then, The precipitate was filtered off and the solvent was evaporated under reduced pressure giving a crude that was purified by flash chromatography on silicagel, using AcOEt/PE (7:3) as solvent, affording the title compound as a yellow powder.

$^1$H NMR (500 MHz, CDCl$_3$) δ: 7.78-7.68 (m, 6H), 7.62-7.54 (m, 3H), 7.52-7.45 (m, 7H), 6.97-6.89 (m, 1H), 6.56-6.48 (m, 1H), 5.76 (bs, 2H), 4.32-4.20 (m, 1H). MS (ES) C$_{26}$H$_{21}$FNOP requires: 413, Found: 414 (M+H)$^+$.

Step 3: 8-fluoro-3-(triphenylphosphoranylidene)cinnolin-4(3H)-one (D3)

Isoamyl nitrite (1.9 eq) was added to a stirred solution of D2 in HCl (0.5 M solution in MeOH) at 0° C. After the consumption of the starting material (15-30 min), the solution was allowed to warm to RT and was made alkaline (pH=9) by addition of 10% NaOH. The resulting precipitate was collected by filtration affording the title compound as a white solid.

$^1$H NMR (500 MHz, CDCl$_3$) δ: 8.06-7.99 (m, 1H), 7.82-7.73 (m, 6H), 7.72-7.65 (m, 3H), 7.71-7.53 (m, 6H), 7.42-7.36 (m, 2H). MS (ES) C$_{26}$H$_{18}$FN$_2$OP requires: 424, Found: 425 (M+H)$^+$.

Step 4: {8-fluoro-1-[4-fluoro-3-(methoxycarbonyl)benzyl]-4-oxo-1,4-dihydrocinnolin-3-yl}(triphenyl)phosphonium bromide (D4)

A solution of D3 and methyl 5-(bromomethyl)-2-fluorobenzoate (prepared as described in US 2007/0021427) (1 eq) in ACN (0.1 M) was heated to reflux for 1 h 30 min. After cooling down, evaporation of the solvent under reduced pressure afforded the title compound as yellow foam.

$^1$H NMR (500 MHz, DMSO-d$_6$) δ: 8.05-8.01 (m, 1H), 8.01-7.98 (m, 1H), 7.92-7.86 (m, 3H), 7.84-7.69 (m, 14H), 7.54-7.48 (m, 1H), 7.29-7.21 (m, 1H), 5.74 (s, 2H), 3.83 (s, 3H). MS (ES) C$_{35}$H$_{26}$F$_2$N$_2$O$_3$P$^+$Br$^-$ requires: 591, Found: 591 (M$^+$).

Step 5: 1-(3-carboxy-4-fluorobenzyl)-8-fluoro-4-oxo-1,4-dihydrocinnolin-1-ium chloride (D5)

A solution of D4 in MeOH/20% NaOH (6:1, 0.1 M) was stirred at RT for 15 min. After evaporation of the solvents, the residue was partitioned between water and DCM. The aqueous phase was separated and brought to pH 1 with 6N HCl. The resulting precipitate was collected by filtration and washed with water affording the title compound as a yellow solid.

$^1$H NMR (300 MHz, DMSO-d$_6$) δ: 13.3 (bs, 1H), 8.03-7.97 (m, 1H), 7.94 (s, 1H), 7.76-7.66 (m, 2H), 7.52-7.43 (m, 2H), 7.32-7.24 (m, 1H), 5.76 (s, 2H). MS (ES) C$_{16}$H$_{11}$F$_2$N$_2$O$_3$$^+$Cl$^-$ requires: 316, Found: 317 (M+H)$^+$.

Step 6: 8-fluoro-1-(4-fluoro-3-{[3-(trifluoromethyl)-5,6-dihydroro[2,4]triazolo[4,3-α]pyrazin-7(8H)-yl]carbonyl}benzyl)-4-oxo-1,4-dihydrocinnolin-1-ium trifluoroacetate (D6)

A solution of D5, TBTU (1.5 eq) and TEA (2 eq) in DMF (0.15 M) was stirred at RT for 5 min. Then, TEA (3 eq) and 3-(trifluoromethyl)-5,6,7,8-tetrahydro[1,2,4]triazolo[4,3-a]pyrazin-7-ium chloride (1.5 eq) were added. The resulting reaction mixture was stirred at RT for 3 h and the product was purified by preparative RP-HPLC, using H$_2$O/ACN (0.1% TFA) as eluents. The pooled product fractions were lyophilized affording the title compound as a white solid.

$^1$H NMR (300 MHz, DMSO-d$_6$) δ: 8.01-7.94 (m, 1H), 7.93-7.86 (m, 1H), 7.75-7.63 (m, 1H), 7.51-7.42 (m, 2H), 7.40-7.28 (m, 2H), 5.75 (s, 2H), 5.02-4.80 (m, 1H), 4.72-4.64 (m, 1H), 4.28-4.19 (m, 1H), 4.18-4.08 (m, 1H), 4.01-3.93 (m, 1H), 3.68-3.59 (m, 1H). MS (ES) C$_{22}$H$_{16}$F$_5$N$_6$O$_2$$^+$C$_2$F$_3$O$_2$$^-$ requires: 490, Found: 491 (M+H)$^+$.

EXAMPLE 18

1-{3-[(4-ethyl-3-oxopiperazin-1-yl)carbonyl]-4-fluorobenzyl}-8-hydroxycinnolin-4(1H)-one

Step 1: 1-(3-carboxy-4-fluorobenzyl)-8-hydroxy-4-oxo-1,4-dihydrocinnolin-1-ium chloride (E1)

A solution of D5 in 9% LiOH (0.05 M) was heated at 160° C. under microwaves irradiation for 15 min. The aqueous phase was made acidic with 37% HCl. The resulting precipitate was collected by filtration affording the title compound as a yellow solid.

$^1$H NMR (400 MHz, DMSO-d$_6$) δ: 11.1 (s, 1H), 7.82 (s, 1H), 7.76-7.69 (m, 1H), 7.64-7.58 (m, 1H), 7.49-7.40 (m, 1H), 7.35-7.25 (m, 2H), 7.25-7.18 (m, 1H), 5.99 (s, 2H). MS (ES) C$_{16}$H$_{12}$FN$_2$O$_4$$^+$Cl$^-$ requires: 314, Found: 315 (M+H)$^-$.

Step 2: 1-{3-[(4-ethyl-3-oxopiperazin-1-yl)carbonyl]-4-fluorobenzyl}-8-hydroxy-4-oxo-1,4-dihydrocinnolin-1-ium trifluoroacetate (E2)

A solution of E1 and TBTU (1.0 eq) in dry DMF (0.15 M) was stirred at RT for 5 minutes and then DIPEA (1.0 eq) and 1-ethylpiperazin-2-one (2.0 eq) were added. The reaction mixture was stirred at RT for 3 h and the product was purified by preparative RP-HPLC, using H$_2$O/ACN (0.1% TFA) as eluents. The pooled product fractions were lyophilized affording the title compound as a white solid.

$^1$H NMR (400 MHz, DMSO-d$_6$) δ: 11.04 (bs, 1H), 7.80 (s, 1H), 7.60 (d, 1H, J=7.4 Hz), 7.40-7.30 (m, 4H), 7.20 (d, 1H, J=7.4 Hz), 5.99 (s, 2H), 4.20-4.10 (m, 1H), 3.90-3.80 (m, 1H), 3.80-3.70 (m, 1H), 3.45-3.35 (m, 2H), 3.35-3.25 (m, 2H), 3.20-3.10 (m, 1H), 1.10-1.00 (m, 3H). MS (ES) C$_{22}$H$_{21}$FN$_4$O$_4$ requires: 424, Found: 425 (M+H)$^+$.

The following Examples were prepared according to the procedures of the Examples above.

| Example | Compound Name | MWt | [M + H]+ | Procedure of Example |
|---|---|---|---|---|
| 19 | 1-{4-fluoro-3-[(3-oxo-4-phenylpiperazin-1-yl)carbonyl]benzyl}-4-oxo-1,4-dihydroquinolinium trifluoroacetate | 455 | 456 | 1* |
| 20 | 1-{3-[(4-cyclopentyl-3-oxopiperazin-1-yl)carbonyl]-4-fluorobenzyl}-4-oxo-1,4-dihydroquinolinium trifluoroacetate | 447 | 448 | 1* |
| 21 | 1-(4-fluoro-3-{[4-(4-fluorophenyl)-3,6-dihydropyridin-1(2H)-yl]carbonyl}benzyl)-4-oxo-1,4-dihydroquinolinium trifluoroacetate | 456 | 457 | 1* |
| 22 | 1-(4-fluoro-3-{[1-(2,2,2-trifluoroethyl)-1,4,6,7-tetrahydro-5H-[1,2,3]triazolo[4,5-c]pyridin-5-yl]carbonyl}benzyl)-4-oxo-1,4-dihydrocinnolin-1-ium trifluoroacetate | 486 | 487 | 3* |
| 23 | 1-{3-[(4-cyclohexyl-3-oxopiperazin-1-yl)carbonyl]-4-fluorobenzyl}-4-oxo-1,4-dihydrocinnolin-1-ium trifluoroacetate | 462 | 463 | 3* |
| 24 | 1-{3-[(4-cyclopentyl-3-oxopiperazin-1-yl)carbonyl]-4-fluorobenzyl}-4-oxo-1,4-dihydrocinnolin-1-ium trifluoroacetate | 448 | 449 | 3* |
| 25 | 1-(3-{[4-(tert-butoxycarbonyl)piperazin-1-yl]carbonyl}-4-fluorobenzyl)-4-oxo-1,4-dihydrocinnolin-1-ium trifluoroacetate | 466 | 467 | 3* |
| 26 | 1-[4-fluoro-3-(piperazin-1-ylcarbonyl)benzyl]cinnolin-4(1H)-one | 366 | 367 | 3 |
| 27 | 2-(4-{2-fluoro-5-[(4-oxocinnolin-1(4H)-yl)methyl]benzoyl}piperazin-1-yl)pyrimidin-1-ium trifluoroacetate | 444 | 445 | 3* |
| 28 | 1-{4-fluoro-3-[(3-oxo-4-phenylpiperazin-1-yl)carbonyl]benzyl}-4-oxo-1,4-dihydrocinnolin-1-ium trifluoroacetate | 456 | 457 | 3* |
| 29 | 1-{4-fluoro-3-[(4-isobutyrylpiperazin-1-yl)carbonyl]benzyl}-4-oxo-1,4-dihydrocinnolin-1-ium trifluoroacetate | 436 | 437 | 3* |
| 30 | 1-(4-fluoro-3-{[4-(trifluoroacetyl)piperazin-1-yl]carbonyl}benzyl)-4-oxo-1,4-dihydrocinnolin-1-ium trifluoroacetate | 462 | 463 | 3* |
| 31 | 1-{4-fluoro-3-[(4-{[(2S)-2-(4-fluorobenzyl)pyrrolidinium-2-yl]carbonyl}piperazin-1-yl)carbonyl]benzyl}-4-oxo-1,4-dihydrocinnolin-1-ium bis(trifluoroacetate) | 571 | 572 | 3 |
| 32 | 1-{4-fluoro-3-[(4-{[(2R)-2-methylazetidin-2-yl]carbonyl}piperazin-1-yl)carbonyl]benzyl}cinnolin-4(1H)-one | 463 | 464 | 3 |
| 33 | 1-[3-(2,5-diazabicyclo[2.2.2]oct-2-ylcarbonyl)-4-fluorobenzyl]cinnolin-4(1H)-one | 392 | 393 | 3 |
| 34 | 1-[3-(1,4-diazepan-1-ylcarbonyl)-4-fluorobenzyl]cinnolin-4(1H)-one | 380 | 381 | 3 |
| 35 | 1-(4-fluoro-3-{[3-(pentafluoroethyl)-5,6-dihydro[1,2,4]triazolo[4,3-a]pyrazin-7(8H)-yl]carbonyl}benzyl)-4-oxo-1,4-dihydrocinnolin-1-ium trifluoroacetate | 522 | 545 [M + Na]+ | 3* |
| 36 | 1-(3-{[4-(2-chlorophenyl)-3-oxopiperazin-1-yl]carbonyl}-4-fluorobenzyl)-4-oxo-1,4-dihydrocinnolin-1-ium trifluoroacetate | 490 | 491 | 3* |
| 37 | 1-(3-{[4-(3-chlorophenyl)-3-oxopiperazin-1-yl]carbonyl}-4-fluorobenzyl)-4-oxo-1,4-dihydrocinnolin-1-ium trifluoroacetate | 490 | 491 | 3* |
| 38 | 1-(3-{[4-(2-chloro-4-fluorophenyl)-3-oxopiperazin-1-yl]carbonyl}-4-fluorobenzyl)-4-oxo-1,4-dihydrocinnolin-1-ium trifluoroacetate | 508 | 509 | 3* |
| 39 | 1-(3-{[4-(3,4-difluorophenyl)-3-oxopiperazin-1-yl]carbonyl}-4-fluorobenzyl)-4-oxo-1,4-dihydrocinnolin-1-ium trifluoroacetate | 492 | 493 | 3* |
| 40 | 1-(3-{[3-[(dimethylamino)methyl]-5,6-dihydro[1,2,4]triazolo[4,3-a]pyrazin-7(8H)-yl]carbonyl}-4-fluorobenzyl)cinnolin-4(1H)-one | 461 | 462 | 3* |

-continued

| Example | Compound Name | MWt | [M + H]+ | Procedure of Example |
|---|---|---|---|---|
| 41 | 1-{3-[(3-cyclobutyl-5,6-dihydro[1,2,4]triazolo[4,3-a]pyrazin-7(8H)-yl)carbonyl]-4-fluorobenzyl}-4-oxo-1,4-dihydrocinnolin-1-ium trifluoroacetate | 458 | 459 | 3* |
| 42 | 1-{3-[(3-tert-butyl-5,6-dihydro[1,2,4]triazolo[4,3-a]pyrazin-7(8H)-yl)carbonyl]-4-fluorobenzyl}-4-oxo-1,4-dihydrocinnolin-1-ium trifluoroacetate | 460 | 461 | 3* |
| 43 | 1-(4-fluoro-3-{[3-(2,2,2-trifluoroethyl)-5,6-dihydro[1,2,4]triazolo[4,3-a]pyrazin-7(8H)-yl]carbonyl}benzyl)-4-oxo-1,4-dihydrocinnolin-1-ium trifluoroacetate | 486 | 487 | 3* |
| 44 | 1-(4-fluoro-3-{[4-(4-fluorophenyl)-3,6-dihydropyridin-1(2H)-yl]carbonyl}benzyl)cinnolin-4(1H)-one | 457 | 458 | 3* |
| 45 | 5-fluoro-1-(4-fluoro-3-{[3-(trifluoromethyl)-5,6-dihydro[1,2,4]triazolo[4,3-a]pyrazin-7(8H)-yl]carbonyl}benzyl)-4-oxo-1,4-dihydrocinnolin-1-ium trifluoroacetate | 490 | 491 | 17 |
| 46 | 1-{3-[(4-cyclohexyl-3-oxopiperazin-1-yl)carbonyl]-4-fluorobenzyl}-5-fluoro-4-oxo-1,4-dihydrocinnolin-1-ium trifluoroacetate | 480 | 481 | 17 |
| 47 | 1-{3-[(4-cyclopentyl-3-oxopiperazin-1-yl)carbonyl]-4-fluorobenzyl}-5-fluoro-4-oxo-1,4-dihydrocinnolin-1-ium trifluoroacetate | 466 | 467 | 17 |
| 48 | 1-[3-(2,5-diazabicyclo[2.2.2]oct-2-ylcarbonyl)-4-fluorobenzyl]-5-fluorocinnolin-4(1H)-one | 410 | 411 | 17 |
| 49 | 6-fluoro-1-(4-fluoro-3-{[3-(trifluoromethyl)-5,6-dihydro[1,2,4]triazolo[4,3-a]pyrazin-7(8H)-yl]carbonyl}benzyl)-4-oxo-1,4-dihydrocinnolin-1-ium trifluoroacetate | 490 | 491 | 17 |
| 50 | 1-{3-[(4-cyclohexyl-3-oxopiperazin-1-yl)carbonyl]-4-fluorobenzyl}-6-fluoro-4-oxo-1,4-dihydrocinnolin-1-ium trifluoroacetate | 480 | 481 | 17 |
| 51 | 1-{3-[(4-cyclopentyl-3-oxopiperazin-1-yl)carbonyl]-4-fluorobenzyl}-6-fluoro-4-oxo-1,4-dihydrocinnolin-1-ium trifluoroacetate | 466 | 467 | 17 |
| 52 | 1-[3-(2,5-diazabicyclo[2.2.2]oct-2-ylcarbonyl)-4-fluorobenzyl]-6-fluorocinnolin-4(1H)-one | 410 | 411 | 17 |
| 53 | 7-fluoro-1-(4-fluoro-3-{[3-(trifluoromethyl)-5,6-dihydro[1,2,4]triazolo[4,3-a]pyrazin-7(8H)-yl]carbonyl}benzyl)-4-oxo-1,4-dihydrocinnolin-1-ium trifluoroacetate | 490 | 491 | 17 |
| 54 | 1-{3-[(4-cyclohexyl-3-oxopiperazin-1-yl)carbonyl]-4-fluorobenzyl}-7-fluoro-4-oxo-1,4-dihydrocinnolin-1-ium trifluoroacetate | 480 | 481 | 17 |
| 55 | 1-{3-[(4-cyclopentyl-3-oxopiperazin-1-yl)carbonyl]-4-fluorobenzyl}-7-fluoro-4-oxo-1,4-dihydrocinnolin-1-ium trifluoroacetate | 466 | 467 | 17 |
| 56 | 1-[3-(2,5-diazabicyclo[2.2.2]oct-2-ylcarbonyl)-4-fluorobenzyl]-7-fluorocinnolin-4(1H)-one | 410 | 411 | 17 |
| 57 | 1-{3-[(4-cyclohexyl-3-oxopiperazin-1-yl)carbonyl]-4-fluorobenzyl}-8-fluoro-4-oxo-1,4-dihydrocinnolin-1-ium trifluoroacetate | 480 | 481 | 17 |
| 58 | 1-{3-[(4-cyclopentyl-3-oxopiperazin-1-yl)carbonyl]-4-fluorobenzyl}-8-fluoro-4-oxo-1,4-dihydrocinnolin-1-ium trifluoroacetate | 466 | 467 | 17 |
| 59 | 1-[3-(2,5-diazabicyclo[2.2.2]oct-2-ylcarbonyl)-4-fluorobenzyl]-8-fluorocinnolin-4(1H)-one | 410 | 411 | 17 |

-continued

| Example | Compound Name | MWt | [M + H]+ | Procedure of Example |
|---|---|---|---|---|
| 60 | 1-(4-fluoro-3-{[3-(trifluoromethyl)-5,6-dihydro[1,2,4]triazolo[4,3-a]pyrazin-7(8H)-yl]carbonyl}benzyl)-7-methoxy-4-oxo-1,4-dihydrocinnolin-1-ium trifluoroacetate | 502 | 503 | 18 |
| 61 | 1-{3-[(4-cyclohexyl-3-oxopiperazin-1-yl)carbonyl]-4-fluorobenzyl}-7-methoxy-4-oxo-1,4-dihydrocinnolin-1-ium trifluoroacetate | 492 | 493 | 18 |
| 62 | 1-{3-[(4-cyclopentyl-3-oxopiperazin-1-yl)carbonyl]-4-fluorobenzyl}-7-methoxy-4-oxo-1,4-dihydrocinnolin-1-ium trifluoroacetate | 478 | 479 | 18 |
| 63 | 1-[3-(2,5-diazabicyclo[2.2.2]oct-2-ylcarbonyl)-4-fluorobenzyl]-7-methoxycinnolin-4(1H)-one | 422 | 423 | 18 |
| 64 | 1-(4-fluoro-3-{[3-(trifluoromethyl)-5,6-dihydro[1,2,4]triazolo[4,3-a]pyrazin-7(8H)-yl]carbonyl}benzyl)-8-hydroxy-4-oxo-1,4-dihydrocinnolin-1-ium trifluoroacetate | 488 | 489 | 18 |
| 65 | 1-{3-[(4-cyclopentyl-3-oxopiperazin-1-yl)carbonyl]-4-fluorobenzyl}-8-hydroxy-4-oxo-1,4-dihydrocinnolin-1-ium trifluoroacetate | 464 | 465 | 18 |
| 66 | 1-(3-{[4-(2-chloro-4-fluorophenyl)-3-oxopiperazin-1-yl]carbonyl}-4-fluorobenzyl)-8-hydroxy-4-oxo-1,4-dihydrocinnolin-1-ium trifluoroacetate | 524 | 525 | 18 |
| 67 | 1-{4-fluoro-3-[(4-propionylpiperazin-1-yl)carbonyl]benzyl}-8-hydroxy-4-oxo-1,4-dihydrocinnolin-1-ium trifluoroacetate | 438 | 439 | 18 |
| 68 | 1-{4-fluoro-3-[(4-oxooctahydro-2H-pyrido[1,2-a]pyrazin-2-yl)carbonyl]benzyl}-8-hydroxy-4-oxo-1,4-dihydrocinnolin-1-ium trifluoroacetate | 450 | 451 | 18 |
| 69 | 1-{4-fluoro-3-[(6-oxohexahydropyrazino[2,1-c][1,4]oxazin-8(1H)-yl)carbonyl]benzyl}-8-hydroxy-4-oxo-1,4-dihydrocinnolin-1-ium trifluoroacetate | 452 | 453 | 18 |

*= without the final Boc deprotection

The invention claimed is:
1. A compound of formula I:

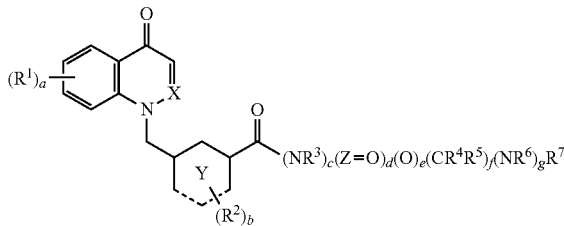

(I)

wherein:
a is 0, 1, 2, 3 or 4;
b is 0, 1, 2, 3 or 4;
c is 0 or 1;
d is 0 or 1;
e is 0 or 1;
f is 0, 1, 2, 3, 4 or 5;
g is 0 or 1;
X is N or CH;
Y is phenyl, a 5 membered unsaturated heterocycle containing 1, 2, 3 or 4 heteroatoms independently selected from O, N and S, but not more than one of which is O or S, or a 6 membered unsaturated heterocycle containing 1, 2, 3 or 4 nitrogen atoms;
Z is C or SO;
each $R^1$ is independently hydroxy, halogen, cyano, nitro, $C_{1-6}$alkyl, halo$C_{1-6}$alkyl, $C_{1-6}$alkoxy or halo$C_{1-6}$alkoxy;
each $R^2$ is independently hydroxy, halogen, cyano, nitro, $C_{1-6}$alkyl, halo$C_{1-6}$alkyl, $C_{1-6}$alkoxy or halo$C_{1-6}$alkoxy;
$R^3$ is hydrogen or $C_{1-6}$alkyl;
each of $R^4$ and $R^5$ is independently hydrogen or $C_{1-6}$alkyl;
$R^6$ is hydrogen or $C_{1-6}$alkyl; and
$R^7$ is azetidinyl optionally substituted by one or more groups independently selected from A-$(CR^8R^9)_qR^{10}$;
each A is independently a direct bond, O, $(CH_2)_s(C=O)_t$, $(C=O)NR^{11}$, $NR^{11}(C=O)$, $(C=O)O$, $O(C=O)$, $(C=S)NR^{11}$, $NR^{11}$ or $S(O)_r$;
each q is independently 0, 1, 2, 3, or 4;
r is 0, 1 or 2;
s is 0, 1, 2 or 3;
t is 1 or 2;
each of $R^8$ and $R^9$ is independently hydrogen, hydroxy, halogen, $C_{1-6}$alkyl or halo$C_{1-6}$alkyl;
each $R^{10}$ is independently hydroxy, oxo, cyano, halogen, nitro, $C_{1-6}$alkyl, $C_{2-10}$alkenyl, halo$C_{1-6}$alkyl, amino, $C_{1-6}$alkylamino, di($C_{1-6}$alkyl)amino, ($C_{1-6}$alkylcarbonyl)amino or a ring which is: $C_{3-10}$cycloalkyl; $C_{6-10}$aryl;

azetidinyl; a 5 or 6 membered saturated or partially saturated heterocyclic ring containing one, two or three atoms independently selected from N, O and S; a 5 membered heteroaromatic ring containing 1, 2, 3 or 4 heteroatoms independently selected from N, O and S, not more than one heteroatom of which is O or S; a 6 membered heteroaromatic ring containing 1, 2 or 3 nitrogen atoms; or a 7-13 membered unsaturated, partially saturated, or saturated heterocyclic ring containing 1, 2, 3 or 4 heteroatoms independently selected from N, O and S; any of which rings being optionally substituted by one or more groups independently selected from $R^{12}$;

$R^{11}$ is hydrogen or $R^{10}$;

each $R^{12}$ is independently hydroxy, oxo, cyano, halogen, nitro, $C_{1-6}$alkyl, $C_{1-6}$alkoxy, $C_{2-10}$alkenyl, halo$C_{1-6}$alkyl, halo$C_{1-6}$alkoxy, $C_{1-6}$alkylcarbonyl, —O(C=O)$C_{1-6}$alkyl, —O(C=O)O$C_{1-6}$alkyl, amino, $C_{1-6}$alkylamino, di($C_{1-6}$alkyl)amino, ($C_{1-6}$alkylsulfonyl)amino, $C_{6-10}$aryl, $C_{1-6}$aryl$C_{1-6}$alkyl, a 5 membered heteroaromatic ring containing 1, 2, 3 or 4 heteroatoms independently selected from N, O and S, not more than one heteroatom of which is O or S or a 6 membered heteroaromatic ring containing 1, 2 or 3 nitrogen atoms; any of which rings being optionally substituted by one or more groups independently selected from halogen, $C_{1-6}$alkyl and halo$C_{1-6}$alkyl;

or a pharmaceutically acceptable salt, stereoisomer or tautomer thereof.

2. A compound of claim 1 of formula II:

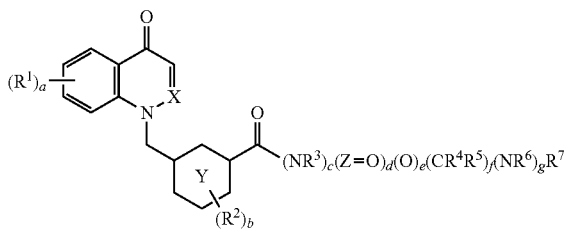

wherein:

a, b, c, d, e, f, g, X, Z, $R^1$, $R^2$, $R^3$, $R^4$, $R^5$, $R^6$ and $R^7$ are as defined in claim 1;

Y is phenyl or a 6 membered unsaturated heterocycle containing 1, 2, 3 or 4 nitrogen atoms;

or a pharmaceutically acceptable salt, stereoisomer or tautomer thereof.

3. A compound of claim 2 wherein Y is phenyl and each of c, d, e, f and g is 0.

4. A compound of claim 2 wherein:

Y is phenyl;

b is 1;

each of c, d, e, f and g is 0; and $R^7$ is azetidinyl optionally substituted by one or more groups independently selected from A-$(CR^8R^9)_qR^{10}$.

5. A compound of claim 1 of formula III:

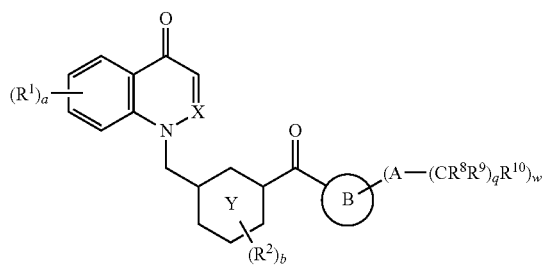

wherein:

a, b, q, A, $R^1$, $R^2$, $R^8$, $R^9$ and $R^{10}$ are as defined in claim 1;

Y is phenyl or a 6 membered unsaturated heterocycle containing 1, 2, 3 or 4 nitrogen atoms;

w is 0, 1, 2, 3 or 4;

B is azetidinyl;

or a pharmaceutically acceptable salt, stereoisomer or tautomer thereof.

6. A compound of claim 5 wherein:

Y is phenyl;

A is a direct bond, CO or COO; and $R^{10}$ is oxo, halogen, $C_{1-6}$alkyl, halo$C_{1-6}$alkyl, amino, $C_{1-6}$alkylamino, di($C_{1-6}$alkyl)amino, $C_{3-7}$cycloalkyl, $C_{6-10}$aryl, azetidinyl, a 5 or 6 membered saturated or partially saturated heterocyclic ring containing one, two or three atoms independently selected from N, O and S or a 6 membered heteroaromatic ring containing 1, 2 or 3 nitrogen atoms; any of which rings being optionally substituted by one or more groups independently selected from $R^{12}$;

$R^{12}$ is as defined in claim 1.

7. A pharmaceutical composition comprising a compound of claim 1, or a pharmaceutically acceptable salt, stereoisomer or tautomer thereof in association with a pharmaceutically acceptable carrier.

8. A method of treating cardiovascular diseases, which method comprises administration to a patient in need thereof of an effective amount of a compound of claim 1 or a composition comprising a compound of claim 1.

9. A compound selected from:
1-[3-(8-aza-1-azoniaspiro[4.5]dec-8-ylcarbonyl)-4-fluorobenzyl]-4-oxo-1,4-dihydroquinolinium bis(trifluoroacetate);
1-[4-fluoro-3-({4-[2-(4-fluorobenzyl)prolyl]piperazin-1-yl}carbonyl)benzyl]quinolin-4(1H)-one;
1-[3-(8-aza-1-azoniaspiro[4.5]dec-8-ylcarbonyl)-4-fluorobenzyl]-4-oxo-1,4-dihydrocinnolin-1-ium bis(trifluoroacetate);
1-[3-(1,4-diazepan-1-ylcarbonyl)-4-fluorobenzyl]quinolin-4(1H)-one;
1-{4-fluoro-3-[(4-propionylpiperazin-1-yl)carbonyl]benzyl}quinolin-4(1H)-one;
1-(4-fluoro-3-{[3-(trifluoromethyl)-5,6-dihydro[1,2,4]triazolo[4,3-a]pyrazin-7(8H)-yl]carbonyl}benzyl)quinolin-4(1H)-one;
1-[3-(1,8-diazaspiro[4.5]dec-8-ylcarbonyl)-4-fluorobenzyl]quinolin-4(1H)-one;
1-[4-fluoro-3-(piperazin-1-ylcarbonyl)benzyl]quinolin-4(1H)-one;
1-[3-(2,6-diazaspiro[3.5]non-2-ylcarbonyl)-4-fluorobenzyl]quinolin-4(1H)-one;

1-[3-(2,5-diazabicyclo[2.2.2]oct-2-ylcarbonyl)-4-fluorobenzyl]quinolin-4(1H)-one;
1-(4-fluoro-3-{[4-(2-methylprolyl)piperazin-1-yl]carbonyl}benzyl)quinolin-4(1H)-one;
1-(4-fluoro-3-{[4-(3,3,3-trifluoro-N,N-dimethylalanyl)piperazin-1-yl]carbonyl}benzyl)quinolin-4(1H)-one;
(2R)-2-[(4-{2-fluoro-5-[(4-oxoquinolin-1(4H)-yl)methyl]benzoyl}piperazin-1-yl)carbonyl]-2-methylazetidinium trifluoroacetate;
1-{4-fluoro-3-[(4-propionylpiperazin-1-yl)carbonyl]benzyl}-4-oxo-1,4-dihydrocinnolin-1-ium trifluoroacetate;
1-{3-[(3-ethyl-5,6-dihydro[1,2,4]triazolo[4,3-a]pyrazin-2-ium-7(8H)-yl)carbonyl]-4-fluorobenzyl}-4-oxo-1,4-dihydrocinnolin-1-ium bis(trifluoroacetate);
1-(4-fluoro-3-{[3-(trifluoromethyl)-5,6-dihydro[1,2,4]triazolo[4,3-a]pyrazin-7(8H)-yl]carbonyl}benzyl)-4-oxo-1,4-dihydrocinnolin-1-ium trifluoroacetate;
8-fluoro-1-(4-fluoro-3-{[3-(trifluoromethyl)-5,6-dihydro[1,2,4]triazolo[4,3-a]pyrazin-7(8H)-yl]carbonyl}benzyl)-4-oxo-1,4-dihydrocinnolin-1-ium trifluoroacetate;
1-{3-[(4-ethyl-3-oxopiperazin-1-yl)carbonyl]-4-fluorobenzyl}-8-hydroxycinnolin-4(1H)-one;
1-{4-fluoro-3-[(3-oxo-4-phenylpiperazin-1-yl)carbonyl]benzyl}-4-oxo-1,4-dihydroquinolinium trifluoroacetate;
1-{3-[(4-cyclopentyl-3-oxopiperazin-1-yl)carbonyl]-4-fluorobenzyl}-4-oxo-1,4-dihydroquinolinium trifluoroacetate;
1-(4-fluoro-3-{[4-(4-fluorophenyl)-3,6-dihydropyridin-1(2H)-yl]carbonyl}benzyl)-4-oxo-1,4-dihydroquinolinium trifluoroacetate;
1-(4-fluoro-3-{[1-(2,2,2-trifluoroethyl)-1,4,6,7-tetrahydro-5H-[1,2,3]triazolo[4,5-c]pyridin-5-yl]carbonyl}benzyl)-4-oxo-1,4-dihydrocinnolin-1-ium trifluoroacetate;
1-{3-[(4-cyclohexyl-3-oxopiperazin-1-yl)carbonyl]-4-fluorobenzyl}-4-oxo-1,4-dihydrocinnolin-1-ium trifluoroacetate;
1-{3-[(4-cyclopentyl-3-oxopiperazin-1-yl)carbonyl]-4-fluorobenzyl}-4-oxo-1,4-dihydrocinnolin-1-ium trifluoroacetate;
1-(3-{[4-(tert-butoxycarbonyl)piperazin-1-yl]carbonyl}-4-fluorobenzyl)-4-oxo-1,4-dihydrocinnolin-1-ium trifluoroacetate;
1-[4-fluoro-3-(piperazin-1-ylcarbonyl)benzyl]cinnolin-4(1H)-one;
2-(4-{2-fluoro-5-[(4-oxocinnolin-1(4H)-yl)methyl]benzoyl}piperazin-1-yl)pyrimidin-1-ium trifluoroacetate;
1-{4-fluoro-3-[(3-oxo-4-phenylpiperazin-1-yl)carbonyl]benzyl}-4-oxo-1,4-dihydrocinnolin-1-ium trifluoroacetate;
1-{4-fluoro-3-[(4-isobutyrylpiperazin-1-yl)carbonyl]benzyl}-4-oxo-1,4-dihydrocinnolin-1-ium trifluoroacetate;
1-(4-fluoro-3-{[4-(trifluoroacetyl)piperazin-1-yl]carbonyl}benzyl)-4-oxo-1,4-dihydrocinnolin-1-ium trifluoroacetate;
1-{4-fluoro-3-[(4-{[(2S)-2-(4-fluorobenzyl)pyrrolidinium-2-yl]carbonyl}piperazin-1-yl)carbonyl]benzyl}-4-oxo-1,4-dihydrocinnolin-1-ium bis(trifluoroacetate); 1-{4-fluoro-3-[(4-{[(2R)-2-methylazetidin-2-yl]carbonyl}piperazin-1-yl)carbonyl]benzyl}cinnolin-4(1H)-one;
1-[3-(2,5-diazabicyclo[2.2.2]oct-2-ylcarbonyl)-4-fluorobenzyl]cinnolin-4(1H)-one;
1-[3-(1,4-diazepan-1-ylcarbonyl)-4-fluorobenzyl]cinnolin-4(1H)-one;
1-(4-fluoro-3-{[3-(pentafluoroethyl)-5,6-dihydro[1,2,4]triazolo[4,3-a]pyrazin-7(8H)-yl]carbonyl}benzyl)-4-oxo-1,4-dihydrocinnolin-1-ium trifluoroacetate;
1-(3-{[4-(2-chlorophenyl)-3-oxopiperazin-1-yl]carbonyl}-4-fluorobenzyl)-4-oxo-1,4-dihydrocinnolin-1-ium trifluoroacetate;
1-(3-{[4-(3-chlorophenyl)-3-oxopiperazin-1-yl]carbonyl}-4-fluorobenzyl)-4-oxo-1,4-dihydrocinnolin-1-ium trifluoroacetate;
1-(3-{[4-(2-chloro-4-fluorophenyl)-3-oxopiperazin-1-yl]carbonyl}-4-fluorobenzyl)-4-oxo-1,4-dihydrocinnolin-1-ium trifluoroacetate;
1-(3-{[4-(3,4-difluorophenyl)-3-oxopiperazin-1-yl]carbonyl}-4-fluorobenzyl)-4-oxo-1,4-dihydrocinnolin-1-ium trifluoroacetate;
1-(3-{[3-[(dimethylamino)methyl]-5,6-dihydro[1,2,4]triazolo[4,3-a]pyrazin-7(8H)-yl]carbonyl}-4-fluorobenzyl)cinnolin-4(1H)-one;
1-{3-[(3-cyclobutyl-5,6-dihydro[1,2,4]triazolo[4,3-a]pyrazin-7(8H)-yl)carbonyl]-4-fluorobenzyl}-4-oxo-1,4-dihydrocinnolin-1-ium trifluoroacetate;
1-{3-[(3-tert-butyl-5,6-dihydro[1,2,4]triazolo[4,3-a]pyrazin-7(8H)-yl)carbonyl]-4-fluorobenzyl}-4-oxo-1,4-dihydrocinnolin-1-ium trifluoroacetate;
1-(4-fluoro-3-{[3-(2,2,2-trifluoroethyl)-5,6-dihydro[1,2,4]triazolo[4,3-a]pyrazin-7(8H)-yl]carbonyl}benzyl)-4-oxo-1,4-dihydrocinnolin-1-ium trifluoroacetate;
1-(4-fluoro-3-{[4-(4-fluorophenyl)-3,6-dihydropyridin-1(2H)-yl]carbonyl}benzyl)cinnolin-4(1H)-one;
5-fluoro-1-(4-fluoro-3-{[3-(trifluoromethyl)-5,6-dihydro[1,2,4]triazolo[4,3-a]pyrazin-7(8H)-yl]carbonyl}benzyl)-4-oxo-1,4-dihydrocinnolin-1-ium trifluoroacetate;
1-{3-[(4-cyclohexyl-3-oxopiperazin-1-yl)carbonyl]-4-fluorobenzyl}-5-fluoro-4-oxo-1,4-dihydrocinnolin-1-ium trifluoroacetate;
1-{3-[(4-cyclopentyl-3-oxopiperazin-1-yl)carbonyl]-4-fluorobenzyl}-5-fluoro-4-oxo-1,4-dihydrocinnolin-1-ium trifluoroacetate;
1-[3-(2,5-diazabicyclo[2.2.2]oct-2-ylcarbonyl)-4-fluorobenzyl]-5-fluorocinnolin-4(1H)-one;
6-fluoro-1-(4-fluoro-3-{[3-(trifluoromethyl)-5,6-dihydro[1,2,4]triazolo[4,3-a]pyrazin-7(8H)-yl]carbonyl}benzyl)-4-oxo-1,4-dihydrocinnolin-1-ium trifluoroacetate;
1-{3-[(4-cyclohexyl-3-oxopiperazin-1-yl)carbonyl]-4-fluorobenzyl}-6-fluoro-4-oxo-1,4-dihydrocinnolin-1-ium trifluoroacetate;
1-{3-[(4-cyclopentyl-3-oxopiperazin-1-yl)carbonyl]-4-fluorobenzyl}-6-fluoro-4-oxo-1,4-dihydrocinnolin-1-ium trifluoroacetate;
1-[3-(2,5-diazabicyclo[2.2.2]oct-2-ylcarbonyl)-4-fluorobenzyl]-6-fluorocinnolin-4(1H)-one;
7-fluoro-1-(4-fluoro-3-{[3-(trifluoromethyl)-5,6-dihydro[1,2,4]triazolo[4,3-a]pyrazin-7(8H)-yl]carbonyl}benzyl)-4-oxo-1,4-dihydrocinnolin-1-ium trifluoroacetate;
1-{3-[(4-cyclohexyl-3-oxopiperazin-1-yl)carbonyl]-4-fluorobenzyl}-7-fluoro-4-oxo-1,4-dihydrocinnolin-1-ium trifluoroacetate;
1-{3-[(4-cyclopentyl-3-oxopiperazin-1-yl)carbonyl]-4-fluorobenzyl}-7-fluoro-4-oxo-1,4-dihydrocinnolin-1-ium trifluoroacetate;
1-[3-(2,5-diazabicyclo[2.2.2]oct-2-ylcarbonyl)-4-fluorobenzyl]-7-fluorocinnolin-4(1H)-one;

1-{3-[(4-cyclohexyl-3-oxopiperazin-1-yl)carbonyl]-4-fluorobenzyl}-8-fluoro-4-oxo-1,4-dihydrocinnolin-1-ium trifluoroacetate;

1-{3-[(4-cyclopentyl-3-oxopiperazin-1-yl)carbonyl]-4-fluorobenzyl}-8-fluoro-4-oxo-1,4-dihydrocinnolin-1-ium trifluoroacetate;

1-[3-(2,5-diazabicyclo[2.2.2]oct-2-ylcarbonyl)-4-fluorobenzyl]-8-fluorocinnolin-4(1H)-one;

1-(4-fluoro-3-{[3-(trifluoromethyl)-5,6-dihydro[1,2,4]triazolo[4,3-a]pyrazin-7(8H)-yl]carbonyl}benzyl)-7-methoxy-4-oxo-1,4-dihydrocinnolin-1-ium trifluoroacetate;

1-{3-[(4-cyclohexyl-3-oxopiperazin-1-yl)carbonyl]-4-fluorobenzyl}-7-methoxy-4-oxo-1,4-dihydrocinnolin-1-ium trifluoroacetate;

1-{3-[(4-cyclopentyl-3-oxopiperazin-1-yl)carbonyl]-4-fluorobenzyl}-7-methoxy-4-oxo-1,4-dihydrocinnolin-1-ium trifluoroacetate;

1-[3-(2,5-diazabicyclo[2.2.2]oct-2-ylcarbonyl)-4-fluorobenzyl]-7-methoxycinnolin-4(1H)-one;

1-(4-fluoro-3-{[3-(trifluoromethyl)-5,6-dihydro[1,2,4]triazolo[4,3-a]pyrazin-7(8H)-yl]carbonyl}benzyl)-8-hydroxy-4-oxo-1,4-dihydrocinnolin-1-ium trifluoroacetate;

1-{3-[(4-cyclopentyl-3-oxopiperazin-1-yl)carbonyl]-4-fluorobenzyl}-8-hydroxy-4-oxo-1,4-dihydrocinnolin-1-ium trifluoroacetate;

1-(3-{[4-(2-chloro-4-fluorophenyl)-3-oxopiperazin-1-yl]carbonyl}-4-fluorobenzyl)-8-hydroxy-4-oxo-1,4-dihydrocinnolin-1-ium trifluoroacetate;

1-{4-fluoro-3-[(4-propionylpiperazin-1-yl)carbonyl]benzyl}-8-hydroxy-4-oxo-1,4-dihydrocinnolin-1-ium trifluoroacetate;

1-{4-fluoro-3-[(4-oxooctahydro-2H-pyrido[1,2-a]pyrazin-2-yl)carbonyl]benzyl}-8-hydroxy-4-oxo-1,4-dihydrocinnolin-1-ium trifluoroacetate; and 1-{4-fluoro-3-[(6-oxohexahydropyrazino[2,1-c][1,4]oxazin-8(1H)-yl)carbonyl]benzyl}-8-hydroxy-4-oxo-1,4-dihydrocinnolin-1-ium trifluoroacetate;

and other pharmaceutically acceptable salts, free bases and tautomers thereof.

\* \* \* \* \*